US007217519B1

(12) United States Patent
Johnson et al.

(10) Patent No.: US 7,217,519 B1
(45) Date of Patent: May 15, 2007

(54) *HISTOPLASMA CAPSULATUM* CHITIN SYNTHASE SEQUENCES AND THEIR USE FOR DETECTION OF *HISTOPLASMA CAPSULATUM* AND HISTOPLASMOSIS

(75) Inventors: Clayton H. Johnson, Little Rock, AR (US); Joan E. McEwen, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 412 days.

(21) Appl. No.: 10/718,955

(22) Filed: Nov. 21, 2003

Related U.S. Application Data

(60) Provisional application No. 60/428,135, filed on Nov. 21, 2002.

(51) Int. Cl.
*C12Q 1/68* (2006.01)
*C12P 19/34* (2006.01)
*C07H 21/04* (2006.01)

(52) U.S. Cl. .......................... 435/6; 435/91.1; 435/91.2; 536/23.1; 536/23.7; 536/24.1; 536/24.3; 536/24.32

(58) Field of Classification Search .................... None
See application file for complete search history.

(56) References Cited

U.S. PATENT DOCUMENTS

| 4,946,777 A | 8/1990 | Laméris et al. |
| 5,242,800 A | 9/1993 | Jimenez et al. |
| 5,324,632 A | 6/1994 | Weisberg et al. |
| 5,352,579 A | 10/1994 | Milliman |
| 5,360,732 A | 11/1994 | Berka et al. |
| 5,360,901 A | 11/1994 | Berka et al. |
| 5,580,971 A | 12/1996 | Mitsuhashi |
| 5,693,501 A | 12/1997 | Lee et al. |
| 5,707,802 A | 1/1998 | Sandhu et al. |

(Continued)

FOREIGN PATENT DOCUMENTS

EP    0272009    6/1988

(Continued)

OTHER PUBLICATIONS

Ampel, "Emerging Disease Issues and Fungal Pathogens Associated with HIV Infection," Emerg. Infect. Dis., 2:109-116, 1996.

(Continued)

*Primary Examiner*—Ram R. Shukla
*Assistant Examiner*—Sarae Bausch
(74) *Attorney, Agent, or Firm*—Kilpatrick Stockton LLP

(57) ABSTRACT

The present invention describes *Histoplasmosis capsulatum* chitin synthase nucleic acid and protein sequences as reagents for the detection of *H. capsulatum* infection. Specifically, the invention describes intron sequences from the *H. capsulatum* chitin synthase gene which can be used for hybridization-based and PCR-based detection of *H. capsulatum* infection. In another embodiment, assays for *H. capsulatum* chitin synthase 2 polypeptide and/or mRNA used as a diagnostic test for *H. capsulatum* infection and/or histoplasmosis. Also described is the differentiation of *H. capsulatum* from *Blastomyces dermititidis* based on detection of intron 1 sequences specific to *H. capsulatum* chitin synthase 2. The present invention also comprises the production of *H. capsulatum* strains lacking functional chitin synthase 2 as a means to produce *H. capsulatum* having reduced pathogenicity.

11 Claims, 17 Drawing Sheets

U.S. PATENT DOCUMENTS

| | | | |
|---|---|---|---|
| 5,763,169 | A | 6/1998 | Sandhu et al. |
| 5,919,617 | A | 7/1999 | Bhattacharjee et al. |
| 5,994,066 | A | 11/1999 | Bergeron et al. |
| 5,997,912 | A | 12/1999 | Schlesinger et al. |
| 6,001,564 | A | 12/1999 | Bergeron et al. |
| 6,117,641 | A | 9/2000 | Berlin et al. |
| 6,180,339 | B1 | 1/2001 | Sandhu et al. |
| 6,228,575 | B1 | 5/2001 | Gingeras et al. |
| 7,052,837 | B2 | 5/2006 | Johnson et al. |

FOREIGN PATENT DOCUMENTS

| | | |
|---|---|---|
| WO | WO 96/21741 | 7/1996 |
| WO | 804619 | 11/1997 |
| WO | WO 98/46738 | 10/1998 |
| WO | WO 99/54508 | 10/1999 |
| WO | WO 99/55874 | 11/1999 |

OTHER PUBLICATIONS

Altschul, S., "Basic Local Alignment Search Tool," J. Mol. Biol., 215: 403-410, 1990.

Ausubel, F.M. et al., Short Protocols in Molecular Biology, 4th Ed., Chapter 2, John Wiley & Sons, N.Y.

Beaman, B. L. et al., "Purification and Properties of a Unique Superoxide Dismutase from Nocardia Asteroides," J. Bio. Chem., 258:91-96, 1983.

Bird, R. et al., "Single-Chain Antigen-Binding Proteins," Science, 242:423-426, 1988.

Broaddus et al., "Bronchoalveolar Lavage and Transbronchial Biopsy for the Diagnosis of Pulmonary Infections in the Acquired Immunodeficiency Syndrom," Ann. Intern. Med., 102(6):747-752, Jun. 1985.

Brummer et al., "Antifungal Mechanisms of Activated Murine Bronchoalveolar or Perotoneal Macrophages for *Histoplasma capsulatum*," Clin. Exp. Immunol., 102(1):65-70, Oct. 1995.

Bullock, W. E. et al., "Role of the Adherence-Promoting Receptors, CR3, LFA-1, and p150,95, in Binding of *Histoplasma capsulatum* by Human Macrophages," Journal of Experimental Medicine, 165:195-210, 1987.

Castro et al., "1993 Revised Classification System for HIV Infection and Expanded Surveillance Case Definition for AIDS among Adolescents and Adults," MMRW 41:1-14, 1992.

Chomczynski, P. et al., "Single-Step Method of RNA Isolation by Acid Guanidinium Thiocyanate-Phenol-Chlorofrom Extraction," Anal. Biochem., 162-156-159, 1987.

Church, G.M. et al., "Genomic Sequencing," Proc. Natl. Acad. Sci., USA, 81:1991-1995, 1984.

Cockerill , F.R. et al., "Rapid-Cycle Real-Time PCR : a Revolution for Clinical Microbiology," ASM News, 68:77-83, 2002.

Cohen et al., "Sequence of the Saccharomyces Cerevisiae CTA 1 Gene and Amino Acid Sequence of Catalase A Derived from It," Eur. J. Biochem., 176(1):159-163, Sep. 1988.

Cohen et al., "Isolation of the Catalase A Gene of Saccharomyces Cerevisiae by Complementation of the ctal Mutation," Mol. Gen. Genet., 200(1):74-79, 1985.

Corpet, F., "Multiple Sequence Alignment with Hierarchical Clustering," Nucl. Acids Res. 16(22), 10881-10890, 1988.

Crowele, A. J. et al., "Evidence that Vesicles Containing Living, Virulent Mycobacterium Tuberculois or Mycobacterium Avium in Cultured Human Macrophages Are Not Acidic," Infect. Immun., 59:1823-1831, 1991.

Davies et al., "Disseminated Histoplasmosis in Immunologically Suppressed Patients," Am. J. Med., 64:94-100, 1978.

Deepe, G. S., "The Immune Response to *Histoplasma capsulatum*: Unearthing Its Secrets," J. Lab. Clin. Med., 123:201-205, 1998.

DeGroote, M. A. et al., "Periplasmic Superoxide Dismutase Protects Salmonella from Products of Phagocyte NADPH-Oxidase and Nitric Oxide Synthase," Proc. Natl. Acad. Sci. (USA), 94:13997-14001, 1997.

Deretic, V. et al., "Mycobacterium Tuberculosis Phagosome," Mol. Microbiol., 31:1603-1609, 1999.

Desai et al., "Killing of *Histoplasma capsulatum* by Macrophage Colony Stimulating Factor-Treated Human Monocyte-Derived Macrophages: Rols for Reactive Oxygen Intermediates," J. Med. Microbiol., 43(3):224-229, Sep. 1995.

Eissenberg, L. G. et al., "The Interplay between *Histoplasma capsulatum* and Its Host Cells," vol. 1, Ch. 6, W. B. Saunders Company, Ltd. London, UK, 1994.

Eissenberg, L. G. et al., "*Histoplasma capulatum* Modulates the Acidification of Phagolysosomes," J. Exp. Med., 177:1605-1611, 1993.

Evard et al., "The Cyanelle Genome of *Cyanophora paradoxa*, Unlike the Chloroplast Genome, Codes for the Ribosomal L3 Protein," Nucleic Acid Res., 18:1115-1119, 1990.

Fang, F. C. et al., "Virulent *Salmonella typhimurium* Has Two Periplasmic Cu, Zn-Superoxide Dismutases," Proc. Natl. Acad. Sci. (USA), 96:7502-7507, 1999.

Frugoli, J. A. et al., "Catalase Is Encoded by a Multigene Family in *Arabidopsis thaliana* (L.) Heynh," Plant Physiol., 112:327-336, 1996.

Frugoli, J. A. et al., "Intron Loss and Gain during Evolution of the Catalase Gene Family in Angiosperms,"Genetics, 149:355-365, 1998.

Garcia, E. et al., "Molecular Characterization of KatY (Antigen 5), a Thermoregulated Chromosomally Encoded Catalase-Peroxidase of *Yersinia Pestis*,"J. Bacteriol., 181:3114-3122, 1999.

George et al., "Radioimmunoassay: A Sensitive Screening Test for Histoplasmosis and Blastomycosis," Am. Rev. Respir. Dis., 124(4):407-10, Oct. 1981.

Goffeau, A. et al., "Life with 6000 Genes," Science, 274:563-567.

Goodwin, R. A. et al., "Histoplasmosis in Normal Hosts," Medicine (Baltimore), 60:231-266, 1981.

Goodwin, R. A., Jr. et al, "Disseminated Histoplasmosis: Clinical and Pathalogic Correlations," Medicine, 59:1-33, 1980.

Guan, L. et al., "Molecular Evolution of Maize Catalases and Their Relationship to Other Eukaryotic and Prokaryotic Catalases," J. Mol. Evol., 42:570-579, 1996.

Hamilton, A.J. et al., "Evidence That the M Antigen of *Histoplasma capsulatum* var. Capsulatum Is a Catalase Which Exhibits Cross-Reactivity with Other Dimorphic Fungi," J. Med. Vet. Mycol., 28:479-485, 1990.

Hansen et al., "Functional Complementation of Catalase-Defective Peroxisomes in a Methoylotrophic Yeast by Import of the Catalase A from *Saccharomyces cerevisiae*," Eur. J. Biochem., 184(1):173-179, Sep. 1989.

Hartman, P. et al., "Immunological Defense Mechanisms in Tuberculosis and MAC-Infection," Diag. Microbiol. Infect. Dis., 34:147-152, 1999.

Henikoff, S. et al., "Amino Acid Substitution Matrices from Protein Blocks," Proc. Natl. Acad. Sci. USA, 89, 10915-10919, 1992.

Hochman et al., "Purification and Characterization of a Catalase-Peroxidase and a Typical Catalase from the Bacterium *Klebsiella Pneumoniae*," Biochim. Biophys. Act, 1077(3):299-307, Apr. 1991.

Howard, "Studies on the Catalase of *Histoplasma capsulatum*," Infect. Immun., 39(3):1161-1166, Mar. 1983.

Howard, "Comparative Sensitivity of *Histoplasma capsulatum* Conidiospores and Blastospores to Oxidative Antifungal Systems," Infect. Immun., 32(1):381-387, Apr. 1981.

Izawa et al., "Importance of Catalase in the Adaptive Response to Hydrogen Peroxide: Analysis of Acatalasaemic *Saccharomyces cerevisiae*," Biochem. J, 320(Pt.1):61-67, Nov. 15, 1996.

Jacoboson et al., "Reevaluation of Diagnostic Histoplasma Serologies," Am. J. Med. Sci., 281(3): 143-51, Jun. 1981.

Jeavons, L. et al. "Identification and Purification of Specific *Penicillium marneffei* Antigens and Their Recognition by Human Immune Sera," J. Clin. Microbiol., 36:949-954, 1998.

Johnson, C. et al., "The Catalase Isozymes and Genes of Histoplasma Capsulatum," Abstract #361, XXi Fungal Genetics Conference, at http://www.fgsc.net/fungalgenetics2001/generaga, htm, Asilomar, CA, Mar. 2001.

Johnson, C. et al., "Investigation of the Catalase Enzyme of Histoplasma Capsulatum," Fed. Res. Prog., Abstract 0001:598, Jan. 1997.

Johnson et al., "Differentially Expressed Catalase Genes in Histoplasma Capsulatum," Abstact F-65, Abstracts of the General Meeting of the Amer. Soc. Microbiol., 98:263-64, 1998.
Johnson, C. H. et al., "Redunancy, Phylogeny and Differential Expression of *Histoplasma capsulatum* Catalases," Microbiology, 148:1129-1142, 2002.
Johnson, C. et al., "Catalase Isozymes and Genes of *Histoplasma capsulatum*," Abstract I-73, Abstracts of the Amer. Soc. for Microbiol., 100:397, 2000.
Johnson, C. H. et al., "Isolation of a *Histoplasma capsulatum* cDNA the Complements a Mitochondrial NAD(+)-Isocitrate Dehydrogenase Subunit I-Deficient Mutant of *Saccharomyces cereviasiae*," Yeast, 15:799-804, 1999.
Johnson, et al., "Characterization of the Differentially Expressed Catalase Isozymes and Genes of *Histoplasma Capsulatum*," Abstract of the General Meeting of the Amer. Soc. Microbiol., 99:298-299, 1999.
Johnson, C.H. et al., "The psbB Gene Cluster of the *Chlamydomonas reinhardtii* Chloroplast: Sequence and Transcriptional Analysis of psbN and psbH," Plant Mol. Biol., 22:645-658, 1993.
Johnson, S. M. et al., "Preparation and ELISA Evaluation of *Blastmyces dermatitidis* Yeast Phase Lysate Antigens," Diagn. Microbiol. Infect. Dis., 11(2):81-86, Oct. 1998.
Kamei et al., "Induction of Stress Protein Synthesis in *Histoplasma capsulatum* by Heat, Low pH and Hydrogen Peroxide," J. Med. Vet. Mycol., 30(5):385-393, 1992.
Kasuga, T. et al., "Phylogenetic Relationships of Varieties and Geographical Groups of the Human Pathogenic Fungus *Histoplasma capsulatum* Darling," J. Clin. Micro., 37:653-663, 1999.
Kawasaki et al., "Two Divergent Catalase Genes Are Differentially Regulated during *Aspergillus nidulans* Development and Oxidative Stress," J. Bacteriol., 179(10):3284-3292, May 1997.
Keath et al., "Typing of *Histoplasma capsulatum* by Restriction Fragment Lenght Polymorphisms in a Nuclear Gene," J. Clin. Microbiol., 30(8):2104-2107, Aug. 1992.
Kersulyte et al., "Diversity among Clinical Isolates of *Histoplasma capsulatum* Detected by Polymerase Chain Reaction with Arbitrary Primes," J. Bacteriol., 174(22):7075-7079, Nov. 1992.
Klein, et al., "Isolation, Purification, and Radiolabeling of a Novel 120-kD Surface Protein on *Blastomyces dermatitidis* Yeasts to Detect Antibody in Infected Patients," J. Clin. Invest., 85(1):152-161, Jan. 1990.
Klotz, M. G., "Catalase Genes Are of Bacterial Origin and Have Evolved in Eukaryotes by Intron Acquisition," American Society for Microbiology, 101st Annual Meeting, Abstract H-18, 2000.
Klotz, M. G., "On the Molecular Evolution of Catalatic Hydroperoxidases," University of Louisville, KY and University of Manitoba , Winnipeg, MB, Canada.
Klotz, M. G. et al., "Phylogenetic Relationships among Prokaryotic and Eukaryotic Catalases," Mol. Biol. Evol., 14:951-958, 1997.
Kragler et al., "Two Independent Peroxisomal Targeting Signals in Catalase A of *Saccharomyces cerevisiae*," J. Cell. Bio., 120(3):665-673, Feb. 1993.
Kurita, N. et al., "Resistance of *Histoplasma capsulatum* to Killing by Human Neutrophils," Mycopathologia, 115:207-213, 1991.
Lardinois et al., "Characterization of Hydrogen Perioxide and Superoxide Degrading Pathways of *Aspergillus niger* Catalase: A Steady-State Analysis," Free Radic. Res., 20(1):29-50, Jan. 1994.
Leutenegger, C.M. et al., "Real-Time TaqMan PCR as a Specific and More Sensitive Alternative to the Branched-chain DNA Assay for Quantitation of Simian Immunodeficiency Virus RNA," AIDS Res. Hum. Retroviruses, 17:243-251, 2001.
Li. R-K et al., "In Vitro Activities of Voriconazole, Intraconazole, and Amphotericin B against *Blastomyces dermatitidis, Coccidioides immitis*, and *Histoplasma capsulatum*," Antimicrobial Agents and Chemotherapy, 44:1734-1736, 2000.
Li, et al., "Expression of katG in *Mycobaterium tuberculosis* Is Associated with Its Growth and Persistence in Mice and Guinea Pigs," J. Infect. Dis., 177:1030-1035, 1998.
Loewen, P.C. et al., "Catalase—and "Old" Enzyme That Continues to Surprise Us," ASM News, 66:76-82, 2002.
Lopez-Medrano, R., "An Immunodominant 90-Kilodalton *Aspergillus fumigatus* Antigen Is the Subunit of a Catalase," Infection & Immunity, 63:4774-4780, 1995.
Ma et al., "Bacterioferritin A Modulates Catalase A (KatA) Activity and Resistance to Hydrogen Peroxide in *Pseudomonas aeruginosa*," J. Bacteriol., 181(12):3730-3742, Jun. 1999.
Mangala, A.N. et al., "Determination of Bacterial Load by Real-time PCR Using a Broad-Range (universal) Probe and Primers Set," Microbiology 148, 257-266, 2002.
Marchler, G. et al., "A *Saccharomyces cereviisiae* Element Controlled by Protein Kinase A Activates Transcription in Response to a Variety of Stress Conditions," UAS EMBO Journal, 12:1997-2003, 1993.
Maresca et al., "Morphological Transitiion in the Human Fungal Pathogen *Histoplasma capsulatum*," Trends Microbiol., 2:110-114, 1994.
Maresca, B. et al., "Respiration in the Yeast and Mycelial Phases of *Histoplasma capsulatum*," Journal of Bacteriology, 138:647-649, 1979.
Miyashiro et al., "Immunofluorescent Detection of *Histoplasma capsulatum* in Primate Experimental Ocular Histoplasmosis," Curr. Eye. Res., 5(11):833-840, Nov. 1986.
Munro, C. A. et al., "Chitin Synthesis in Human Pathogenic Fungi," Medical Mycology, 39 (S1), 41-53, 2001.
Murray, et al., "Nucleotide Sequence of Peroxisomal Catalase from the Yeast *Candida Tropicalis* pK223; Identification of an Upstream BamH1 Site Polymorphism," Nucleic Acids Res., 17(9):3600, May 1989.
Murray, et al., "The Nucleotide Sequence of Complementary DNA and the Deduced Amino Acid Sequence of Peroxisomal Catalase of the Yeast *Candida tropicalis* pK223," Gene, 61(3):401-413, 1987.
Nadkarni, M.A. et al., "Determination of Bacterial Load by Real-Time PCR Using a Broad-Range (Universal) Probe and Primers Set," Microbiology, 148:257-266, 2002.
Navarro et al., "Posttranscriptional Control Mediates Cell Type-Specific Localization of Catalase A During *Aspergillus nidulans* Development," J. Bacteriol., 180(21):5733-5738, Nov. 1998.
Newman, S. L. et al., "Phagocytosis of *Histoplasma capsulatum* Yeasts and Microconidia by Human Cultured Macrophages and Alveolar Macrophages," Journal of Clinical Investigation, 85:223-230, 1990.
Newman, S. L. et al, "Digestion of *Histoplasma capsulatum* Yeasts by Human Macrophages," J. Immunol., 149:574-580, 1992.
Newman, S. L. et al., "Human Neutrophil-Mediated Fungistasis Against *Histoplasma capsulatum*," J. Clinical Investigation, 92:624-631, 1993.
Newman, S. L., "Macrophages in Host Defense Against *Histoplasma capsulatum*," Trends Microbiol., 7:67-71, 1999.
Okada et al., "Catalase Gene of Yeast *Candida tropicalis*: Sequence Analysis and Comparison with Peroxisomal and Cytosolic Catalases from Other Sources," Eur. J. Biochem., 170(1-2):105-10, Dec. 1987.
Padhye et al., "Comparative Evaluation of a Chemiluminescent DNA Probe and an Exoantigen Test for Rapid Identification of *Histoplasma capsulatum*," J. Clin. Microbiol., 30(12):3108-3111, Dec. 1992.
Patriarca, E. J. et al., "Mitochondrial Activity and Heat-Shock Response During Morphogenesis in the Pathogenic Fungus *Histoplasma capsulatum*," Biochemistry & Cell Biology, 70:207-214, 1992.
Pitkin, J. W., et al., "A Putative Cyclic Peptide Efflus Pump Encoded by the TOXA Gene of the Plant-Pathogenic Fungus *Cochliobolus carbonum*," Microbiology, 142:1557-1565, 1996.
Radcliff et al., "Catalase, a Novel Antigen for *Helicobacter pylori* Vaccination," Infect. Immun., 65(11):4668-4674, Nov. 1997.
Rambukkana, A. et al., "Identification of a Novel 17-kDA Protein from Mycobacterium Tuberculosis Culture Fluid by a Monoclonal Antibody Specific for the Mycobacterium Tuberculosis Complex," Scand. J. Immunol., 37:471-478, 1993.
Raynaud, C. et al., "Extracellular Enzyme Activities Potentially Involved in the Pathogenicity of Mycobacterium Tuberculosis," Microbiology, 144;577-587, 1998.

Reid et al., "Direct Detection of *Histoplasma capsulatum* in Soil Suspensions by Two-Stage PCR," Mol. Cell. Probes, 13(4):269-273, Aug. 1999.
Reiss, et al., "Non-Culture Based Diagnostic Tests for Mycotic Infections," Med. Mycol., 38(1):147-159, 2000.
Rouse, D. A. et al., "Molecular Mechanisms of Isoniazid Resistance in *Mycobacterium tuberculosis* and Mycobacterium Bovis," Infect. Immun., 63:1427-1433, 1995.
Sambrook, et al., "Molecular Cloning: A Laboratory Manual," Cold Spring Harbor Laboratory Press, 1989, Chapter 9.
Schaffner, A. et al., "In Vitro Susceptibility of Fungi and Killing by Neutrophil Granulocytes Discriminates between Primary Pathogenicity and Opportunism," J. Clin. Invest., 78:511-524, 1986.
Schaffner, A. et al., "Killing of *Aspergillus* Spores Depends on the Anatomical Source of the Macrophage," Infect. Immun., 42:1109-1115, 1983.
Schaffner, A. et al., "Selective Protection against Conidia by Mononuclear and against Mycelia by Polymorphonuclear Phagocytes in Resistance to *Aspergillus*," J. Clin. Invest., 69:617-631, 1982.
Scherr, G. H. et al., "Studies on the Dimorphism of *Histoplasma capsulatum*," Exp. Cell Res., 12:92-107, 1957.
Scherr & Weaver, "The Dimorphism Phenomenon in Yeasts," Bact. Rev., 17:51-92, 1953.
Schnur, R. A. et al., "The Respiratory Burst Reponse to *Histoplasma capsulatum* by Human Neutrophils," Journal of Immunology, 144:4765-4772, 1990.
Sherman, D. R. et al., "Compensatory ahpC Gene Expression in Isoniazid-Resistant *Mycobacterium tuberculosi*," Science, 272:1641-1643, 1996.
Sonnenberg, M. G. et al., "Definition of Mycobacterium Tuberculosis Culture Filtrate Proteins by Two-Dimensional Polyacrylamide Gel Electrophorsis, N-Terminal Amino Acid Sequencing, and Electrospray Mass Spectrometry," Infect. Immun., 65:4515-4524, 1997.
Spiegelhalder, C. B. et al., "Purification of *Helicobacter pylori* Superoxide Dismutase and Cloning and Sequencing of the Gene," Infect. Immun., 61:5315-5325, 1993.
Spitzer et al., "Use of Mitochondrial and Ribosomal DNA Polymorphisms to Classify Clinical and Soil Isolates of *Histoplasma capsulatum*," Infect. Immun., 57:1409-1412, May 1989.
Stein, D.K. et al., "Fungal Infections in the Immunocompromised Host," Diagn. Microbiol., Infect., Dis., 12:221S-228S, 1989.
Storz, G. et al., "OxyR: A Regulator of Antioxidant Genes," J. Nutr., 122:627-30, 1992.
Storz, G. et al., "The OxyR Regulon," Antonie Van Leeuwenhoek, 58:157-161, 1990.
Storz, G. et al., "Transcriptional Regulator of Oxidative Stress-Inducible Genes: Direct Activation by Oxidation," Science, 248:189-194, 1990.
Storz, G. et al., "Bacterial Defenses against Oxidative Stress," Trends Genet., 6:363-368, 1990.
Strasser, J. E. et al., "Regulation of the Macrophage Vacuolar ATPase and Phagosome-Lysosome Fusion by *Histoplasma capsulatum*," J. Immunol., 162-6148-6154, 1999.
Sturgill-Koszycki, S., et al., "Lack of Acidification in Mycobacterium Phagosomes Produced by Exclusion of the Vesicular Proton-ATPase," Science, 263:678-681, 1994.
Thomson, J. M. et al., "pMECA: A Cloning Plasmid with 44 Unique Restriction Sites that Allows Selection of Recombinants Based on Colony Size," Biotechniques, 24, 922-927, 1998.
Thompson, J.D. et al., "CLUSTAL W: Improving the Sensitivity of Progressive Multiple Sequence Alignment through Sequence Weighting, Position-Specific Gap Penalties and Weight Matrix Choice," Nucleic Acids Res., 22:4673-4680, 1994.
Vera-Cabrera, L. et al., "Distribution of a *Nocardia Brasiliensis* Catalase Gene Fragment in Members of the Genera *Nocardia, Gordona*, and *Rhodococcus*," J. Clin. Microbiol., 37:1971-1976, 1999.
Wall, S.J et al., "Quantitive Reverse Transcription—Polymerase Chain Reaction (RT-PCR): A Comparison of Primer-Dropping, Competitive, and Real-time RT-PCRs," Anal. Biochem., 300:269-273, 2002.
Wheat et al., "Risk Factors for Disseminated or Fatal Histoplasmosis," Ann. Intern. Med., 96:159-163, 1982.
Wheat et al., "Histoplasmosis in the Acquiered Immune Deficiency Syndrome," Am. J. Med., 78:203-210, 1985.
Wilson, T. M. et al., "Effect of inhA and katG on Isoniazid Resistance and Virulence of *Mycobacterium bovis," Mol. Microbiol.*, 15:1009-1015, 1995.
Woods et al., "Fast DNA Isolation from *Histoplasma capsulatum*: Methodology for Arbitrary Primer Polymerase Chain Reaction-Based Epidemiological and Clinical Studies," J. Clin. Microbiol., 31(2):463-464, Feb. 1993.
Woods, J.P. et al., "InVivo Generation of Linear Plasmids with Addition of Telomeric Sequences by *Histoplasma capsulatum*," Molecular Microbiology, 6:3603-3610, 1992.
Worsham, P.L. et al., "Quantitive Plating of *Histoplasma capsulatum* Without Addition of Conditioned Medium or Siderophores," J. Med. & Veterinary Mycology, 26:137-143, 1998.
Zamocky et al., "Site-Directed Mutagenesis of the Lower Parts of the Major Substrate Channel of Yeast Catalase A Leads to Highly Increased peroxidatic Activity," FEBS Lett., 367(3):241-245, Jul. 1995.
Zancope-Oliveria et al., "Molecular Cloning, Characterization, and Expression of the M Antigen of *Histoplamsa capsulatum*," Infect. Immun., 67(4):1947-1953, Apr. 1999.
Bowen, A.R. et al., "Classification of Fungal Chitin Synthases," Proc. Natl. Acad. Sci., vol. 89, p. 519-523, 1992.
Popolo, L. et al., "Increase in Chitin as an Essential Response to Defects in Assembly of Cell Wall Polymers in the *gpp1* Δ Mutant of *Saccharomyces carevisiae*," Journal of Bacteriology, vol. 179, No. 2, p. 463-469, 1997.
Wang, Z. et al., "*WdCHS3*, a Gene That Encodes a Class III Chitin Synthase in *Wangiella* (*Exophiala*) *dermatitidis*, Is Expressed Differently under Stress Conditions," Journal of Bacteriology, vol. 182, No. 4, p. 874-881, 2000.
Wang, Z. et al., "WdChs2p, a Class I Chitin Synthase, Together with WdChs3p (Class III) Contributes to Virulence in *Wangiella* (*Exophiala*) *dermatitidis*," Infection and immunity, vol. 69, No. 12, p. 7517-7526, 2001.

SEQ. ID NO: 9

```
   1 CGCAAATCAG CAACTGATCC GACCGCACGA TGATGGCCCA TCGACGCTTC
  51 CCCCTGTGCA GATGATGTTC TGCTTGAAAC AAAAGAACAG TAAGAAAATC
 101 AACTCTCACA CATCGCTGTT CAATGCCTTT GGCCGAATCC TCAACCCGGA
 151 AATCTGCATC TTGCTCGACG CGGGTACGAA GCCGGGTCAT AAATCCCTCC
 201 TGGCACTGTG GGAAGCCTTC TATAACGACA AGATCTGGG CGGCTCGTGC
 251 GGCGAAATCC ACGCTATGTT GGGCAAAGGC TGGAAAAACC TCATCAACCC
 301 TCTTGTTGCA GCGCAAAACT TCAATACAA AATCAGTAAC ATCCTGGATA
 351 AACCTCTGGA ATCCTCCTTC GGCTACGTCA GCGTGTTGCC CGGTGCCTTC
 401 TCTGCCTACC GCTTCCGTGC AATCATGGGC AGACCTCTCG AACAGTACTT
 451 CCACGGTGAC CATACACTCT CCAAACAACT CGGTCCCAAG GGTATCGAGG
 501 GCATGAACAT TTTCAAGAAG AACATGTTCT GGCCGAGGA TCGGATTCTG
 551 TGTTTCGAAC TCGTGGCCAA GGCCGGGTCC AAATGGCATC TGTCCTACGT
 601 CAAGTCGTCC AAGGGCGAGA CTGACGTGCC CGAGGGAGCC CCCGAATTCA
 651 TCGCCAGCG TCGTCGGTGG CCAACGGCT CGTTCGCAGC TAGTATCTAC
 701 TCATTGATGC ATTTTGGCCG AATGTATAAG AGCGGCCATA ACCTTCTGCG
 751 CATGTTCTTT TTCCATATTC AGATGATCTA CAATACGTGC ACCGTTATCA
 801 TGACTTGGTT TGCGCTTGCT TCATACTGGC TCACAACTTC CGTCATCATG
 851 GACCTCGTCG GAAACCCTCC CGCTCCAGAA TCTGGCAGCA CGCAGAGGGC
 901 ATTCCCATTC GGCAATACCG CCACTCCGAT TGTCAACACT GTTCTGAAGT
 951 ACTTGTATCT GGCCTTCCTG CTCTTGCAGT TTATTTTGGC TTTGGGTAAC
1001 CGGCCTAAAG GATCTAAACA CTCGTACATC ACCTCCTTCG TCGTATTCGG
1051 CATTATCCAA TTGTACATCA TTGTCTTATC CATGTACCTC GTCGTCCGCG
1101 CCTTCAGCGG TGGCACACTC GCCTTCACAA CAGACAAAAG TATCGGCGAA
1151 TTCCTCAAGT CCTTCTTCAG TTCCGAAGGA CCGGGAATCA TCATCATCGC
1201 CCTCGCCGCT ACCTTCGGCC TATATTTCGT CGCTTCTTTC ATGTACCTTG
1251 ACCCTTGGCA CATGTTCACC TCCTTCCCGG CCTACCTCCT GATCATGTCC
```

FIG. 1A

```
1301  TCGTACATCA ACATCCTGAT GGTCTACGCC TTCAGCAACT GGCACGATGT
1351  GTCGTGGGGC ACAAAGGGTG CGGACAAAGC CGACGCTCTG CCCTCTGCCC
1401  AAACGCAAAA GGAAGACGAC GGCAAAGCTG CTGTGATCGA GGAGATCGAC
1451  AAGCCGCAGG CGGATATCGA CACCCACTTT GAAACCACTG TGAACCGTGC
1501  GCTGACGCCG TACGTGGAGC CAAAGGTGAA GGAGGGGAAG TCGCTAGATG
1551  ATTCGTATAA GAGTTTCCGC ACGCGGTTGG TGACGCTATG GCTGTTTTCG
1601  AATGGCATTC TTGCCGTGGC CATTACCAGC GAGGATGTGA ACAAGTTTGG
1651  ATTCACGTCC CGAGCAACCA GCCGAACCAC GCATTCTTC CAGGCTCTCC
1701  TTTGGGCGAC CGCAGCGCTC TCCCTCATCC GCTTCACCGG CGCATGCTGG
1751  TTCCTTGGCC GGACTGGAAT TATGTGCTGC TTCGCGAGAA GATAGTCAGT
1801  CCATTTGGCT CTGGATTTTC TATATATTTT GTTGGTGAT GCAAAAATCT
1851  TTTGCTTCCC TTTTTCCTTT TCTCTTTCGG GTGACCTTTT TGTTGCGGGC
1901  GACGGCACGA AACCCGGAAT AATATAAGAC AAGGATGGGG GAGAAGAGAG
1951  CATGAAGATC GAAGATCGAA AGTCGAAAGT CGAAAATTGA AAGGAGAAGA
2001  AAGGAAATGA CAAGAAACTG GCAGCTGCCG CTTGGCCAAC TGTTGGAAAG
2051  TTTTTCTTTT GCATTTCTAT GAATATGTCC CGATTTGTT TTTCTTTTCC
2101  CATTGCTTGT TGTTCTTTTC GCTTTTTTCG ATTCCTTTCC TATAATAATG
2151  GCAAGATGTG TCCTATTTCC TCCTGCCTGG CCTCTCTTTT GTGTGTTTCT
2201  ATATGCGTGA GAGCCTCTGA ATTCCGAATC TAATGTTCTG TTTGTTGTCT
2251  T
```

FIG. 1B

SEQ ID NO: 10

```
TGCTTTTTTGAAGGTTCCTACCCTTAGCCCAAAGTCCGGCTTTCCNCTTNT
TTTCTTTTTTTCTTTTTGGACNAGGACCATGGATCCCCCCCCCATNCATCG
GGTCCNGAGAGAAGATGGTCCAAATATTCTTAAACTATCTTGATCCCTTGT
AACCCAATGTCCCCAATCGGCTTCCCAAAATTGGCCAACAATTCCAATTTC
NACCCCCACNAGCGGGAGTAATGGAGCAACNATGCAAACCCGAACCCCNA
TGCAACGGTTCCCCAAAAAGCCACCCCTCTGAACAGTGATTGACAAATCGG
TGCAAGGCATTGCTCACGGGGTACTCACCTGAACAATCGACACGGCATAAA
TGTTGGTGGATGGCAAGACAATTAATTCATCTTCATTGAGCTTTATTTGTT
TATTCCCAGCCATTCACAAAAACCAAAAGTCCAAAATTCCAAAAATCAGGG
CTTGGTTTTGCCTCCCCATTTTGGCCCTGAATAACGGGAAGGTTAGTTACA
TAGTAAAAGTAAAACCGTGTTAACAAAAGTTTCGAGGATCGCAACCAGAC
AAATTGGACCAGGATCTCTTGACTTCCCGTCTTTCGGCTAAGAATAGACTT
TTTTTGGGGCAACGAAATTCTGGTACAACTTTTGATTTCTGGCGGGTTTCA
GATATGTGGGGACATTATCGGGAATGATAAATTTTTTTTTTTTTTTTTTTG
GACTGCTCTCAAACTCATGTGATAATATCACAGACAATAGGTATCGCAAGC
GAGCATCTTGACTTGACTGCTGAGAAGTGATCTTGTCGCTGCAATTGGTGG
AGGCGACTAACAGACGAACAGCCTCGCAGGATGCATGCATGAATACAGCAA
GTCGCTGCAGAGGTCATCACATTATGATGTCCTCCACGCCCGTTTTCCTTC
CTTCAGATACACCCATCCATCCATATGCATATACATATACATATACATATG
TGTCGTGATGTGACGGTGCCGCGCGCAGTATGAATGATTCGCTGCCTCTAA
GTATGGACAAGTAAGTATGTACTGTACATATACGTATGTCTGTCTGTCTG
TCTGTCTGTCTGTCTGTATGCAGTCCAACTGTGGACAAAGCCCTCGCGGCA
ACGTTCAAAGCGGCGAGACAAGAGAAGAAGGTGAAATTAAACTGAGTAGAT
GGCAGAATCGCCGCCATGTCTCCCTTTCCTTCCGGCTAGAGGAGGCAGAGG
AAAGGCTGATTGAGCGAGTGGGGGGAGCATTATTTATCCACCCTGAGCTGG
GCTGGGCCTGGGCGGAGAGTACCATTGAGTAGAGTTGTGAACTGTCGGTCT
ATGCTCGATGGAAGCAACGTACCTGGCTTACCTGGCTCACCTGGTTGGAAA
TCCAAACGGCGAGTATATATCCATATCCCAGATATGTGCGCATGTTGAATG
GTGGCGATTAATCGGATGTCCATGTCATTCTCCTTTCTCGGCAAAATATAT
ATCTACCTACTTGTATGGTAATGTGTATCCCACCCTTACCAAACGCGGCTG
AACAAAGAAAGTTACGGTAAATTTCACGCTAGTACCCAGCCAGAAGCTGGG
TACGGCTCCTGTGCTCTGTACAGTCCGGCCATACCATACCATACCATACCG
TACCATACCGTACCATATCACGTTCATCCACCCGTTTGCCCCAAGAGAAA
TATCATCATCGCCTTTTCGGGCCTGTAGCTTACTTTCTTTTTTCCTATTTT
```

FIG. 2A

```
TTTCTTTTCTATTTCTATTTCTATTTCTATTTCTATTTCGCTGCTTATTAT
TCTCGCCTGTTGGTCTTGTCCAGCAAGCCTGGGAATATCAAGCGCTCGTCT
GTGGTTTGTTTTTATCCGTTGCCCTGCTTTGTGTCCCGCTGCCCCCTTAGC
TCCCTGTGGCTTCGCTGCCCCTAAAAAACAATCATCTTCTTCTTCCGCTG
CTCTGTTCTCGCTCGTCTCTCTTCTCTCTTCTCTTTTCTCTGCCTCTCTTC
CTCCTCTCGATCCATCCATCTATTCTCCCTCTATCCTTCTATCCGCTTCA
TCAACCCAGCCTCTCGTTTTGACGGCGGCCACAGCTCCCTCAT*CATGGCCT*
ATCCAGGCTCGAACTCTCCAGGGGGGTACGGCGATGGCCATCGACTCCATG
ACCTCCCATCTGGCAGCGTGAGAAACACTCTTTCCTATGTATATGCATAT
GATATAGATATAGATATAGGTATACATTTATATACATATATAAGAGAGCGT
GTGTGTCTGTGTGTGTGTCTGTTTTGTGTGTGTGTATCTGTCTGTATATAT
ATACACATCGATATATATATGCTTTTGGCTACGTATTCAAGCACTGGTTCC
CCCTGGTCGCGGGCCACGGTACCAGTGGTTTCAGGATGATATCCTCTCAAC
ACAGGAACCACCCCTTGCTAACTTGCCCCTTAAATCGCTCCAGCAATATAA
TCTTCCCGCCGAACACGATGCCTCCCAATCGCTCCTCCACCAAAACCAAGG
CCCATTCAGCGGCCCCTTTGATGACCCCAACACCACCACCGCGGTGGCTC
TCCTGTCCGATCCCCCTCCAGATACAGCCTGACAGAATCCTACGTAACCGA
CCATCCCCAAGCTCAAGACCACTACGGCGGCCAAATGGAAAATCCCGCCGC
TGGCTTTGGTGTTCCCGGTCGGGTTCCGTCCCCCTATACCCGCAGTGAGAC
CTCCTCCACGGAGGCCTGGCGTCAGCGACAGGCGCCCGGCAATCTGCGCCG
TTATGCCACCAGGAAAGTCAAACTTGTCCAAGGCTCTGTTCTCAGTGTCGA
TTATCCCGTTCCCAGTGCTATTCAGAATGCCGTGCAGGCTAAATACCGCAA
TGATCTCGAAGGTGGTAGTGAGGAATTCACTCATATGCGATGTAGGTTTTT
GTCCTTGATTTCTTTTTCTTTTACTCCCCTCTGCTTTGGTTTATGGTCGT
CTCCTTGCTGATTTGCTGCTGCCATCTTAGACACCGCCGCTACCTGTGATC
CCAACGAGTTCACTCTGCACAATGGGTACAATCTGCGCCCGGCGATGTATA
ACCGTCATACCGAACTGCTGATTGCTATTACCTATTACAATGAAGACAAAA
TGCTTACTTCGCGCACCCTGCACGGCGTAATGCAAATATCCGTGACATTG
TGAACCTCAAGAAGTCCGAGTTCTGGAACAAAGGTGGACCTGCTTGGCAGA
AAATCGTTGTCTGTCTGGTCTTCGATGGAATCGACCCTTGCGACAAAGACA
CCCTCGACGTGCTGGCCACAATTGGAATCTACCAGGATGGCGTGATGAAAA
AAGATGTCGATGGAAAGGAAACCATCGCCCACATTGTCAGTACATATGA
TACCCGTAGCCCAATTTTTTGCACCTTCTACTACTGCTACACTGTACTAAC
TTCCCGTCTAGTTTGAATACACCACCCAACTCTCAGTCACCGCAAATCAGC
AACTGATCCGACCGCACGATGATGGCCCATCGACGCTTCCCCCTGTGCAGA
```

FIG. 2B

```
TGATGTTCTGCTTGAAACAAAAGAACAGTAAGAAAATCAACTCTCACAGAT
GGCTGTTCAATGCCTTTGGCCGAATCCTCAACCCGGAAATCTGCATCTTGC
TCGACGCGGGTACGAAGCCGGGTCATAAATCCCTCCTGGCACTGTGGGAAG
CCTTCTATAACGACAAAGATCTGGGCGGCTCGTGCGGCGAAATCCACGCTA
TGTTGGGCAAAGGCTGGAAAAACCTCATCAACCCTCTTGTTGCAGCGCAAA
ACTTCGAATACAAAATCAGTAACATCCTGGATAAACCTCTGGAATCCTCCT
TCGGCTACGTCAGCGTGTTGCCCGGTGCCTTCTCTGCCTACCGCTTCCGTG
CAATCATGGGCAGACCTCTCGAACAGTACTTCCACGGTGACCATACACTCT
CCAAACAACTCGGTCCCAAGGGTATCGAGGGCATGAACATTTTCAAGAAGA
ACATGTTCTTGGCCGAGGATCGGATTCTGTGTTTCGAACTCGTGGCCAAGG
CCGGGTCCAAATGGCATCTGTCCTACGTCAAGTCGTCCAAGGGCGAGACTG
ACGTGCCCGAGGGAGCCCCCGAATTCATCGGCCAGCGTCGTCGGTGGCTCA
ACGGCTCGTTCGCAGCTAGTATCTACTCATTGATGCATTTTGGCCGAATGT
ATAAGAGCGGCCATAACCTTCTGCGCATGTTCTTTTTCCATATTCAGATGA
TCTACAATACGTGCACCGTTATCATGACTTGGTTTGCGCTTGGTATGTGTT
GTTCAACAATATAAGTCTTTGTTCCTCCGAACAATGACATCCCTCTTTCAA
CTTCCACTTTCTTCTTGCGTCTATTGTCTCCCAACACTAACATGTTCTAGC
TTCATACTGGCTCACAACTTCCGTCATCATGGACCTCGTCGGAAACCCTCC
CGCTCCAGAATCTGGCAGCACGCAGAGGGCATTCCCATTCGGCAATACCGC
CACTCCGATTGTCAACACTGTTCTGAAGTACTTGTATCTGGCCTTCCTGCT
CTTGCAGTTTATTTTGGCTTTGGGTAACCGGCCTAAAGGGTGAGTTTGCAT
AATCTCCTAGTCAACTAAGGGGAGCTTCAGAAATATCCAATTCGTGGCATT
GTTATTTTCATTGCCCTTCTCCCCGGCGAGATTCCCGGCGCTGAGCTCCGA
TATATGCGTTAGATGATACTGATAGCGCCCTCAGATCTAAACACTCGTAC
ATCACCTCCTTCGTCGTATTCGGCATTATCCAATTGTACATCATTGTCTTA
TCCATGTACCTCGTCGTCCGCGCCTTCAGCGGTGGCACACTCGCCTTCACA
ACAGACAAAGGTATCGGCGAATTCCTCAAGTCCTTCTTCAGTTCCGAAGGA
CCGGGAATCATCATCATCGCCCTCGCCGCTACCTTCGGCCTCTATTTCGTC
GCCTCTTTCATGTACCTTGACCCCTGGCACATGTTCACCTCCTTCCCGGCC
TACCTCCTGATCATGTCCTCGTACATCAACATCCTGATGGTCTACGCCTTC
AGCAACTGGCACGATGTGTCGTGGGGCACAAAGGGTGCGGACAAAGCCGAC
GCTCTGCCCTCTGCCCAAACGCAAAAGGAAGACGACGGCAAAGCTGCTGTG
ATCGAGGAGATCGACAAGCCGCAGGCGGATATCGACAGCCAGTTTGAAAGC
ACTGTGAAGCGTGCGCTGACGCCGTACGTGGAGCCAAAGGTGAAGGAGGGG
AAGTCGCTAGATGATTCGTATAAGAGTTTCCGCACGCGGTTGGTGACGCTA
TGGCTGTTTTCGAATGGCATTCTTGCCGTGGCCATTACCAGCGAGGATGTG
AACAAGTTTGGATTCACGGTAGGCCTTACTTTCCTTTTTTCCCCCTTCCTC
```

FIG. 2C

```
TTTTTTTTTTTTTCTTTCGCCTTTTGGGGAAAAAAAAAATAAAAAAATAA
AAACACTTTGCTAACGTGTTCCTCCCACAATCCAGTCCCGAGCAACCAGCC
GAACCACGCATTTCTTCCACGCTCTCCTTTGGGCGACCGCAGCGCTCTCCC
TCATCCGCTTCACCGGCGCATGCTGGTTCCTTGGCCGGACTGGAATTATGT
GCTGCTTCGCGAGAAGATAGTCAGTCCATTTGGCTCTGGATTTTCTATATA
TTTTGTTTGGTGATGCAAAATCTTTTGCTTCCCTTTTTCCTTTTCTCTTT
CGGGTGACCTTTTTGTTGCGGGCGACGGCACGAAACCCGGAATAATATAAG
ACAAGGATGGGGGAGAAGAGAGCATGAAGATCGAAGATCGAAAGTCGAAAG
TCGAAAATTGAAAGGAGAAGAAAGGAAATGACAAGAAACTGGCAGCTGCCG
CTTGGCCAACTGTTGGAAAGTTTTTCTTTTGCATTTCTATGAATATGTCCC
GATTTTGTTTTTCTTTTCCCATTGCTTGTTGTTCTTTTCGCTTTTTCGAT
TCCTTTCCTATAATAATGGCAAGATGTGTCCTATTTCCTCCTGCCTGGCCT
CTCTTTTGTGTGTTTCTATATGCGTGAGAGCCTCTGAATTCGAATCTAAT
GTTCTGTTTGTTGTCTTATTTCTCTGATCGTCCCCGCCCCTGGTGTTTTT
GTTGCTGCTGTTCTTGCTGTTACTGCTTTTTCTGTTTCTGGGTTTTTCCCT
TGTTGTGTAAATTTACTATATCCTACCTAGATGACTTTTTTTTTTTTATT
TTCTTTTTCGCTCTCCGCCTCTTCTGCAAATGATGTAGCTAATTGGCTGAT
ATGATTGGAATGAATTGAAGGCATTTACTTTTCGAATCCATTTATTGACGG
CTGTAGCCTGTAGCCTGTAGCCTTGTACTGCGTATGTACATGTATATTATG
GAGTTCACCCGCCAAACCACAGCTCGGGCCGTTGGGCAATCAGCCGTGTCA
CGTGCACTCGGCTCCCCTGCCCGATGCATCAGCGTCATTCCTCATCCTATC
CCCGTCTTGGAATCCTCCCAGGCCTCACTCCCCATCCGCCAACCTTTGCAC
AACGCCGTTACTCTGCACTCTGACTGCTTGTCCGTCGGCCCGCCCGTCAGC
CCTCGTTCCGCTCCCTTTCGGCCCCTTTTGTTTTGCCCCCTTCACGGTCC
CAAAAGAAATCTTATCTTATCACGGCACACCAACACCACTGTCTGTGTACT
GTACATGTACATACACACCCAGCCCCGCCTCGCATCTCAACGACAGCA
TAAACAACCCCAAGCCCAGTTCCACTTGGCTTCTCTTCCCCGTAGTTTGTG
TCCCGCTCTATCTCCCTCGGGCCTCCGTGCTTGGACCATAAACCGTCGGCC
TGCCTGCGGAGACTCTCCGTCGATCGAAAGCCTCGCCCGCTCCCGCCCTC
TTCTTCCCCCTCCCCTCCTCTGCACCTCGATTTACCTGGTACGGACCTTCC
TGCCGTCTTCCTGTCTTCGAATACAGCTTCCTCTTTGTCTCCCGTCCAGAC
CAAGTCAGGAAGAGACACGACCTGGTACTAGTTCTGTGTGGGTCTCAGTT
GGACTGGGAAGCTTCCGGACTTGGTGACGGTTACACCTTTCTTGCGTCTTG
GGCTCTCCTTTTTTTTTTTTTTTTTTTTTTTTTGCTTTAAAAATTTT
TCCTTTTGGTTCTTTTACGTTCACGGCGCAAAGTAAAAGTTATCAGGAGGA
CAAAAAGGAGGTTGCTTTGTGCGGGAATGCAAGAGTAGGAAGGGGAAATTA
```

FIG. 2D

```
CAAGAACAGAAGAGACGAGAGAAGAGCGATTCTGGGCATAACAAGCTTGGC
ACTTGTCATTATCTGGTACCCTTGCATATATTTGCACATTTGCACATATAC
GCTTTTTATTTCGGTGATTGACCGAGGGGCGTTCCTCTTTCACGATGTTGA
AGATATTGTCTATGGTAGGTCAAACTTTATTCCGTTGTTGTTAATTAATGG
TTATCAGCTCCTCCCCTTTTCTCCGCCTAATGGCGCCTCCTATATTTTAAT
AGAGATGCCGAATACACAGGCAATCAGCTGACTCTGTGCTGCAGAAAAAGA
AGCAACAAGCGGAGGCTGCTGCTGGGCAGACCAAGAATAGGGTCGGAG
GTGCGAAAGCACGGATTCAACATGGTACGTTCGCCAGCATCGCTTCCCTC
TTGTGATAAAATGCGAAACACTTCTCCAATGGAATGGGCTAACTGTCAGCT
TCGTCCTTCTCACCTTTCACAGATCTTCTCCGGGTCGGAAACAGGAGGAG
GAGGAGAGCCGCACGGGTGCACGCCCATTAAATTCGAGTGGAAGAATGGC
GATGATCCGTTTCATTTTAGTGTGGTGATCGAACCGGACGAGGGATGTAC
AAGGGTGGCTCGTTCAAGTTCAATTTTGACATTCCCGAACACGACTACCCG
TTTGAACCGCCCAGAGTAAAATGCACCCAGCGGATATACCACCCGAACATC
GACCCGCAAGGAAATGTGTGTCTGAACATACTGCGTGATGGGTGGACAGCC
GCGTTGGATGTCCAGGCCGTTGCATTTGGCTTACTGGTGCGTTATCCTCTC
AGAAGGGAGAGAAAAGGGGAAAAAGAAAGAAAAAAAAACCTGGTGCATAG
AACTAACGCCAGCATGCCAAAACGAAACAGCACATATTCATCCACACCACG
TACGAAGACCCCTTAATCCAAGAAGTCGCTGACGACCTTCGGCTGAACCGT
GAGGGCTTCCGACGCAACGTTCGGACAGCCATGCAGGGGGGACGGTCCGG
AATACACAATACGATCGTGTCTTGAAGAGCTGAGATGGGTCGAAGGGGAGG
TGATCTACTATACCATGGATGCAGTGGTAGTGGTGGTGGTGG
```

FIG. 2E

Chitin Synthase Gene Intron Sequences

Intron 1 (2162 to 2443) (SEQ ID NO: 1) (282 bp):

GTGAGAAAA<u>CACTCTTTCC</u>TATGT<u>A</u>T<u>ATGC</u>ATATGATATAGATATAGATATAG
GTATACATTTATATACATATATAAGAGAGCGTGTGTGTCTGTGTGTGTCTG
TTTTGTGTGTGTATCTGTCTGTATATATATACACATCGATATATATATGCTT
TTGGCTACGTATTCAAGCACTGGTTCCCCCTGGTCGCGGGCCACGGTACCAGT
GGTTTCAGGATGATATCCTCTCAACACAGGAACCACCCCTT<u>GCTAACTTGCCC
CTTAAATCG</u>CTCCAG

Intron 2 (2901 to 2991) (SEQ ID NO: 2) (91 bp):

GTAGGTTTTTGTCCTTGATTTCTTTTTCTTTTTACTCCCCTCTGCTTTGGTTTAT
GGTCGTCTCCTTGCTGATTTGCTGCTGCCATCTTAG

Intron 3 (3354 to 3431) (SEQ ID NO: 3) (78 bp):

GTCAGTACATATATGATACCCGTAGCCCAATTTTTTGCACCTTCTACTACTGC
TACACTGTACTAACTTCCCGTCTAG

Intron 4 (4279 to 4387) (SEQ ID NO: 4) (109 bp):

GTATGTGTTGTTCAACAATATAAGTCTTTGTTCCTCCGAACAATGACATCCCT
CTTTCAACTTCCACTTTCTTCTTGCGTCTATTGTCTCCCAACACTAACATGTTC
TAG

Intron 5 (4582 to 4730) (SEQ ID NO: 5) (149 bp):

GTGAGTTTGCATAATCTCCTAGTCAACTAAGGGGAGCTTCAGAAATATCCAA
TTCGTGGCATTGTTATTTTCATTGCCCTTCTCCCCGGCGAGATTCCCGGCGCTG
AGCTCCGATATATGCGTTAGATGATACTGATAGCGCCCCTCAG

Intron 6 (5377 to 5495) (SEQ ID NO: 6) (119 bp):

GTAGGCCTTACTTTCCTTTTTTCCCCCTTCCTCTTTTTTTTTTTTCTTTCGCCTT
TTGGGGAAAAAAAAAAATAAAAAAATAAAAACACTTTGCTAACGTGTTCCTC
CCACAATCCAG

FIG. 3

```
  1  MAYPGSNSPG  GYGDGHRLHD  LPSGSQYNLP  AEHDASQSLL  HQNQGPFSGP
 51  FDDPQHHHRG  GSPVRSPSRY  SLTESYVTDH  PQAQDHYGGQ  MENPAAGFGV
101  PGRVPSPYTR  SETSSTEAWR  QRQAPGNLRR  YATRKVKLVQ  GSVLSVDYPV
151  PSAIQNAVQA  KYRNDLEGGS  EEFTHMRYTA  ATCDPNEFTL  HNGYNLRPAM
201  YNRHTELLIA  ITYYNEDKML  TSRTLHGVMQ  NIRDIVNLKK  SEFWNKGGPA
251  WQKIVVCLVF  DGIDPCDKDT  LDVLATIGIY  QDGVMKKDVD  GKETIAHIFE
301  YTTQLSVTAN  QQLIRPHDDG  PSTLPPVQMM  FCLKQKNSKK  INSHRWLFNA
351  FGRILNPEIC  ILLDAGTKPG  HKSLLALWEA  FYNDKDLGGS  CGEIHAMLGK
401  GWKNLINPLV  AAQNPEYKIS  NILDKPLESS  FGYVSVLPGA  FSAYRFRAIM
451  GRPLEQYFHG  DHTLSKQLGP  KGIEGMNIFK  KNMFLAEDRI  LCFELVAKAG
501  SKWHLSYVKS  SKGETDVPEG  APEFIGQRRR  WLNGSFAASI  YSLMHFGRMY
551  KSGHNLLRMF  FFHIQMIYNT  CTVIMTWFAL  ASYWLTTSVI  MDLVGNPPAP
601  ESGSTQRAPP  FGNTATPIVN  TVLKYLYLAF  LLLQFILALG  NRPKGSKHSY
651  ITSFVVFGII  QLYIIVLSMY  LVVRAFSGGT  LAFTTDKGIG  EFLKSFFSSE
701  GPGIIIIALA  ATPGLYFVAS  FMYLDPWHMF  TSFPAYLLIM  SSYINILMVY
751  AFSNWHDVSW  GTKGADKADA  LPSAQTQKED  DGKAAVIEEI  DKPQADIDSQ
801  FESTVKRALT  PYVEPKVKEG  KSLDDSYKSF  RTRLVTLWLF  SNGILAVAIT
851  SEDVNKFGFT  SRATSRTTHF  FHALLWATAA  LSLIRFTGAC  WFLGRTGIMC
901  CFARR*
```

FIG. 4

Chitin Synthase Intron 1 primers

Intron 1 5' primer sequence (SEQ ID NO: 7):

CACTCTTTCCTATGTATATGC

Intron 1 3' primer sequence (SEQ ID NO: 8):

CGATTTAAGGGGCAAGTTAGC

FIG. 6

```
                            SEQUENCE LISTING

<160> NUMBER OF SEQ ID NOS: 27

<210> SEQ ID NO 1
<211> LENGTH: 281
<212> TYPE: DNA
<213> ORGANISM: Histoplasma capsulatum

<400> SEQUENCE: 1
gtgagaaaac actctttcct atgtatatgc atatgatata gatatagata taggtataca      60
tttatataca tatataagag agcgtgtgtg tctgtgtgtg tgtctgtttt gtgtgtgtgt     120
atctgtctgt atatatatac acatcgatat atatatgctt ttggctacgt attcaagcac    180
tggttccccc tggtcgcggg ccacggtacc agtggtttca ggatgatatc ctctcaacac    240
aggaaccacc ccttgctaac ttgcccctta aatcgctcca g                        281

<210> SEQ ID NO 2
<211> LENGTH: 91
<212> TYPE: DNA
<213> ORGANISM: Histoplasma capsulatum

<400> SEQUENCE: 2
gtaggttttt gtccttgatt tctttttctt tttactcccc tctgctttgg tttatggtcg     60
tctccttgct gatttgctgc tgccatctta g                                    91

<210> SEQ ID NO 3
<211> LENGTH: 78
<212> TYPE: DNA
<213> ORGANISM: Histoplasma capsulatum

<400> SEQUENCE: 3
gtcagtacat atatgatacc cgtagcccaa ttttttgcac cttctactac tgctacactg     60
tactaacttc ccgtctag                                                   78

<210> SEQ ID NO 4
<211> LENGTH: 110
<212> TYPE: DNA
<213> ORGANISM: Histoplasma capsulatum

<400> SEQUENCE: 4
gtatgtgttg ttcaacaata taagtctttg ttcctccgaa caatgacatc cctctttcaa     60
cttccacttt cttcttgcgt ctattgtctc ccaacactaa catgttctag                110

<210> SEQ ID NO 5
<211> LENGTH: 149
<212> TYPE: DNA
<213> ORGANISM: Histoplasma capsulatum

<400> SEQUENCE: 5
gtgagtttgc ataatctcct agtcaactaa ggggagcttc agaaatatcc aattcgtggc     60
attgttattt tcattgccct tctccccggc gagattcccg gcgctgagct ccgatatatg    120
```

-continued

| cgttagatga tactgatagc gcccctcag | 149 |

<210> SEQ ID NO 6
<211> LENGTH: 119
<212> TYPE: DNA
<213> ORGANISM: Histoplasma capsulatum

<400> SEQUENCE: 6

| gtaggcctta ctttccttt tccccttc ctcttttt tttttcttt cgccttttgg | 60 |
| ggaaaaaaaa aaataaaaaa ataaaaacac tttgctaacg tgttcctccc acaatccag | 119 |

<210> SEQ ID NO 7
<211> LENGTH: 21
<212> TYPE: DNA
<213> ORGANISM: Artificial Sequence
<220> FEATURE:
<223> OTHER INFORMATION: Synthetic sequence

<400> SEQUENCE: 7

| cactctttcc tatgtatatg c | 21 |

<210> SEQ ID NO 8
<211> LENGTH: 21
<212> TYPE: DNA
<213> ORGANISM: Artificial Sequence
<220> FEATURE:
<223> OTHER INFORMATION: Synthetic sequence

<400> SEQUENCE: 8

| cgatttaagg ggcaagttag c | 21 |

<210> SEQ ID NO 9
<211> LENGTH: 2251
<212> TYPE: DNA
<213> ORGANISM: Histoplasma capsulatum

<400> SEQUENCE: 9

| cgcaaatcag caactgatcc gaccgcacga tgatggccca tcgacgcttc ccctgtgca | 60 |
| gatgatgttc tgcttgaaac aaaagaacag taagaaaatc aactctcaca gatggctgtt | 120 |
| caatgccttt ggccgaatcc tcaacccgga atctgcatc ttgctcgacg cgggtacgaa | 180 |
| gccgggtcat aaatccctcc tggcactgtg ggaagccttc tataacgaca aagatctggg | 240 |
| cggctcgtgc ggcgaaatcc acgctatgtt gggcaaaggc tggaaaaacc tcatcaaccc | 300 |
| tcttgttgca gcgcaaaact tcgaatacaa aatcagtaac atcctggata aacctctgga | 360 |
| atcctccttc ggctacgtca gcgtgttgcc cggtgccttc tctgcctacc gcttccgtgc | 420 |
| aatcatgggc agacctctcg aacagtactt ccacggtgac catacactct ccaaacaact | 480 |
| cggtcccaag ggtatcgagg gcatgaacat tttcaagaag aacatgttct tggccgagga | 540 |
| tcggattctg tgtttcgaac tcgtggccaa ggccgggtcc aaatgcatc tgtcctacgt | 600 |
| caagtcgtcc aagggcgaga ctgacgtgcc cgagggagcc cccgaattca tcggccagcg | 660 |
| tcgtcggtgg ctcaacggct cgttcgcagc tagtatctac tcattgatgc attttggccg | 720 |
| aatgtataag agcggccata accttctgcg catgttcttt ttccatattc agatgatcta | 780 |
| caatacgtgc accgttatca tgacttggtt tgcgcttgct tcatactggc tcacaacttc | 840 |
| cgtcatcatg gacctcgtcg gaaaccctcc cgctccagaa tctggcagca cgcagagggc | 900 |
| attcccattc ggcaataccg ccactccgat tgtcaacact gttctgaagt acttgtatct | 960 |
| ggccttcctg ctcttgcagt ttattttggc tttgggtaac cggcctaaag gatctaaaca | 1020 |

-continued

```
ctcgtacatc acctccttcg tcgtattcgg cattatccaa ttgtacatca ttgtcttatc    1080
catgtacctc gtcgtccgcg ccttcagcgg tggcacactc gccttcacaa cagacaaaag    1140
tatcggcgaa ttcctcaagt ccttcttcag ttccgaagga ccgggaatca tcatcatcgc    1200
cctcgccgct accttcggcc tatatttcgt cgcttctttc atgtaccttg accttggca    1260 catgttcacc tccttcccgg cctacctcct gatcatgtcc tcgtacatca acatcctgat    1320
ggtctacgcc ttcagcaact ggcacgatgt gtcgtggggc acaaagggtg cggacaaagc    1380
cgacgctctg ccctctgccc aaacgcaaaa ggaagacgac ggcaaagctg ctgtgatcga    1440
ggagatcgac aagccgcagg cggatatcga cagccagttt gaaagcactg tgaagcgtgc    1500
gctgacgccg tacgtggagc caaaggtgaa ggaggggaag tcgctagatg attcgtataa    1560
gagtttccgc acgcggttgg tgacgctatg gctgttttcg aatggcattc ttgccgtggc    1620
cattaccagc gaggatgtga acaagtttgg attcacgtcc cgagcaacca gccgaaccac    1680
gcatttcttc caggctctcc tttgggcgac cgcagcgctc tccctcatcc gcttcaccgg    1740
cgcatgctgg ttccttggcc ggactggaat tatgtgctgc ttcgcgagaa gatagtcagt    1800
ccatttggct ctggattttc tatatatttt gtttggtgat gcaaaaatct tttgcttccc    1860
tttttccttt tctctttcgg gtgacctttt tgttgcgggc gacggcacga aacccggaat    1920
aatataagac aaggatgggg gagaagagag catgaagatc gaagatcgaa agtcgaaagt    1980
cgaaaattga aggagaaga aggaaatga caagaaactg gcagctgccg cttggccaac    2040
tgttggaaag ttttctttt gcatttctat gaatatgtcc cgatttgtt ttctttcc    2100 cattgcttgt tgttcttttc gcttttttcg attcctttcc tataataatg gcaagatgtg    2160
tcctatttcc tcctgcctgg cctctctttt gtgtgtttct atatgcgtga gagcctctga    2220
attccgaatc taatgttctg tttgttgtct t                                   2251
```

<210> SEQ ID NO 10
<211> LENGTH: 8355
<212> TYPE: DNA
<213> ORGANISM: Histoplasma capsulatum
<220> FEATURE:
<221> NAME/KEY: misc_feature
<222> LOCATION: (46)..(46)
<223> OTHER INFORMATION: n=any nucleotide
<220> FEATURE:
<221> NAME/KEY: misc_feature
<222> LOCATION: (50)..(50)
<223> OTHER INFORMATION: n=any nucleotide
<220> FEATURE:
<221> NAME/KEY: misc_feature
<222> LOCATION: (73)..(73)
<223> OTHER INFORMATION: n=any nucleotide
<220> FEATURE:
<221> NAME/KEY: misc_feature
<222> LOCATION: (97)..(97)
<223> OTHER INFORMATION: n=any nucleotide
<220> FEATURE:
<221> NAME/KEY: misc_feature
<222> LOCATION: (108)..(108)
<223> OTHER INFORMATION: n=any nucleotide
<220> FEATURE:
<221> NAME/KEY: misc_feature
<222> LOCATION: (205)..(205)
<223> OTHER INFORMATION: n=any nucleotide
<220> FEATURE:
<221> NAME/KEY: misc_feature
<222> LOCATION: (215)..(215)
<223> OTHER INFORMATION: n=any nucleotide
<220> FEATURE:
<221> NAME/KEY: misc_feature
<222> LOCATION: (236)..(236)

```
<223> OTHER INFORMATION: n=any nucleotide
<220> FEATURE:
<221> NAME/KEY: misc_feature
<222> LOCATION: (254)..(254)
<223> OTHER INFORMATION: n=any nucleotide

<400> SEQUENCE: 10
tgcttttttg aaggttccta cccttagccc aaagtccggc tttccncttn ttttcttttt      60
ttcttttgg acnaggacca tggatccccc ccccatncat cgggtccnga gagaagatgg     120
tccaaatatt cttaaactat cttgatccct tgtaacccaa tgtccccaat cggcttccca    180
aaattggcca acaattccaa tttcnacccc ccacnagcgg gagtaatgga gcaacnatgc    240
aaacccgaac cccnatgcaa cggttcccca aaaagccacc cctctgaaca gtgattgaca    300
aatcggtgca aggcattgct cacggggtac tcacctgaac aatcgacacg cataaatgt    360
tggtggatgg caagacaatt aattcatctt cattgagctt tatttgttta ttcccagcca    420
ttcacaaaaa ccaaaagtcc aaaattccaa aaatcagggc ttggttttgc ctccccattt    480
tggccctgaa taacgggaag gttagttaca tagtaaaagt aaaaccgtgt tgaacaaaag    540
tttcgaggat cgcaaccaga caaattggac caggatctct tgacttcccg tctttcggct    600
aagaatagac ttttttttggg gcaacgaaat tctggtacaa cttttgatt ctggcgggtt     660
tcagatatgt ggggacatta tcgggaatga taaatttttt ttttttttt tttggactgc    720
tctcaaactc atgtgataat atcacagaca ataggtatcg caagcgagca tcttgacttg    780
actgctgaga agtgatcttg tcgctgcaat tggtggaggc gactaacaga cgaacagcct    840
cgcaggatgc atgcatgaat acagcaagtc gctgcagagg tcatcacatt atgatgtcct    900
ccacgcccgt tttccttcct tcagatacac ccatccatcc atatgcatat acatatacat    960
atacatatgt gtcgtgatgt gacggtgccg cgcgcagtat gaatgattcg ctgcctctaa   1020
gtatgggaca gtaagtatg tactgtacat atacgtatgt ctgtctgtct gtctgtctgt    1080
ctgtctgtat gcagtccaac tgtggacaaa gccctcgcgg caacgttcaa agcggcgaga    1140
caagagaaga aggtgaaatt aaactgagta gatggcagaa tcgccgccat gtctcccttt    1200
ccttccggct agaggaggca gaggaaaggc tgattgagcg agtgggggga gcattattta    1260
tccaccctga gctgggctgg gcctgggcgg agagtaccat tgagtagagt tgtgaactgt    1320
cggtctatgc tcgatggaag caacgtacct ggcttacctg gctcacctgg ttggaaatcc    1380
aaacggcgag tatatatcca tatcccagat atgtgcgcat gttgaatggt ggcgattaat    1440
cggatgtcca tgtcattctc ctttctcggc aaaatatata tctacctact tgtatggtaa    1500
tgtgtatccc acccttacca aacgcggctg aacaaagaaa gttacggtaa atttcacgct    1560
agtacccagc cagaagctgg gtacggctcc tgtgctctgt acagtccggc cataccatac    1620
cataccatac cgtaccatac cgtaccatat cacgttcatc caccgtttg cccccaagag    1680
aaatatcatc atcgccttt cgggcctgta gcttactttc ttttttccta tttttttctt    1740
ttctatttct atttctattt ctatttctat ttcgctgctt attattctcg cctgttggtc    1800
ttgtccagca agcctgggaa tatcaagcgc tcgtctgtgg tttgttttta tccgttgccc    1860
tgctttgtgt cccgctgccc ccttagctcc ctgtggcttc gctgccccta aaaaaacaat    1920
catcttcttc ttccgctgct ctgttctcgc tcgtctctct tctctcttct cttttctctg    1980
cctctcttcc tcctctcgat ccatccatct attctcccct ctatccttct atccgcttca    2040
tcaacccagc ctctcgtttt gacgcggcc acagctccct catcatggcc tatccaggct    2100
cgaactctcc aggggggtac ggcgatggcc atcgactcca tgacctccca tctggcagcg    2160
```

-continued

```
tgagaaaaca ctctttccta tgtatatgca tatgatatag atatagatat aggtatacat      2220
ttatatacat atataagaga gcgtgtgtgt ctgtgtgtgt gtctgttttg tgtgtgtgta      2280
tctgtctgta tatatataca catcgatata tatatgcttt tggctacgta ttcaagcact      2340
ggttccccct ggtcgcgggc cacggtacca gtggtttcag gatgatatcc tctcaacaca      2400
ggaaccaccc cttgctaact tgccccttaa atcgctccag caatataatc ttcccgccga      2460
acacgatgcc tcccaatcgc tcctccacca aaaccaaggc ccattcagcg gcccctttga      2520 tgaccccaa caccaccacc gcggtggctc tcctgtccga tccccctcca gatacagcct      2580
gacagaatcc tacgtaaccg accatcccca agctcaagac cactacggcg gccaaatgga      2640
aaatcccgcc gctggctttg tgttcccggg tcgggttccg tccccctata cccgcagtga      2700
gacctcctcc acggaggcct ggcgtcagcg acaggcgccc ggcaatctgc gccgttatgc      2760
caccaggaaa gtcaaacttg tccaaggctc tgttctcagt gtcgattatc ccgttcccag      2820
tgctattcag aatgccgtgc aggctaaata ccgcaatgat ctcgaaggtg gtagtgagga      2880
attcactcat atgcgatgta ggttttttgtc cttgatttct ttttcttttt actccctct      2940 gctttggttt atggtcgtct ccttgctgat ttgctgctgc catcttagac accgccgcta      3000
cctgtgatcc caacgagttc actctgcaca atgggtacaa tctgcgcccg gcgatgtata      3060
accgtcatac cgaactgctg attgctatta cctattacaa tgaagacaaa atgcttactt      3120
cgcgcaccct gcacggcgta atgcaaaata tccgtgacat tgtgaacctc aagaagtccg      3180
agttctggaa caaaggtgga cctgcttggc agaaaatcgt tgtctgtctg gtcttcgatg      3240
gaatcgaccc ttgcgacaaa gacaccctcg acgtgctggc cacaattgga atctaccagg      3300
atggcgtgat gaaaaaagat gtcgatggaa aggaaaccat cgcccacatt gtcagtacat      3360
atatgatacc cgtagcccaa ttttttgcac cttctactac tgctacactg tactaacttc      3420
ccgtctagtt tgaatacacc acccaactct cagtcaccgc aaatcagcaa ctgatccgac      3480
cgcacgatga tggcccatcg acgcttcccc ctgtgcagat gatgttctgc ttgaaacaaa      3540
agaacagtaa gaaaatcaac tctcacagat ggctgttcaa tgcctttggc cgaatcctca      3600
acccggaaat ctgcatcttg ctcgacgcgg gtacgaagcc gggtcataaa tccctcctgg      3660
cactgtggga agccttctat aacgacaaag atctgggcgg ctcgtgcggc gaaatccacg      3720
ctatgttggg caaaggctgg aaaaacctca tcaaccctct tgttgcagcg caaaacttcg      3780
aatacaaaat cagtaacatc ctggataaac tctctggaatc ctccttcggc tacgtcagcg      3840
tgttgcccgg tgccttctct gcctaccgct tccgtgcaat catgggcaga cctctcgaac      3900
agtacttcca cggtgaccat acactctcca aacaactcgg tcccaagggt atcgagggca      3960
tgaacatttt caagaagaac atgttcttgg ccgaggatcg gattctgtgt ttcgaactcg      4020
tggccaaggc cgggtccaaa tggcatctgt cctacgtcaa gtcgtccaag ggcgagactg      4080
acgtgcccga gggagccccc gaattcatcg gccagcgtcg tcggtggctc aacggctcgt      4140
tcgcagctag tatctactca ttgatgcatt ttggccgaat gtataagagc ggccataacc      4200
ttctgcgcat gttcttttc catattcaga tgatctacaa tacgtgcacc gttatcatga      4260
cttggtttgc gcttggtatg tgttgttcaa caatataagt cttttgttcct ccgaacaatg      4320 acatccctct ttcaacttcc actttcttct tgcgtctatt gtctcccaac actaacatgt      4380
tctagcttca tactggctca caacttccgt catcatggac ctcgtcggaa accctcccgc      4440
tccagaatct ggcagcacgc agagggcatt cccattcggc aataccgcca ctccgattgt      4500
```

```
caacactgtt ctgaagtact tgtatctggc cttcctgctc ttgcagttta ttttggcttt   4560
gggtaaccgg cctaaagggt gagtttgcat aatctcctag tcaactaagg ggagcttcag   4620
aaatatccaa ttcgtggcat tgttattttc attgcccttc tccccggcga gattcccggc   4680
gctgagctcc gatatatgcg ttagatgata ctgatagcgc ccctcagatc taaacactcg   4740
tacatcacct ccttcgtcgt attcggcatt atccaattgt acatcattgt cttatccatg   4800
tacctcgtcg tccgcgcctt cagcggtggc acactcgcct tcacaacaga caaaggtatc   4860
ggcgaattcc tcaagtcctt cttcagttcc gaaggaccgg gaatcatcat catcgccctc   4920
gccgctacct tcggcctcta tttcgtcgcc tctttcatgt accttgaccc ctggcacatg   4980
ttcacctcct cccggcccta cctcctgatc atgtcctcgt acatcaacat cctgatggtc   5040
tacgccttca gcaactggca cgatgtgtcg tggggcacaa agggtgcgga caaagccgac   5100
gctctgccct ctgcccaaac gcaaaaggaa gacgacggca agctgctgt gatcgaggag    5160 atcgacaagc cgcaggcgga tatcgacagc cagtttgaaa gcactgtgaa gcgtgcgctg   5220
acgccgtacg tggagccaaa ggtgaaggag gggaagtcgc tagatgattc gtataagagt   5280
ttccgcacgc ggttggtgac gctatggctg ttttcgaatg gcattcttgc cgtggccatt   5340
accagcgagg atgtgaacaa gtttggattc acggtaggcc ttactttcct tttttcccc    5400 ttcctctttt ttttttttc tttcgccttt tggggaaaaa aaaaataaa aaataaaaa      5460 cactttgcta acgtgttcct cccacaatcc agtcccgagc aaccagccga ccacgcatt    5520 tcttccacgc tctcctttgg gcgaccgcag cgctctccct catccgcttc accggcgcat   5580
gctggttcct tggccggact ggaattatgt gctgcttcgc gagaagatag tcagtccatt   5640
tggctctgga ttttctatat attttgtttg gtgatgcaaa aatcttttgc ttccctttt    5700 ccttttctct ttcgggtgac cttttttgttg cgggcgacgg cacgaaaccc ggaataatat  5760
aagacaagga tgggggagaa gagagcatga agatcgaaga tcgaaagtcg aaagtcgaaa   5820
attgaaagga gaagaaagga aatgacaaga aactggcagc tgccgcttgg ccaactgttg   5880
gaaagttttt cttttgcatt tctatgaata tgtcccgatt ttgttttct tttcccattg    5940 cttgttgttc ttttcgcttt tttcgattcc tttcctataa taatgcaag atgtgtccta    6000 tttcctcctg cctggcctct cttttgtgtg tttctatatg cgtgagagcc tctgaattcc   6060
gaatctaatg ttctgtttgt tgtcttattt ctctgatcgt ccccgccccc tggtgttttt   6120
gttgctgctg ttcttgctgt tactgctttt tctgtttctg ggtttttccc ttgttgtgta   6180
aatttactat atcctaccta gatgactttt tttttttta ttttcttttt cgctctccgc    6240
ctcttctgca aatgatgtag ctaattggct gatatgattg gaatgaattg aaggcattta   6300
cttttcgaat ccatttattg acggctgtag cctgtagcct gtagccttgt actgcgtatg   6360
tacatgtata ttatggagtt cacccgccaa accacagctc gggccgttgg gcaatcagcc   6420
gtgtcacgtg cactcggctc ccctgcccga tgcatcagcg tcattcctca tcctatcccc   6480
gtcttggaat cctcccaggc ctcactcccc atccgccaac ctttgcacaa cgccgttact   6540
ctgcactctg actgcttgtc cgtcggcccg ccgtcagcc ctcgttccgc tccctttcgg    6600
cccctttttg ttttgccccc ttcacggtcc caaagaaat cttatcttat cacggcacac    6660
caacaccact gtcgtgtac tgtacatgta catacacaca cccagccccc gcctcgcatc    6720
tcaacgacag cataaacaac cccaagccca gttccacttg gcttctcttc cccgtagttt   6780
gtgtcccgct ctatctccct cgggcctccg tgcttggacc ataaaccgtc ggcctgcctg   6840
cggagactct ccgtcgatcg aaagcctcgc ccgctccccg ccctcttctt cccctcccc    6900
```

-continued

```
tcctctgcac ctcgatttac ctggtacgga ccttcctgcc gtcttcctgt cttcgaatac      6960
agcttcctct ttgtctcccg tccagaccaa gtcaggaaga gacacgacct ggtactagtt      7020
ctgtgtgggg tctcagttgg actgggaagc ttccggactt ggtgacggtt acacctttct      7080
tgcgtcttgg gctctccttt tttttttttt tttttttttt ttttgctttt aaaaaatttt      7140
tccttttggt tcttttacgt tcacggcgca aagtaaaagt tatcaggagg acaaaaagga      7200
ggttgctttg tgcgggaatg caagagtagg aaggggaaat tacaagaaca gaagagacga      7260
gagaagagcg attctgggca taacaagctt ggcacttgtc attatctggt acccttgcat      7320
atatttgcac atttgcacat atacgctttt tatttcggtg attgaccgag ggcgttcct       7380 cttttcacgat gttgaagata ttgtctatgg taggtcaaac tttattccgt tgttgttaat     7440
taatggttat cagctcctcc ccttttctcc gcctaatggc gcctcctata ttttaataga     7500
gatgccgaat acacaggcaa tcagctgact ctgtgctgca gaaaaagaag caacaagcgg      7560
aggctgctgc tgctgggcag accaagaata gggtcggagg tgcgaaagca cggattcaac     7620
atggtacgtt ccgccagcat cgcttccctc ttgtgataaa atgcgaaaca cttctccaat     7680
ggaatgggct aactgtcagc ttcgtccttc tcacctttca cagatcttct ccgggtcggg     7740
aaacaggagg aggaggagag ccgcacgggt gcacgcccca ttaaattcga gtggaagaat     7800
ggcgatgatc cgtttcattt tagtgtggtg atcgaaccgg acgagggat gtacaagggt      7860 ggctcgttca agttcaattt tgacattccc gaacacgact acccgtttga accgcccaga     7920
gtaaaatgca cccagcggat ataccacccg aacatcgacc cgcaaggaaa tgtgtgtctg     7980
aacatactgc gtgatgggtg gacagccgcg ttggatgtcc aggccgttgc atttggctta     8040
ctggtgcgtt atcctctcag aagggagaga aagggaaa aagaaagaa aaaaaacct        8100 ggtgcataga actaacgcca gcatgccaaa acgaaacagc acatattcat ccacaccacg     8160
tacgaagacc ccttaatcca agaagtcgct gacgaccttc ggctgaaccg tgagggcttc     8220
cgacgcaacg ttcggacagc catgcagggg gggacggtcc ggaatacaca atacgatcgt     8280
gtcttgaaga gctgagatgg gtcgaagggg aggtgatcta ctataccatg gatgcagtgg     8340
tagtggtggt ggtgg                                                      8355
```

<210> SEQ ID NO 11
<211> LENGTH: 33
<212> TYPE: DNA
<213> ORGANISM: Artificial Sequence
<220> FEATURE:
<223> OTHER INFORMATION: Synthetic sequence

<400> SEQUENCE: 11

```
tttgaattct gatcactgct tcaatgccga gag                                    33
```

<210> SEQ ID NO 12
<211> LENGTH: 28
<212> TYPE: DNA
<213> ORGANISM: Artificial Sequence
<220> FEATURE:
<223> OTHER INFORMATION: Synthetic sequence

<400> SEQUENCE: 12

```
tttgtcgacg gctgggaccc ttcttgag                                          28
```

<210> SEQ ID NO 13
<211> LENGTH: 30
<212> TYPE: DNA

```
<213> ORGANISM: Artificial Sequence
<220> FEATURE:
<223> OTHER INFORMATION: Synthetic sequence

<400> SEQUENCE: 13
aaaagtcgac ccaactgcaa gtattgttac                                    30

<210> SEQ ID NO 14
<211> LENGTH: 36
<212> TYPE: DNA
<213> ORGANISM: Artificial Sequence
<220> FEATURE:
<223> OTHER INFORMATION: Synthetic sequence

<400> SEQUENCE: 14
aaaagtcgac tgatcaggat gtgctgtatc gcatcg                             36

<210> SEQ ID NO 15
<211> LENGTH: 20
<212> TYPE: DNA
<213> ORGANISM: Artificial Sequence
<220> FEATURE:
<223> OTHER INFORMATION: Synthetic sequence

<400> SEQUENCE: 15
ctacctgtga tcccaacgag                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic sequence

<400> SEQUENCE: 16
acgccatcct ggtagattcc                                               20

<210> SEQ ID NO 17
<211> LENGTH: 33
<212> TYPE: DNA
<213> ORGANISM: Artificial Sequence
<220> FEATURE:
<223> OTHER INFORMATION: Synthetic sequence

<400> SEQUENCE: 17
aaggaattct ctagacccctt gtacccaat gtc                                33

<210> SEQ ID NO 18
<211> LENGTH: 38
<212> TYPE: DNA
<213> ORGANISM: Artificial Sequence
<220> FEATURE:
<223> OTHER INFORMATION: Synthetic sequence

<400> SEQUENCE: 18
aaggaaaaaa gcggccgcca aaacgagagg ctgggttg                           38

<210> SEQ ID NO 19
<211> LENGTH: 37
<212> TYPE: DNA
<213> ORGANISM: Artificial Sequence
<220> FEATURE:
<223> OTHER INFORMATION: Synthetic sequence

<400> SEQUENCE: 19
aaggaaaaaa gcggccgcgc tgccgcttgg ccaactg                            37
```

-continued

<210> SEQ ID NO 20
<211> LENGTH: 27
<212> TYPE: DNA
<213> ORGANISM: Artificial Sequence
<220> FEATURE:
<223> OTHER INFORMATION: Synthetic sequence

<400> SEQUENCE: 20
aagtctagag acccatctca gctcttc                                         27

<210> SEQ ID NO 21
<211> LENGTH: 30
<212> TYPE: DNA
<213> ORGANISM: Artificial Sequence
<220> FEATURE:
<223> OTHER INFORMATION: Synthetic sequence

<400> SEQUENCE: 21
tcgagcggcc gcgagttata ctgatgtctg                                      30

<210> SEQ ID NO 22
<211> LENGTH: 30
<212> TYPE: DNA
<213> ORGANISM: Artificial Sequence
<220> FEATURE:
<223> OTHER INFORMATION: Synthetic sequence

<400> SEQUENCE: 22
atctgcggcc gcattacctc taaacaagtg                                      30

<210> SEQ ID NO 23
<211> LENGTH: 905
<212> TYPE: PRT
<213> ORGANISM: Histoplasma capsulatum

<400> SEQUENCE: 23

Met Ala Tyr Pro Gly Ser Asn Ser Pro Gly Gly Tyr Gly Asp Gly His
1               5                   10                  15

Arg Leu His Asp Leu Pro Ser Gly Ser Gln Tyr Asn Leu Pro Ala Glu
            20                  25                  30

His Asp Ala Ser Gln Ser Leu Leu His Gln Asn Gln Gly Pro Phe Ser
        35                  40                  45

Gly Pro Phe Asp Asp Pro Gln His His His Arg Gly Gly Ser Pro Val
    50                  55                  60

Arg Ser Pro Ser Arg Tyr Ser Leu Thr Glu Ser Tyr Val Thr Asp His
65                  70                  75                  80

Pro Gln Ala Gln Asp His Tyr Gly Gly Gln Met Glu Asn Pro Ala Ala
                85                  90                  95

Gly Phe Gly Val Pro Gly Arg Val Pro Ser Pro Tyr Thr Arg Ser Glu
            100                 105                 110

Thr Ser Ser Thr Glu Ala Trp Arg Gln Arg Gln Ala Pro Gly Asn Leu
        115                 120                 125

Arg Arg Tyr Ala Thr Arg Lys Val Lys Leu Val Gln Gly Ser Val Leu
    130                 135                 140

Ser Val Asp Tyr Pro Val Pro Ser Ala Ile Gln Asn Ala Val Gln Ala
145                 150                 155                 160

Lys Tyr Arg Asn Asp Leu Glu Gly Gly Ser Glu Glu Phe Thr His Met
                165                 170                 175

Arg Tyr Thr Ala Ala Thr Cys Asp Pro Asn Glu Phe Thr Leu His Asn

```
                    180             185             190
Gly Tyr Asn Leu Arg Pro Ala Met Tyr Asn Arg His Thr Glu Leu Leu
            195                 200                 205
Ile Ala Ile Thr Tyr Tyr Asn Glu Asp Lys Met Leu Thr Ser Arg Thr
210                 215                 220
Leu His Gly Val Met Gln Asn Ile Arg Asp Ile Val Asn Leu Lys Lys
225                 230                 235                 240
Ser Glu Phe Trp Asn Lys Gly Pro Ala Trp Gln Lys Ile Val Val
            245                 250                 255
Cys Leu Val Phe Asp Gly Ile Asp Pro Cys Asp Lys Asp Thr Leu Asp
            260                 265                 270
Val Leu Ala Thr Ile Gly Ile Tyr Gln Asp Gly Val Met Lys Lys Asp
            275                 280                 285
Val Asp Gly Lys Glu Thr Ile Ala His Ile Phe Glu Tyr Thr Thr Gln
            290                 295                 300
Leu Ser Val Thr Ala Asn Gln Gln Leu Ile Arg Pro His Asp Asp Gly
305                 310                 315                 320
Pro Ser Thr Leu Pro Pro Val Gln Met Met Phe Cys Leu Lys Gln Lys
            325                 330                 335
Asn Ser Lys Lys Ile Asn Ser His Arg Trp Leu Phe Asn Ala Phe Gly
            340                 345                 350
Arg Ile Leu Asn Pro Glu Ile Cys Ile Leu Leu Asp Ala Gly Thr Lys
            355                 360                 365
Pro Gly His Lys Ser Leu Leu Ala Leu Trp Glu Ala Phe Tyr Asn Asp
            370                 375                 380
Lys Asp Leu Gly Gly Ser Cys Gly Glu Ile His Ala Met Leu Gly Lys
385                 390                 395                 400
Gly Trp Lys Asn Leu Ile Asn Pro Leu Val Ala Ala Gln Asn Phe Glu
            405                 410                 415
Tyr Lys Ile Ser Asn Ile Leu Asp Lys Pro Leu Glu Ser Ser Phe Gly
            420                 425                 430
Tyr Val Ser Val Leu Pro Gly Ala Phe Ser Ala Tyr Arg Phe Arg Ala
            435                 440                 445
Ile Met Gly Arg Pro Leu Glu Gln Tyr Phe His Gly Asp His Thr Leu
450                 455                 460
Ser Lys Gln Leu Gly Pro Lys Gly Ile Glu Gly Met Asn Ile Phe Lys
465                 470                 475                 480
Lys Asn Met Phe Leu Ala Glu Asp Arg Ile Leu Cys Phe Glu Leu Val
            485                 490                 495
Ala Lys Ala Gly Ser Lys Trp His Leu Ser Tyr Val Lys Ser Ser Lys
            500                 505                 510
Gly Glu Thr Asp Val Pro Glu Gly Ala Pro Glu Phe Ile Gly Gln Arg
            515                 520                 525
Arg Arg Trp Leu Asn Gly Ser Phe Ala Ala Ser Ile Tyr Ser Leu Met
            530                 535                 540
His Phe Gly Arg Met Tyr Lys Ser Gly His Asn Leu Leu Arg Met Phe
545                 550                 555                 560
Phe Phe His Ile Gln Met Ile Tyr Asn Thr Cys Thr Val Ile Met Thr
            565                 570                 575
Trp Phe Ala Leu Ala Ser Tyr Trp Leu Thr Thr Ser Val Ile Met Asp
            580                 585                 590
Leu Val Gly Asn Pro Pro Ala Pro Glu Ser Gly Ser Thr Gln Arg Ala
            595                 600                 605
```

```
Phe Pro Phe Gly Asn Thr Ala Thr Pro Ile Val Asn Thr Val Leu Lys
    610                 615                 620

Tyr Leu Tyr Leu Ala Phe Leu Leu Gln Phe Ile Leu Ala Leu Gly
625                 630                 635                 640

Asn Arg Pro Lys Gly Ser Lys His Ser Tyr Ile Thr Ser Phe Val Val
                645                 650                 655

Phe Gly Ile Ile Gln Leu Tyr Ile Ile Val Leu Ser Met Tyr Leu Val
            660                 665                 670

Val Arg Ala Phe Ser Gly Gly Thr Leu Ala Phe Thr Thr Asp Lys Gly
        675                 680                 685

Ile Gly Glu Phe Leu Lys Ser Phe Ser Ser Glu Gly Pro Gly Ile
    690                 695                 700

Ile Ile Ile Ala Leu Ala Ala Thr Phe Gly Leu Tyr Phe Val Ala Ser
705                 710                 715                 720

Phe Met Tyr Leu Asp Pro Trp His Met Phe Thr Ser Phe Pro Ala Tyr
                725                 730                 735

Leu Leu Ile Met Ser Ser Tyr Ile Asn Ile Leu Met Val Tyr Ala Phe
            740                 745                 750

Ser Asn Trp His Asp Val Ser Trp Gly Thr Lys Gly Ala Asp Lys Ala
        755                 760                 765

Asp Ala Leu Pro Ser Ala Gln Thr Gln Lys Glu Asp Asp Gly Lys Ala
770                 775                 780

Ala Val Ile Glu Glu Ile Asp Lys Pro Gln Ala Asp Ile Asp Ser Gln
785                 790                 795                 800

Phe Glu Ser Thr Val Lys Arg Ala Leu Thr Pro Tyr Val Glu Pro Lys
                805                 810                 815

Val Lys Glu Gly Lys Ser Leu Asp Asp Ser Tyr Lys Ser Phe Arg Thr
            820                 825                 830

Arg Leu Val Thr Leu Trp Leu Phe Ser Asn Gly Ile Leu Ala Val Ala
        835                 840                 845

Ile Thr Ser Glu Asp Val Asn Lys Phe Gly Phe Thr Ser Arg Ala Thr
850                 855                 860

Ser Arg Thr Thr His Phe Phe His Ala Leu Leu Trp Ala Thr Ala Ala
865                 870                 875                 880

Leu Ser Leu Ile Arg Phe Thr Gly Ala Cys Trp Phe Leu Gly Arg Thr
                885                 890                 895

Gly Ile Met Cys Cys Phe Ala Arg Arg
            900                 905

<210> SEQ ID NO 24
<211> LENGTH: 902
<212> TYPE: PRT
<213> ORGANISM: Coccidioides immitis

<400> SEQUENCE: 24

Met Ala Tyr Gln Gly Gly Gly Asn Ser Pro Gly Gly Tyr Gly Asp
1               5                   10                  15

His Arg Leu Gln Asp Met Pro Ser Asn Gly Ser Gln Tyr His Leu Pro
            20                  25                  30

Gln Asp Asp Ala Ser Arg Ser Leu Leu Asn Gln Gly Pro Tyr Gly
        35                  40                  45

Gly Pro Phe Asp Asp Pro His Gln Arg Thr Ala Ser Pro Ala Arg Pro
    50                  55                  60

Ala Ser Arg Tyr Ser Leu Thr Glu Ser Tyr Ala Thr Asp Pro Gln Asn
```

-continued

```
            65                  70                  75                  80
Met Ser Gln Tyr Asn Asp Pro Met Tyr Gly Gln Gln Thr Asp Asn Pro
                85                  90                  95
Ala Ala Gly Phe Gly Val Pro Gly Arg Val Ala Ser Pro Tyr Ser Arg
               100                 105                 110
Ser Glu Thr Ser Ser Thr Asp Ala Trp Arg Arg Gln Ala Pro Gln
       115                 120                 125
Gly Asn Leu Arg Arg Tyr Ala Thr Arg Lys Val Lys Leu Val Gln Gly
    130                 135                 140
Ser Val Leu Ser Val Asp Tyr Pro Val Pro Ser Ala Ile Gln Asn Ala
145                 150                 155                 160
Val Gln Ala Lys Tyr Arg Asn Asp Leu Glu Gly Gly Ser Glu Glu Phe
               165                 170                 175
Thr His Met Arg Tyr Thr Ala Ala Thr Cys Asp Pro Asn Asp Phe Thr
               180                 185                 190
Leu His Asn Gly Tyr Asn Leu Pro Ala Met Tyr Asn Arg His Thr Glu
           195                 200                 205
Leu Leu Ile Ala Ile Thr Tyr Tyr Asn Glu Asp Lys Met Leu Thr Ser
    210                 215                 220
Arg Thr Leu His Gly Val Met Gln Asn Ile Arg Asp Ile Val Asn Ile
225                 230                 235                 240
Lys Lys Ser Glu Phe Trp Asn Lys Gly Gly Pro Ala Trp Gln Lys Ile
               245                 250                 255
Val Val Ala Leu Ile Phe Asp Gly Ile Asp Pro Cys Asp Lys Asp Val
           260                 265                 270
Leu Asp Val Leu Ala Thr Ile Gly Val Tyr Gln Asp Gly Val Met Lys
    275                 280                 285
Arg Asp Val Asp Gly Lys Glu Thr Val Ala His Ile Phe Glu Tyr Thr
290                 295                 300
Thr Gln Leu Ser Val Thr Ala Asn Gln Gln Leu Ile Arg Pro His Asp
305                 310                 315                 320
Asp Gly Pro Ser Thr Leu Pro Pro Val Gln Met Met Phe Cys Leu Lys
               325                 330                 335
Gln Lys Asn Ser Lys Lys Ile Asn Ser His Arg Trp Leu Phe Asn Ala
           340                 345                 350
Phe Gly Arg Ile Leu Asn Pro Glu Ile Cys Ile Leu Leu Asp Ala Gly
           355                 360                 365
Thr Lys Pro Gly Ser Lys Ser Leu Leu Ala Leu Trp Glu Ala Phe Tyr
    370                 375                 380
Asn Asp Lys Asp Leu Gly Gly Ser Cys Gly Glu Ile His Ala Met Leu
385                 390                 395                 400
Gly Lys Gly Trp Thr Lys Leu Ile Asn Pro Leu Val Ala Ala Gln Asn
               405                 410                 415
Phe Glu Tyr Lys Ile Ser Asn Ile Leu Asp Lys Pro Leu Glu Ser Ser
               420                 425                 430
Phe Gly Tyr Val Ser Val Leu Pro Gly Ala Phe Ser Ala Tyr Arg Phe
           435                 440                 445
Arg Ala Ile Met Gly Arg Pro Leu Glu Gln Tyr Phe His Gly Asp His
    450                 455                 460
Thr Leu Ser Lys Gln Leu Gly Pro Lys Gly Ile Glu Gly Met Asn Ile
465                 470                 475                 480
Phe Lys Lys Asn Met Phe Leu Ala Glu Asp Arg Ile Leu Cys Phe Glu
               485                 490                 495
```

-continued

```
Leu Val Ala Lys Ala Gly Ser Lys Trp His Leu Thr Tyr Val Lys Ala
            500                 505                 510
Ser Lys Gly Glu Thr Asp Val Pro Glu Gly Ala Pro Glu Phe Ile Ser
            515                 520                 525
Gln Arg Arg Trp Leu Asn Gly Ser Phe Ala Ala Ser Ile Tyr Ala
            530                 535                 540
Leu Met His Phe Gly Arg Met Tyr Lys Ser Gly His Asn Ile Leu Arg
545                 550                 555                 560
Met Phe Phe His Ile Gln Met Leu Tyr Asn Thr Phe Thr Val Phe
                565                 570                 575
Leu Thr Trp Phe Ala Leu Ala Ala Tyr Trp Leu Thr Thr Ser Val Ile
            580                 585                 590
Met Asp Leu Val Gly Asn Pro Asn Gln Glu Gly Gln Arg Ala Phe Pro
            595                 600                 605
Phe Gly Asn Lys Val Thr Pro Ile Leu Asn Thr Val Leu Lys Tyr Leu
            610                 615                 620
Tyr Leu Gly Phe Leu Leu Gln Phe Ile Leu Ala Leu Gly Asn Arg
625                 630                 635                 640
Pro Lys Gly Ser Lys His Ser Tyr Ile Thr Ser Phe Ile Leu Phe Gly
                645                 650                 655
Leu Val Gln Leu Tyr Ile Val Ile Leu Ser Met Tyr Leu Val Val Arg
            660                 665                 670
Ala Phe Ser Gly Ser Val Asp Phe Glu Thr Asp Lys Gly Val Asp Gly
            675                 680                 685
Phe Leu Lys Ser Phe Phe Gly Ser Asp Ser Ala Gly Ile Ile Val Ile
            690                 695                 700
Ala Leu Ala Ala Thr Phe Gly Leu Tyr Phe Val Ala Ser Phe Met Tyr
705                 710                 715                 720
Met Asp Pro Trp His Met Phe Thr Ser Phe Pro Ala Tyr Leu Leu Ile
                725                 730                 735
Met Ser Ser Tyr Ile Asn Ile Leu Met Val Tyr Ala Phe Ser Asn Trp
            740                 745                 750
His Asp Val Ser Trp Gly Thr Lys Gly Ser Asp Lys Ala Asp Ala Leu
            755                 760                 765
Pro Ser Ala Gln Thr Thr Lys Glu Asp Gly Gly Lys Ala Ala Val Ile
            770                 775                 780
Glu Glu Ile Asp Lys Pro Gln Ala Asp Ile Asp Ser Gln Phe Glu Ala
785                 790                 795                 800
Thr Val Lys Arg Ala Leu Thr Pro Phe Val Glu Pro Lys Val Asp Glu
                805                 810                 815
Lys Lys Ser Leu Glu Asp Ser Tyr Lys Ser Phe Arg Thr Arg Leu Val
            820                 825                 830
Ala Ser Trp Ile Phe Ser Asn Ala Leu Leu Ala Val Leu Ile Thr Ser
            835                 840                 845
Asp Ser Val Asn Lys Leu Gly Phe Thr Ser Gln Ala Thr Asp Arg Thr
850                 855                 860
Ala Asn Phe Phe Arg Ala Leu Leu Trp Ala Thr Ala Ala Leu Ser Leu
865                 870                 875                 880
Ile Arg Phe Ile Gly Ala Cys Trp Phe Leu Gly Lys Ser Gly Ile Met
                885                 890                 895
Cys Cys Phe Ala Arg Arg
            900
```

<210> SEQ ID NO 25
<211> LENGTH: 911
<212> TYPE: PRT
<213> ORGANISM: Aspergillus fumigatus

<400> SEQUENCE: 25

```
Met Ala Tyr Gln Gly Ser Gly Ser His Ser Pro Pro His Tyr Asp Asp
1               5                   10                  15

Asn Gly His Arg Leu Gln Asp Leu Pro His Gly Ser Tyr Glu Glu Glu
            20                  25                  30

Ala Ser Arg Gly Leu Leu Ser His Gln Gln Gly Pro Phe Thr Gly Pro
        35                  40                  45

Phe Asp Asp Pro Gln Gln His Gly Ser Ser Thr Thr Arg Pro Val Ser
50                  55                  60

Gly Tyr Ser Leu Ser Glu Thr Tyr Ala Pro Glu Ala Ala Tyr His Asp
65                  70                  75                  80

Pro Tyr Thr Gln Pro Ser Pro Gly Ser Val Tyr Ser Ala Gln Ser Ala
                85                  90                  95

Glu Asn Pro Ala Ala Ala Phe Gly Val Pro Gly Arg Val Ala Ser Pro
            100                 105                 110

Tyr Ala Arg Ser Asp Thr Ser Thr Glu Ala Trp Arg Gln Arg Gln
        115                 120                 125

Ala Pro Gly Gly Pro Gly Gly Leu Arg Arg Tyr Ala Thr Arg Lys
    130                 135                 140

Val Lys Leu Val Gln Gly Ser Val Leu Ser Val Asp Tyr Pro Val Pro
145                 150                 155                 160

Ser Ala Ile Gln Asn Ala Ile Gln Ala Lys Tyr Arg Asn Asp Leu Glu
                165                 170                 175

Gly Gly Ser Glu Glu Phe Thr His Met Arg Tyr Thr Ala Ala Thr Cys
            180                 185                 190

Asp Pro Asn Glu Phe Thr Leu His Asn Gly Tyr Asn Leu Arg Pro Ala
        195                 200                 205

Met Tyr Asn Arg His Thr Glu Leu Leu Ile Ala Ile Thr Tyr Tyr Asn
    210                 215                 220

Glu Asp Lys Thr Leu Thr Ser Arg Thr Leu His Gly Val Met Gln Asn
225                 230                 235                 240

Ile Arg Asp Ile Val Asn Leu Lys Lys Ser Glu Phe Trp Asn Lys Gly
                245                 250                 255

Gly Pro Ala Trp Gln Lys Ile Val Val Cys Leu Val Phe Asp Gly Ile
            260                 265                 270

Asp Pro Cys Asp Lys Asp Thr Leu Asp Val Leu Ala Thr Ile Gly Val
        275                 280                 285

Tyr Gln Asp Gly Val Met Lys Arg Asp Val Asp Gly Lys Glu Thr Val
    290                 295                 300

Ala His Ile Phe Glu Tyr Thr Thr Gln Leu Ser Val Thr Pro Asn Gln
305                 310                 315                 320

Gln Leu Ile Arg Pro Thr Asp Asp Gly Pro Ser Thr Leu Pro Pro Val
                325                 330                 335

Gln Met Met Phe Cys Leu Lys Gln Lys Asn Ser Lys Lys Ile Asn Ser
            340                 345                 350

His Arg Trp Leu Phe Asn Ala Phe Gly Arg Ile Leu Asn Pro Glu Val
        355                 360                 365

Cys Ile Leu Leu Asp Ala Gly Thr Lys Pro Gly Pro Lys Ser Leu Leu
    370                 375                 380
```

-continued

Ser Leu Trp Glu Ala Phe Tyr Asn Asp Lys Asp Leu Gly Gly Ala Cys
385                 390                 395                 400

Gly Glu Ile His Ala Met Leu Gly Lys Gly Trp Lys Asn Leu Ile Asn
            405                 410                 415

Pro Leu Val Ala Ala Gln Asn Phe Glu Tyr Lys Ile Ser Asn Ile Leu
                420                 425                 430

Asp Lys Pro Leu Glu Ser Ser Phe Gly Tyr Val Ser Val Leu Pro Gly
            435                 440                 445

Ala Phe Ser Ala Tyr Arg Phe Arg Ala Ile Met Gly Arg Pro Leu Glu
450                 455                 460

Gln Tyr Phe His Gly Asp His Thr Leu Ser Lys Gln Leu Gly Lys Lys
465                 470                 475                 480

Gly Ile Glu Gly Met Asn Ile Phe Lys Lys Asn Met Phe Leu Ala Glu
                485                 490                 495

Asp Arg Ile Leu Cys Phe Glu Leu Val Ala Lys Ala Gly Ser Lys Trp
            500                 505                 510

His Leu Thr Tyr Val Lys Ala Ser Lys Ala Glu Thr Asp Val Pro Glu
            515                 520                 525

Gly Ala Pro Glu Phe Ile Ser Gln Arg Arg Arg Trp Leu Asn Gly Ser
530                 535                 540

Phe Ala Ala Gly Ile Tyr Ser Leu Met His Phe Gly Arg Met Tyr Lys
545                 550                 555                 560

Ser Gly His Asn Ile Val Arg Met Phe Phe Leu His Ile Gln Met Leu
                565                 570                 575

Tyr Asn Ile Phe Ser Thr Val Leu Thr Trp Phe Ser Leu Ala Ser Tyr
            580                 585                 590

Trp Leu Thr Thr Thr Val Ile Met Asp Leu Val Gly Thr Pro Ser Asp
            595                 600                 605

Asn Asn Gly Asn Lys Ala Phe Pro Phe Gly Lys Thr Ala Thr Pro Ile
610                 615                 620

Ile Asn Thr Ile Val Lys Tyr Val Tyr Leu Gly Phe Leu Leu Leu Gln
625                 630                 635                 640

Phe Ile Leu Ala Leu Gly Asn Arg Pro Lys Gly Ser Lys Phe Ser Tyr
                645                 650                 655

Leu Ala Ser Phe Val Val Phe Gly Ile Ile Gln Val Tyr Val Val Ile
            660                 665                 670

Asp Ala Leu Tyr Leu Val Val Arg Ala Phe Ser Gly Ser Ala Pro Met
            675                 680                 685

Asp Phe Thr Thr Asp Gln Gly Val Gly Glu Phe Leu Lys Ser Phe Phe
690                 695                 700

Ser Ser Ser Gly Ala Gly Ile Ile Ile Ile Ala Leu Ala Ala Thr Phe
705                 710                 715                 720

Gly Leu Tyr Phe Val Ala Ser Phe Met Tyr Leu Asp Pro Trp His Met
                725                 730                 735

Phe Thr Ser Phe Pro Ala Tyr Met Cys Val Gln Ser Ser Tyr Ile Asn
            740                 745                 750

Ile Leu Asn Val Tyr Ala Phe Ser Asn Trp His Asp Val Ser Trp Gly
            755                 760                 765

Thr Lys Gly Ser Asp Lys Asp Ala Leu Pro Ser Ala Lys Thr Thr
770                 775                 780

Lys Asp Glu Gly Lys Glu Val Val Ile Glu Glu Ile Asp Lys Pro Gln
785                 790                 795                 800

```
Ala Asp Ile Asp Ser Gln Phe Glu Ala Thr Val Lys Arg Ala Leu Thr
            805                 810                 815

Pro Tyr Val Pro Val Glu Lys Glu Lys Thr Leu Glu Asp Ser
            820                 825                 830

Tyr Lys Ser Phe Arg Thr Arg Leu Val Thr Phe Trp Ile Phe Ser Asn
            835                 840                 845

Ala Phe Leu Ala Val Cys Ile Thr Ser Asp Gly Val Asp Lys Phe Gly
850                 855                 860

Phe Thr Asn Ser Ala Thr Asp Arg Thr Gln Arg Phe Gln Ala Leu
865                 870                 875                 880

Leu Trp Ser Asn Ala Val Ala Leu Phe Arg Phe Ile Gly Ala Cys
            885                 890                 895

Trp Phe Leu Gly Lys Thr Gly Leu Met Cys Cys Phe Ala Arg Arg
            900                 905                 910

<210> SEQ ID NO 26
<211> LENGTH: 916
<212> TYPE: PRT
<213> ORGANISM: Aspergillus nidulans

<400> SEQUENCE: 26

Met Ala Tyr His Gly Ser Gly Pro Gln Ser Pro Gly Glu His Thr Tyr
1               5                   10                  15

Asp Asp Gly His Gln Leu Arg Asp Leu Ser His Ser Asn Thr Ser Tyr
            20                  25                  30

Glu Glu Glu Ala Ser His Gly Leu Leu Ser Ser Gln Gln Ser Pro Phe
        35                  40                  45

Ala Gly Pro Phe Asp Asp Pro His Gln Gln Arg Gly Leu Thr Ala Ser
    50                  55                  60

Pro Val Gln Arg Pro Thr Ser Gly Tyr Ser Leu Thr Glu Ser Tyr Ala
65                  70                  75                  80

Pro Asp Ala Ala Tyr His Asp Pro Tyr Ser Ala Asn Gln Ser Val Tyr
                85                  90                  95

Ser Gly His Ser Glu Asn Pro Ala Ala Ala Phe Gly Val Pro Gly Arg
            100                 105                 110

Val Ala Ser Pro Tyr Ala Arg Ser Glu Thr Ser Ser Thr Glu Ala Trp
        115                 120                 125

Arg Gln Arg Gln Ala Gly Ala Arg Gly Gly Asn Gly Leu Arg Arg
    130                 135                 140

Tyr Ala Thr Arg Lys Val Lys Leu Val Gln Gly Ser Val Leu Ser Val
145                 150                 155                 160

Asp Tyr Pro Val Pro Ser Ala Ile Gln Asn Ala Ile Gln Ala Lys Tyr
                165                 170                 175

Arg Asn Asp Leu Glu Gly Gly Ser Glu Glu Phe Thr His Met Arg Tyr
            180                 185                 190

Thr Ala Ala Thr Cys Asp Pro Asn Glu Phe Thr Leu His Asn Gly Tyr
        195                 200                 205

Asn Leu Arg Pro Ala Met Tyr Asn Arg His Thr Glu Leu Leu Ile Ala
    210                 215                 220

Ile Thr Tyr Tyr Asn Glu Asp Lys Thr Leu Thr Ala Arg Thr Leu His
225                 230                 235                 240

Gly Val Met Gln Asn Ile Arg Asp Ile Val Asn Leu Lys Lys Ser Glu
                245                 250                 255

Phe Trp Asn Lys Gly Gly Pro Ala Trp Gln Lys Ile Val Val Cys Leu
            260                 265                 270
```

```
Val Phe Asp Gly Ile Asp Pro Cys Asp Lys Asp Thr Leu Asp Val Leu
            275                 280                 285

Ala Thr Val Gly Ile Tyr Gln Asp Gly Val Met Lys Arg Asp Val Asp
        290                 295                 300

Gly Lys Glu Thr Val Ala His Ile Phe Glu Tyr Thr Thr Gln Leu Ser
305                 310                 315                 320

Val Thr Pro Asn Gln Gln Leu Ile Arg Pro Thr Asp Asp Gly Pro Ser
                325                 330                 335

Thr Leu Pro Pro Val Gln Met Met Phe Cys Leu Lys Gln Lys Asn Ser
            340                 345                 350

Lys Lys Ile Asn Ser His Arg Trp Leu Phe Asn Ala Phe Gly Arg Ile
        355                 360                 365

Leu Asn Pro Glu Val Cys Ile Leu Leu Asp Ala Thr Lys Pro Gly
                370                 375                 380

Pro Lys Ser Leu Leu Tyr Leu Trp Glu Ala Phe Tyr Asn Asp Lys Asp
385                 390                 395                 400

Leu Gly Gly Ala Cys Gly Glu Ile His Ala Met Leu Gly Lys Gly Trp
                405                 410                 415

Lys Lys Leu Leu Asn Pro Leu Val Ala Ala Gln Asn Phe Glu Tyr Lys
            420                 425                 430

Ile Ser Asn Ile Leu Asp Lys Pro Leu Glu Ser Ser Phe Gly Tyr Val
        435                 440                 445

Ser Val Leu Pro Gly Ala Phe Ser Ala Tyr Arg Phe Arg Ala Ile Met
    450                 455                 460

Gly Arg Pro Leu Glu Gln Tyr Phe His Gly Asp His Thr Leu Ser Lys
465                 470                 475                 480

Gln Leu Gly Lys Lys Gly Ile Glu Gly Met Asn Ile Phe Lys Lys Asn
                485                 490                 495

Met Phe Leu Ala Glu Asp Arg Ile Leu Cys Phe Glu Leu Val Ala Lys
            500                 505                 510

Ala Gly Ser Lys Trp His Leu Ser Tyr Val Lys Ala Ser Lys Gly Glu
        515                 520                 525

Thr Asp Val Pro Glu Gly Ala Pro Glu Phe Ile Ser Gln Arg Arg Arg
    530                 535                 540

Trp Leu Asn Gly Ser Phe Ala Ala Gly Ile Tyr Ser Leu Met His Phe
545                 550                 555                 560

Gly Arg Met Tyr Lys Ser Gly His Asn Ile Val Arg Met Phe Phe Leu
                565                 570                 575

His Leu Gln Met Leu Tyr Asn Trp Phe Ser Thr Phe Leu Thr Trp Phe
            580                 585                 590

Ser Leu Ala Ser Tyr Trp Leu Thr Thr Ser Val Ile Met Asp Leu Val
        595                 600                 605

Gly Thr Pro Ser Ser Asn Gly Tyr Thr Ala Phe Pro Phe Gly Lys
    610                 615                 620

Thr Ala Thr Pro Ile Ile Asn Thr Leu Val Lys Tyr Ile Tyr Leu Ala
625                 630                 635                 640

Phe Leu Leu Leu Gln Phe Ile Leu Ala Leu Gly Asn Arg Pro Lys Gly
                645                 650                 655

Ser Lys Leu Ser Tyr Leu Ala Ser Phe Val Ala Phe Gly Ile Ile Gln
            660                 665                 670

Leu Tyr Val Val Asp Ala Leu Tyr Leu Val Val Arg Ala Phe Thr
        675                 680                 685
```

-continued

```
Gly Gly Ala Pro Met Asp Phe Asn Thr Asp Asp Gly Ile Gly Ala Phe
    690             695                 700

Leu Ser Ser Phe Phe Gly Ser Ser Gly Ala Gly Ile Ile Ile Ile Ala
705             710                 715                 720

Leu Ala Ala Thr Phe Gly Leu Tyr Phe Val Ala Ser Phe Met Tyr Leu
                725                 730                 735

Asp Pro Trp His Met Phe Thr Ser Phe Pro Ala Tyr Met Ala Val Gln
                740                 745                 750

Ser Ser Tyr Ile Asn Ile Leu Asn Val Tyr Ala Phe Ser Asn Trp His
            755                 760                 765

Asp Val Ser Trp Gly Thr Lys Gly Ser Asp Lys Ala Asp Ala Leu Pro
770                 775                 780

Ser Ala Lys Thr Thr Gly Gly Lys Gly Glu Glu Ala Val Ile Glu Glu
785                 790                 795                 800

Ile Asp Lys Pro Gln Ala Asp Ile Asp Ser Gln Phe Glu Ala Thr Val
                805                 810                 815

Lys Arg Ala Leu Thr Pro Tyr Val Pro Pro Glu Glu Lys Glu Glu Lys
                820                 825                 830

Ser Leu Asp Asp Ser Tyr Lys Ser Phe Arg Thr Arg Leu Val Thr Leu
            835                 840                 845

Trp Leu Phe Ser Asn Gly Leu Leu Ala Val Cys Ile Thr Ser Glu Gly
850                 855                 860

Leu Asp Lys Phe Gly Phe Thr Asn Thr Ser Thr Glu Arg Thr Ser Arg
865                 870                 875                 880

Phe Phe Gln Ala Leu Leu Trp Ser Asn Ala Val Val Ala Leu Ile Arg
                885                 890                 895

Phe Ile Gly Ala Thr Trp Phe Leu Gly Lys Thr Gly Leu Leu Cys Cys
                900                 905                 910

Phe Ala Arg Arg
            915
```

```
<210> SEQ ID NO 27
<211> LENGTH: 927
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (8)..(8)
<223> OTHER INFORMATION: x=gly, ser, pro or no amino acid
<220> FEATURE:
<221> NAME/KEY: MISC_FEATURE
<222> LOCATION: (15)..(15)
<223> OTHER INFORMATION: x=tyr, thr or no amino acid
<220> FEATURE:
<221> NAME/KEY: MISC_FEATURE
<222> LOCATION: (16)..(16)
<223> OTHER INFORMATION: x=asp, tyr or no amino acid
<220> FEATURE:
<221> NAME/KEY: MISC_FEATURE
<222> LOCATION: (18)..(18)
<223> OTHER INFORMATION: x=asp or asn
<220> FEATURE:
<221> NAME/KEY: MISC_FEATURE
<222> LOCATION: (25)..(25)
<223> OTHER INFORMATION: x-leu or met
<220> FEATURE:
<221> NAME/KEY: MISC_FEATURE
<222> LOCATION: (28)..(28)
<223> OTHER INFORMATION: x=ser, gly, asn or no amino acid
<220> FEATURE:
<221> NAME/KEY: MISC_FEATURE
<222> LOCATION: (33)..(33)
```

-continued

```
<223> OTHER INFORMATION: x=his, asn or no amino acid
<220> FEATURE:
<221> NAME/KEY: MISC_FEATURE
<222> LOCATION: (36)..(36)
<223> OTHER INFORMATION: x=ala, gln or no amino acid
<220> FEATURE:
<221> NAME/KEY: MISC_FEATURE
<222> LOCATION: (37)..(37)
<223> OTHER INFORMATION: x=glu or asp
<220> FEATURE:
<221> NAME/KEY: MISC_FEATURE
<222> LOCATION: (38)..(38)
<223> OTHER INFORMATION: x=his, asp or glu
<220> FEATURE:
<221> NAME/KEY: MISC_FEATURE
<222> LOCATION: (39)..(39)
<223> OTHER INFORMATION: x=glu or asp
<220> FEATURE:
<221> NAME/KEY: MISC_FEATURE
<222> LOCATION: (46)..(46)
<223> OTHER INFORMATION: x=ser, his or no amino acid
<220> FEATURE:
<221> NAME/KEY: MISC_FEATURE
<222> LOCATION: (47)..(47)
<223> OTHER INFORMATION: x=ser, his, gln or no amino acid
<220> FEATURE:
<221> NAME/KEY: MISC_FEATURE
<222> LOCATION: (48)..(48)
<223> OTHER INFORMATION: x=asn or gln
<220> FEATURE:
<221> NAME/KEY: MISC_FEATURE
<222> LOCATION: (52)..(52)
<223> OTHER INFORMATION: x=phe or tyr
<220> FEATURE:
<221> NAME/KEY: MISC_FEATURE
<222> LOCATION: (53)..(53)
<223> OTHER INFORMATION: x=ser, gly, thr or ala
<220> FEATURE:
<221> NAME/KEY: MISC_FEATURE
<222> LOCATION: (61)..(61)
<223> OTHER INFORMATION: x=his, gln or no amino acid
<220> FEATURE:
<221> NAME/KEY: MISC_FEATURE
<222> LOCATION: (63)..(63)
<223> OTHER INFORMATION: x=his, gln, arg or no amino acid
<220> FEATURE:
<221> NAME/KEY: MISC_FEATURE
<222> LOCATION: (64)..(64)
<223> OTHER INFORMATION: x=gly or no amino acid
<220> FEATURE:
<221> NAME/KEY: MISC_FEATURE
<222> LOCATION: (65)..(65)
<223> OTHER INFORMATION: x=leu or no amino acid
<220> FEATURE:
<221> NAME/KEY: MISC_FEATURE
<222> LOCATION: (68)..(68)
<223> OTHER INFORMATION: x=ser, ala or gly
<220> FEATURE:
<221> NAME/KEY: MISC_FEATURE
<222> LOCATION: (71)..(71)
<223> OTHER INFORMATION: x=val, ala, thr or gln
<220> FEATURE:
<221> NAME/KEY: MISC_FEATURE
<222> LOCATION: (74)..(74)
<223> OTHER INFORMATION: x=pro, ala, val or thr
<220> FEATURE:
<221> NAME/KEY: MISC_FEATURE
<222> LOCATION: (86)..(86)
<223> OTHER INFORMATION: x=asp or glu
<220> FEATURE:
<221> NAME/KEY: MISC_FEATURE
<222> LOCATION: (87)..(87)
<223> OTHER INFORMATION: x=his, pro or ala
<220> FEATURE:
<221> NAME/KEY: MISC_FEATURE
<222> LOCATION: (88)..(88)
<223> OTHER INFORMATION: x=pro, gln or ala
<220> FEATURE:
<221> NAME/KEY: MISC_FEATURE
```

```
<222> LOCATION: (89)..(89)
<223> OTHER INFORMATION: x=gln, asn or tyr
<220> FEATURE:
<221> NAME/KEY: MISC_FEATURE
<222> LOCATION: (90)..(90)
<223> OTHER INFORMATION: x=ala, met or his
<220> FEATURE:
<221> NAME/KEY: MISC_FEATURE
<222> LOCATION: (91)..(91)
<223> OTHER INFORMATION: x=gln, ser or asp
<220> FEATURE:
<221> NAME/KEY: MISC_FEATURE
<222> LOCATION: (92)..(92)
<223> OTHER INFORMATION: x=asp, gln or pro
<220> FEATURE:
<221> NAME/KEY: MISC_FEATURE
<222> LOCATION: (94)..(94)
<223> OTHER INFORMATION: x=asn, thr, ser or no amino acid
<220> FEATURE:
<221> NAME/KEY: MISC_FEATURE
<222> LOCATION: (95)..(95)
<223> OTHER INFORMATION: x=asp, gln, ala or no amino acid
<220> FEATURE:
<221> NAME/KEY: MISC_FEATURE
<222> LOCATION: (97)..(97)
<223> OTHER INFORMATION: x=ser, gln or no amino acid
<220> FEATURE:
<221> NAME/KEY: MISC_FEATURE
<222> LOCATION: (98)..(98)
<223> OTHER INFORMATION: x=pro or no amino acid
<220> FEATURE:
<221> NAME/KEY: MISC_FEATURE
<222> LOCATION: (99)..(99)
<223> OTHER INFORMATION: x=gly or no amino acid
<220> FEATURE:
<221> NAME/KEY: MISC_FEATURE
<222> LOCATION: (100)..(100)
<223> OTHER INFORMATION: x=ser or no amino acid
<220> FEATURE:
<221> NAME/KEY: MISC_FEATURE
<222> LOCATION: (101)..(101)
<223> OTHER INFORMATION: x=met, val or no amino acid
<220> FEATURE:
<221> NAME/KEY: MISC_FEATURE
<222> LOCATION: (106)..(106)
<223> OTHER INFORMATION: x=met, thr or ser
<220> FEATURE:
<221> NAME/KEY: MISC_FEATURE
<222> LOCATION: (107)..(107)
<223> OTHER INFORMATION: x=ala or no amino acid
<220> FEATURE:
<221> NAME/KEY: MISC_FEATURE
<222> LOCATION: (108)..(108)
<223> OTHER INFORMATION: x=glu or asp
<220> FEATURE:
<221> NAME/KEY: MISC_FEATURE
<222> LOCATION: (125)..(125)
<223> OTHER INFORMATION: x=thr, ser or ala
<220> FEATURE:
<221> NAME/KEY: MISC_FEATURE
<222> LOCATION: (128)..(128)
<223> OTHER INFORMATION: x=glu or asp
<220> FEATURE:
<221> NAME/KEY: MISC_FEATURE
<222> LOCATION: (133)..(133)
<223> OTHER INFORMATION: x=glu or asp
<220> FEATURE:
<221> NAME/KEY: MISC_FEATURE
<222> LOCATION: (142)..(142)
<223> OTHER INFORMATION: x=gln, gly, ala or no amino acid
<220> FEATURE:
<221> NAME/KEY: MISC_FEATURE
<222> LOCATION: (143)..(143)
<223> OTHER INFORMATION: x=gly, arg or no amino acid
<220> FEATURE:
<221> NAME/KEY: MISC_FEATURE
<222> LOCATION: (144)..(144)
<223> OTHER INFORMATION: x=arg or no amino acid
<220> FEATURE:
```

```
<221> NAME/KEY: MISC_FEATURE
<222> LOCATION: (145)..(145)
<223> OTHER INFORMATION: x=gly or no amino acid
<220> FEATURE:
<221> NAME/KEY: MISC_FEATURE
<222> LOCATION: (146)..(146)
<223> OTHER INFORMATION: x=gly, pro or no amino acid
<220> FEATURE:
<221> NAME/KEY: MISC_FEATURE
<222> LOCATION: (179)..(179)
<223> OTHER INFORMATION: x=val or ile
<220> FEATURE:
<221> NAME/KEY: MISC_FEATURE
<222> LOCATION: (208)..(208)
<223> OTHER INFORMATION: x=glu or asp
<220> FEATURE:
<221> NAME/KEY: MISC_FEATURE
<222> LOCATION: (280)..(280)
<223> OTHER INFORMATION: x=val or ile
<220> FEATURE:
<221> NAME/KEY: MISC_FEATURE
<222> LOCATION: (298)..(298)
<223> OTHER INFORMATION: x=ile or val
<220> FEATURE:
<221> NAME/KEY: MISC_FEATURE
<222> LOCATION: (300)..(300)
<223> OTHER INFORMATION: x=ile or val
<220> FEATURE:
<221> NAME/KEY: MISC_FEATURE
<222> LOCATION: (316)..(316)
<223> OTHER INFORMATION: x=val or ile
<220> FEATURE:
<221> NAME/KEY: MISC_FEATURE
<222> LOCATION: (380)..(380)
<223> OTHER INFORMATION: x=ile or val
<220> FEATURE:
<221> NAME/KEY: MISC_FEATURE
<222> LOCATION: (392)..(392)
<223> OTHER INFORMATION: x=his, ser or pro
<220> FEATURE:
<221> NAME/KEY: MISC_FEATURE
<222> LOCATION: (596)..(596)
<223> OTHER INFORMATION: x=met or leu
<220> FEATURE:
<221> NAME/KEY: MISC_FEATURE
<222> LOCATION: (619)..(619)
<223> OTHER INFORMATION: x=pro or no amino acid
<220> FEATURE:
<221> NAME/KEY: MISC_FEATURE
<222> LOCATION: (620)..(620)
<223> OTHER INFORMATION: x=ala or no amino acid
<220> FEATURE:
<221> NAME/KEY: MISC_FEATURE
<222> LOCATION: (621)..(621)
<223> OTHER INFORMATION: x=pro or no amino acid
<220> FEATURE:
<221> NAME/KEY: MISC_FEATURE
<222> LOCATION: (622)..(622)
<223> OTHER INFORMATION: x=glu, ser or no amino acid
<220> FEATURE:
<221> NAME/KEY: MISC_FEATURE
<222> LOCATION: (624)..(624)
<223> OTHER INFORMATION: x=gly, gln, asn or ser
<220> FEATURE:
<221> NAME/KEY: MISC_FEATURE
<222> LOCATION: (625)..(625)
<223> OTHER INFORMATION: x=ser, glu or asn
<220> FEATURE:
<221> NAME/KEY: MISC_FEATURE
<222> LOCATION: (640)..(640)
<223> OTHER INFORMATION: x=val, leu or ile
<220> FEATURE:
<221> NAME/KEY: MISC_FEATURE
<222> LOCATION: (676)..(676)
<223> OTHER INFORMATION: x=val or ile
<220> FEATURE:
<221> NAME/KEY: MISC_FEATURE
<222> LOCATION: (681)..(681)
<223> OTHER INFORMATION: x=ile or val
```

```
<220> FEATURE:
<221> NAME/KEY: MISC_FEATURE
<222> LOCATION: (685)..(685)
<223> OTHER INFORMATION: x=ile or val
<220> FEATURE:
<221> NAME/KEY: MISC_FEATURE
<222> LOCATION: (686)..(686)
<223> OTHER INFORMATION: x=ile or val
<220> FEATURE:
<221> NAME/KEY: MISC_FEATURE
<222> LOCATION: (687)..(687)
<223> OTHER INFORMATION: x=ile or val
<220> FEATURE:
<221> NAME/KEY: MISC_FEATURE
<222> LOCATION: (690)..(690)
<223> OTHER INFORMATION: x=met or leu
<220> FEATURE:
<221> NAME/KEY: MISC_FEATURE
<222> LOCATION: (701)..(701)
<223> OTHER INFORMATION: x=thr, ser or asp
<220> FEATURE:
<221> NAME/KEY: MISC_FEATURE
<222> LOCATION: (702)..(702)
<223> OTHER INFORMATION: x=pro or no amino acid
<220> FEATURE:
<221> NAME/KEY: MISC_FEATURE
<222> LOCATION: (703)..(703)
<223> OTHER INFORMATION: x=leu, val or met
<220> FEATURE:
<221> NAME/KEY: MISC_FEATURE
<222> LOCATION: (711)..(711)
<223> OTHER INFORMATION: x=ile or val
<220> FEATURE:
<221> NAME/KEY: MISC_FEATURE
<222> LOCATION: (722)..(722)
<223> OTHER INFORMATION: x=glu, asp or ser
<220> FEATURE:
<221> NAME/KEY: MISC_FEATURE
<222> LOCATION: (728)..(728)
<223> OTHER INFORMATION: x=ile or val
<220> FEATURE:
<221> NAME/KEY: MISC_FEATURE
<222> LOCATION: (746)..(746)
<223> OTHER INFORMATION: x=leu or met
<220> FEATURE:
<221> NAME/KEY: MISC_FEATURE
<222> LOCATION: (759)..(759)
<223> OTHER INFORMATION: x=leu or met
<220> FEATURE:
<221> NAME/KEY: MISC_FEATURE
<222> LOCATION: (761)..(761)
<223> OTHER INFORMATION: x=ile or val
<220> FEATURE:
<221> NAME/KEY: MISC_FEATURE
<222> LOCATION: (803)..(803)
<223> OTHER INFORMATION: x=asp, gly, glu or lys
<220> FEATURE:
<221> NAME/KEY: MISC_FEATURE
<222> LOCATION: (834)..(834)
<223> OTHER INFORMATION: x=tyr or phe
<220> FEATURE:
<221> NAME/KEY: MISC_FEATURE
<222> LOCATION: (842)..(842)
<223> OTHER INFORMATION: x=gly, lys or glu
<220> FEATURE:
<221> NAME/KEY: MISC_FEATURE
<222> LOCATION: (846)..(846)
<223> OTHER INFORMATION: x=asp or glu
<220> FEATURE:
<221> NAME/KEY: MISC_FEATURE
<222> LOCATION: (870)..(870)
<223> OTHER INFORMATION: x=ala, leu or cys
<220> FEATURE:
<221> NAME/KEY: MISC_FEATURE
<222> LOCATION: (874)..(874)
<223> OTHER INFORMATION: x=glu or asp
<220> FEATURE:
<221> NAME/KEY: MISC_FEATURE
<222> LOCATION: (875)..(875)
```

```
<223> OTHER INFORMATION: x=asp, ser or gly
<220> FEATURE:
<221> NAME/KEY: MISC_FEATURE
<222> LOCATION: (877)..(877)
<223> OTHER INFORMATION: x=asp or asn
<220> FEATURE:
<221> NAME/KEY: MISC_FEATURE
<222> LOCATION: (884)..(884)
<223> OTHER INFORMATION: x=arg, gln, ser or thr
<220> FEATURE:
<221> NAME/KEY: MISC_FEATURE
<222> LOCATION: (890)..(890)
<223> OTHER INFORMATION: x=thr, ala, gln or ser
<220> FEATURE:
<221> NAME/KEY: MISC_FEATURE
<222> LOCATION: (891)..(891)
<223> OTHER INFORMATION: x=his, asn or arg
<220> FEATURE:
<221> NAME/KEY: MISC_FEATURE
<222> LOCATION: (893)..(893)
<223> OTHER INFORMATION: x=his, arg or gln
<220> FEATURE:
<221> NAME/KEY: misc_feature
<222> LOCATION: (894)..(894)
<223> OTHER INFORMATION: Xaa can be any naturally occurring amino acid
<220> FEATURE:
<221> NAME/KEY: MISC_FEATURE
<222> LOCATION: (921)..(921)
<223> OTHER INFORMATION: x=met or leu

<400> SEQUENCE: 27

Met Ala Tyr Gln Gly Ser Gly Xaa Asn Ser Pro Gly Gly Tyr Xaa Xaa
 1               5                  10                  15

Gly Xaa Gly His Arg Leu Gln Asp Xaa Pro Ser Xaa Gly Ser Gln Tyr
            20                  25                  30

Xaa Leu Pro Xaa Xaa Xaa Xaa Ala Ser Arg Ser Leu Leu Xaa Xaa Xaa
        35                  40                  45

Gln Gly Pro Xaa Xaa Gly Pro Phe Asp Asp Pro Gln Xaa His Xaa Xaa
    50                  55                  60

Xaa Arg Gly Xaa Ser Pro Xaa Arg Pro Xaa Ser Arg Tyr Ser Leu Thr
65                  70                  75                  80

Glu Ser Tyr Ala Thr Xaa Xaa Xaa Xaa Xaa Xaa Xaa Tyr Xaa Xaa Pro
                85                  90                  95

Xaa Xaa Xaa Xaa Xaa Tyr Gly Gly Gln Xaa Xaa Xaa Asn Pro Ala Ala
            100                 105                 110

Gly Phe Gly Val Pro Gly Arg Val Ala Ser Pro Tyr Xaa Arg Ser Xaa
        115                 120                 125

Thr Ser Ser Thr Xaa Ala Trp Arg Gln Arg Gln Ala Pro Xaa Xaa Xaa
    130                 135                 140

Xaa Xaa Gly Asn Leu Arg Arg Tyr Ala Thr Arg Lys Val Lys Leu Val
145                 150                 155                 160

Gln Gly Ser Val Leu Ser Val Asp Tyr Pro Val Pro Ser Ala Ile Gln
                165                 170                 175

Asn Ala Xaa Gln Ala Lys Tyr Arg Asn Asp Leu Glu Gly Gly Ser Glu
            180                 185                 190

Glu Phe Thr His Met Arg Tyr Thr Ala Ala Thr Cys Asp Pro Asn Xaa
        195                 200                 205

Phe Thr Leu His Asn Gly Tyr Asn Leu Arg Pro Ala Met Tyr Asn Arg
    210                 215                 220

His Thr Glu Leu Leu Ile Ala Ile Thr Tyr Tyr Asn Glu Asp Lys Met
225                 230                 235                 240

Leu Thr Ser Arg Thr Leu His Gly Val Met Gln Asn Ile Arg Asp Ile
                245                 250                 255
```

-continued

```
Val Asn Leu Lys Lys Ser Glu Phe Trp Asn Lys Gly Pro Ala Trp
            260                 265                 270

Gln Lys Ile Val Val Cys Leu Xaa Phe Asp Gly Ile Asp Pro Cys Asp
            275                 280                 285

Lys Asp Thr Leu Asp Val Leu Ala Thr Xaa Gly Xaa Tyr Gln Asp Gly
            290                 295                 300

Val Met Lys Arg Asp Val Asp Gly Lys Glu Thr Xaa Ala His Ile Phe
305                 310                 315                 320

Glu Tyr Thr Thr Gln Leu Ser Val Thr Ala Asn Gln Gln Leu Ile Arg
                325                 330                 335

Pro His Asp Asp Gly Pro Ser Thr Leu Pro Pro Val Gln Met Met Phe
            340                 345                 350

Cys Leu Lys Gln Lys Asn Ser Lys Ile Asn Ser His Arg Trp Leu
            355                 360                 365

Phe Asn Ala Phe Gly Arg Ile Leu Asn Pro Glu Xaa Cys Ile Leu Leu
    370                 375                 380

Asp Ala Gly Thr Lys Pro Gly Xaa Lys Ser Leu Leu Ala Leu Trp Glu
385                 390                 395                 400

Ala Phe Tyr Asn Asp Lys Asp Leu Gly Gly Ser Cys Gly Glu Ile His
                405                 410                 415

Ala Met Leu Gly Lys Gly Trp Lys Asn Leu Ile Asn Pro Leu Val Ala
            420                 425                 430

Ala Gln Asn Phe Glu Tyr Lys Ile Ser Asn Ile Leu Asp Lys Pro Leu
            435                 440                 445

Glu Ser Ser Phe Gly Tyr Val Ser Val Leu Pro Gly Ala Phe Ser Ala
            450                 455                 460

Tyr Arg Phe Arg Ala Ile Met Gly Arg Pro Leu Glu Gln Tyr Phe His
465                 470                 475                 480

Gly Asp His Thr Leu Ser Lys Gln Leu Gly Pro Lys Gly Ile Glu Gly
                485                 490                 495

Met Asn Ile Phe Lys Lys Asn Met Phe Leu Ala Glu Asp Arg Ile Leu
            500                 505                 510

Cys Phe Glu Leu Val Ala Lys Ala Gly Ser Lys Trp His Leu Ser Tyr
            515                 520                 525

Val Lys Ala Ser Lys Gly Glu Thr Asp Val Pro Glu Gly Ala Pro Glu
            530                 535                 540

Phe Ile Ser Gln Arg Arg Arg Trp Leu Asn Gly Ser Phe Ala Ala Ser
545                 550                 555                 560

Ile Tyr Ser Leu Met His Phe Gly Arg Met Tyr Lys Ser Gly His Asn
                565                 570                 575

Ile Leu Arg Met Phe Phe His Ile Gln Met Leu Tyr Asn Thr Phe
            580                 585                 590

Thr Val Phe Xaa Thr Trp Phe Ala Leu Ala Ser Tyr Trp Leu Thr Thr
            595                 600                 605

Ser Val Ile Met Asp Leu Val Gly Asn Pro Xaa Xaa Xaa Xaa Ser Xaa
            610                 615                 620

Xaa Gly Gln Arg Ala Phe Pro Phe Gly Asn Thr Ala Thr Pro Ile Xaa
625                 630                 635                 640

Asn Thr Val Leu Lys Tyr Leu Tyr Leu Ala Phe Leu Leu Leu Gln Phe
                645                 650                 655

Ile Leu Ala Leu Gly Asn Arg Pro Lys Gly Ser Lys His Ser Tyr Ile
            660                 665                 670
```

```
Thr Ser Phe Xaa Val Phe Gly Ile Xaa Gln Leu Tyr Xaa Xaa Xaa Leu
        675                 680                 685

Ser Xaa Gly Leu Val Val Arg Ala Phe Ser Gly Gly Xaa Xaa Xaa Asp
    690                 695                 700

Phe Thr Thr Asp Lys Gly Xaa Gly Glu Phe Leu Lys Ser Phe Phe Gly
705                 710                 715                 720

Ser Xaa Gly Ala Gly Ile Ile Xaa Ile Ala Leu Ala Ala Thr Phe Gly
        725                 730                 735

Leu Tyr Phe Val Ala Ser Phe Met Tyr Xaa Asp Pro Trp His Met Phe
            740                 745                 750

Thr Ser Phe Pro Ala Tyr Xaa Leu Xaa Met Ser Ser Tyr Ile Asn Ile
        755                 760                 765

Leu Met Val Tyr Ala Phe Ser Asn Trp His Asp Val Ser Trp Gly Thr
    770                 775                 780

Lys Gly Ser Asp Lys Ala Asp Ala Leu Pro Ser Ala Gln Thr Thr Lys
785                 790                 795                 800

Glu Asp Xaa Gly Lys Ala Ala Val Ile Glu Glu Ile Asp Lys Pro Gln
        805                 810                 815

Ala Asp Ile Asp Ser Gln Phe Glu Ala Thr Val Lys Arg Ala Leu Thr
            820                 825                 830

Pro Xaa Val Glu Pro Lys Val Lys Glu Xaa Lys Ser Leu Xaa Asp Ser
        835                 840                 845

Tyr Lys Ser Phe Arg Thr Arg Leu Val Thr Leu Trp Ile Phe Ser Asn
    850                 855                 860

Ala Leu Leu Ala Val Xaa Ile Thr Ser Xaa Xaa Val Xaa Lys Phe Gly
865                 870                 875                 880

Phe Thr Ser Xaa Ala Thr Asp Arg Thr Xaa Xaa Phe Phe Xaa Ala Leu
            885                 890                 895

Leu Trp Ala Thr Ala Ala Leu Ser Leu Ile Arg Phe Ile Gly Ala Cys
            900                 905                 910

Trp Phe Leu Gly Lys Thr Gly Ile Xaa Cys Cys Phe Ala Arg Arg
        915                 920                 925
```

HISTOPLASMA CAPSULATUM CHITIN SYNTHASE SEQUENCES AND THEIR USE FOR DETECTION OF HISTOPLASMA CAPSULATUM AND HISTOPLASMOSIS

PRIORITY CLAIM

This application claims priority to U.S. Provisional application 60/428,135, filed Nov. 21, 2002. The disclosure of U.S. Provisional application 60/428,135, is hereby incorporated by reference in its entirety.

FEDERAL FUNDING

The studies described herein were supported at least in part by a Merit Review administered through the Department of Veterans Affairs, a Walker Research Endowment Award, and Pilot Study Grant from the University of Arkansas. Thus, the Federal government may have rights in this invention.

FIELD OF THE INVENTION

The present invention relates generally to compositions and methods for the detection of *Histoplasma capsulatum* and the treatment of histoplasmosis.

BACKGROUND OF THE INVENTION

*Histoplasma capsulatum* is a dimorphic fungal pathogen capable of causing acute pulmonary disease in otherwise healthy individuals and lethal disease in immunocompromised humans (Ampel, 1996, *Emerg. Infect. Dis.*, 2: 109–116; Eissenberg, 1994, *The Interplay Between Histoplasma Capsulatum and Its Host Cells*, Vol, I, Ch. 6, W. B. Saunders Company, Ltd. London, UK; Wheat et al., 1985, *Am. J. Med.*, 78: 203–210). In its most serious form, the infection disseminates throughout the body. Disseminated histoplasmosis, coinciding with laboratory evidence of HIV infection, is regarded sufficient for a diagnosis of AIDS (Castro et al., 1992, *MMRW* 41: 1–14). Although AIDS currently represents the most prevalent immunocompromising disease of humans, a variety of other conditions or medical treatments can impair the human immune system and create susceptibility to diseases caused by the primary pathogen *H. capsulatum* and associated opportunistic pathogens (Goodwin et al., 1981, Medicine (Baltimore) 60: 231–266). These predisposing conditions include advanced age, diabetes, cancer chemotherapy, or immunosuppression induced to prevent rejection of transplanted organs (Wheat et al., 1982, *Ann. Intern. Med.*, 96: 159–163; Davies et al., 1978, *Am. J. Med.* 64: 94–100).

In nature, *H. capsulatum* exists as a mycelium that is well-adapted for a saprotrophic mode of growth in soil (Scherr & Weaver, 1953, *Bact. Rev.* 17: 51–92). After entrance of microconidia or mycelial fragments into a mammalian host, *H. capsulatum* differentiates into budding yeast (Maresca et al., 1994, *Trends Microbiol.*, 2: 110–114). In the animal host, the fungus experiences significant host-induced or environmental stress, including heat shock, exposure to higher osmolarity, changes in pH, and oxidative stress (Deepe, 1994, *J. Lab. Clin. Med.* 123: 201–205; Eissenberg & Goldman, 1994, *The Interplay Between Histoplasma Capsulatum and Its Host Cells*, Vol, I, Ch. 6, W. B. Saunders Company, Ltd., London, UK; Newman, 1999, *Trends Microbiol.*, 7: 67–71). The ability to resist or overcome environmental or host-induced stress is likely to be important for continued growth and virulence of *H. capsulatum*. In addition, host-induced or environmental stress may trigger changes in gene expression necessary for virulence.

Most fungi share considerable similarities at the nucleic acid and/or protein level. For example, there is considerable sequence identity for fungi rRNA at the sequence level. The ability to distinguish among various fungi may be of considerable importance clinically (Kasuga, T., et al., 1999, *J. Clin Micro.*, 37: 653–663). For example, *H. capsulatum* requires different clinical treatment than other fungal pathogens (Li, R-K., et al., 2000, *Antimicrobial Agents*, 44: 1734–1736; D. K. Stein and A. M. Sugar, 1989, *Diagn. Microbiol., Infect., Dis.*, 12: 221S–228S; Ampel, 1996). In the case of individuals with AIDS, it is essential that infections resulting in disseminated histoplasmosis be rapidly diagnosed so that appropriate treatment can be undertaken to obtain the most favorable outcome. Thus, there is a need to distinguish between *H. capsulatum* and other fungi.

There is also a specific need to distinguish between *H. capsulatum* and the closely related organism, *Blastomyces dermititidis*. Although *B. dermititidis* is also an aggressive pathogen, *H. capsulatum* infection requires a different clinical treatment than infection with *B. dermititidis* (Li, R-K., et al., 2000; Ampel, 1996). Previous work indicates there is a high level of genetic similarity between *H. capsulatum* and *B. dermatitis*. For example, it has been shown that antibodies raised against *H. capsulatum* M antigen cross react with a similar sized protein in *B. dermatitidis* (Hamilton, A. J. et al., 1990, *J. Med. Vet. Mycol.*, 28: 479–485). Therefore, there is a need to identify differences at the genomic level for the development of sequence-specific assays that will be able to differentiate these two closely related organisms.

A major structural component found in fungi and plants that is lacking from many other eukaryotic cells, is a cell wall. In fungi, the cell wall performs a complex set of function (see e.g., C. A. Munro and N. A. R. Gow, 2001, *Medical Mycology*, 39 (S1), 41–53) including providing a skeletal scaffolding where important cell surface components can be docked, as well as protecting the cell from external toxic threats. Major components of the cell wall include (1-3)-β-D-glucan and chitin. The amount of chitin found in the cell wall varies widely among various species of fungi. Little is known concerning the content and biosynthesis of the chitin component of the cell wall of *H. capsulatum*, as characterization of cell wall chitin has primarily focused on *Saccharomyces cerevisiae*.

To date, six classes of chitin synthases have been identified in fungi. Class III, V, and VI chitin synthases have been found to be unique to the filamentous fungi. Functionally, class I, II, and III synthases are believed to maintain the bulk of the housekeeping synthesis activities, while the enzymes of the remaining three classes (chitin synthases IV, V, and VI) have more specialized functions. In the case of the filamentous fungi, the class III synthases are believed to be responsible for synthesizing chitin for cell wall biogenesis which occurs during filamentous growth. In many cases, elimination of a single chitin synthase gene function results in little change in phenotype. Still, for at least some double mutants, such as in the case of the chs2 and chs3 double mutant in *Wangiella dermatitidis*, loss of these chitin synthase genes is associated with a significant decrease in virulence. These two chitin synthase genes are of the class I (chs2) and III (chs3) variety, respectively. Thus, multiple gene disruptions within the first three classes of chitin synthase genes is generally associated with significant reductions in chitin content in the cell wall and can contribute to decreased levels of virulence.

Thus, there is a need for the development of methods which specifically detect *H. capsulatum* in humans. There is also a need to be able to distinguish this pathogen from other fungi, especially closely related pathogens, such as *Blastomyces dermititidis*. There is also need to distinguish a latent *H. capsulatum* infection from an ongoing case of histoplasmosis. The ability to closely monitor this disease in high risk populations will enable the development of early treatment protocols suitable for patients, such as immunosuppressed individuals, who may not be able to defend against advanced stages of infection.

SUMMARY OF THE INVENTION

The present invention is directed to the development and use of reagents for the detection of the dimorphic fungal pathogen *H. capsulatum*. Thus, the present invention recognizes the chs1 and chs2 genes in *H. capsulatum* are very similar and are often unregulated during a number of various stressful growth conditions. These two genes are of the class I and III varieties, respectively, like that found in *W. dermatitidis*. Additionally, the present invention recognizes that these genes have the potential to play a significant role in the pathogenesis of *H. capsulatum*.

For example, in an embodiment, the methods and reagents of the present invention employ different aspects of the biology of *H. capsulatum* chitin synthase 2 (Hcchs2) for the development of nucleic acid and protein-based assays. The present invention provides for both the detection of *H. capsulatum* infection, as well as the diagnosis of an active case of histoplasmosis. The methods and reagents of the present invention also provide for the differentiation of *H. capsulatum* from other fungal pathogens such as *Blastomyces dermatitidis, Aspergillus nidulans, Aspergillus fumigatus, Aspergillus niger, Emericella nidulans, Neurospora crassa, Cryptococcus neoformans, Coccidioides immitis,* and *Candida albicans*.

Thus, in one embodiment, the present invention comprises methods and compositions to enable the specific detection of the *H. capsulatum* chitin synthase 2 intron sequences as a means to detect infection with the pathogen *H. capsulatum*.

For example, in one embodiment, the present invention comprises an isolated nucleic acid for detection of *H. capsulatum* comprising:
  (a) SEQ ID NO: 1, SEQ ID NO: 2, SEQ ID NO: 3, SEQ ID NO: 4, SEQ ID NO: 5, or SEQ ID NO: 6; or
  (b) the complement of SEQ ID NO: 1, SEQ ID NO: 2, SEQ ID NO: 3, SEQ ID NO: 4, SEQ ID NO: 5, SEQ ID NO: 6; or
  (c) a fragment of SEQ ID NO: 1, SEQ ID NO: 2, SEQ ID NO: 3, SEQ ID NO: 4, SEQ ID NO: 5, SEQ ID NO: 6, or a fragment of the complement of SEQ ID NO: 1, SEQ ID NO: 2, SEQ ID NO: 3, SEQ ID NO: 4, SEQ ID NO: 5, SEQ ID NO: 6 that hybridizes under highly stringent conditions to at least one *H. capsulatum* chitin synthase intron sequence.

In another aspect, the present invention comprises an isolated nucleic acid for detection of *H. capsulatum* comprising: (a) the nucleotide sequences set forth in SEQ ID NO: 1, SEQ ID NO: 2, SEQ ID NO: 3, SEQ ID NO: 4, SEQ ID NO: 5, SEQ ID NO: 6, or any complement thereof; (b) a nucleotide sequence having at least 70% sequence identity to any one of the sequences in (a); and (c) a fragment of any one of (a) or (b). Preferably, the intron is intron 1, and the primers comprise at least one oligonucleotide having the sequence SEQ ID NO: 7 or SEQ ID NO: 8.

The present invention also comprises a method for detecting *H. capsulatum* in a sample by detection of chitin synthase intron sequences. In an embodiment, the chitin synthase is chitin synthase 2 gene. Thus, in another aspect, the present invention comprises a method for detection of *H. capsulatum* in a sample comprising the steps of: (a) providing a sample; and (b) assaying for the presence of DNA comprising at least one intron of the *H. capsulatum* chitin synthase 2 gene in the sample, wherein the presence of chitin synthase intron DNA indicates that the sample contains *H. capsulatum*. In alternate embodiments, the method may comprise detection of *H. capsulatum* chitin synthase intron DNA by hybridization or PCR. Preferably, the intron detected is intron 1 of the chitin synthase 2 gene.

The present invention also allows for the detection of an active case of histoplasmosis. In this embodiment, the present invention relies on the discovery that *H. capsulatum* chitin synthase expression is unregulated during oxidative stress. Thus, in one aspect, the present invention comprises a method for detecting an active case of histoplasmosis in a sample, comprising the steps of (a) providing a sample; and (b) assaying the sample for the presence of *H. capsulatum* chitin synthase mRNA, or any fragment thereof, wherein detection of *H. capsulatum* chitin synthase mRNA is associated with an active case of histoplasmosis.

The present invention also comprises kits for detection of *H. capsulatum*. Thus, in one aspect the present invention comprises a kit for detection of *H. capsulatum* comprising: (a) one or more containers comprising oligonucleotide primers or DNA probes comprising sequences which hybridize to at least one intron of the *H. capsulatum* chitin synthase 2 gene, and (b) at least one separate container comprising *H. capsulatum* DNA comprising chitin synthase intron DNA.

In another aspect, the present invention comprises a method for using molecular genetic techniques to provide a strain of *H. capsulatum* comprising reduced pathogenicity by preparing *H. capsulatum* in which chitin synthase gene expression is either repressed or the genomic sequence is altered such that production of functional chitin synthase protein is significantly reduced.

Also, in yet another embodiment, the present invention comprises small inhibitory RNAs which can prevent expression of *H. capsulatum* chitin synthase genes. In an embodiment, the chitin synthase gene is the chitin synthase 2 gene.

The foregoing focuses on the more important features of the invention in order that the detailed description which follows may be better understood and in order that the present contribution to the art may be better appreciated. There are, of course, additional features of the invention which will be described hereinafter and which will form the subject matter of the claims appended hereto. It is to be understood that the invention is not limited in its application to the specific details as set forth in the following description and figures. The invention is capable of other embodiments and of being practiced or carried out in various ways.

BRIEF DESCRIPTION OF THE FIGURES

FIG. 1 shows the nucleotide sequence (5' to 3') for a partial cDNA for *Histoplasma capsulatum* chitin synthase 2 enzyme in accordance with an embodiment of the present invention (SEQ ID NO: 9).

FIG. 2 shows the nucleotide sequence (5' to 3') of the *Histoplasma capsulatum* genomic DNA (SEQ ID NO: 10) including the entire chitin synthase 2 transcribed region, with introns 1, 2, 3, 4, 5 and 6 underlined, as well as approximately 2012 bp of 5' UTR (untranscribed region) and 2269 bp 3' UTR of the chitin synthase gene in accordance with an embodiment of the present invention. The start codon at 2088 (ATG) and the stop codon (TAG) for the protein are shown in bold/italicized font. Putative start and stop nucleotides for the mRNA are shown as single nucleotides in bold font.

FIG. 3 illustrates the sequences (5' to 3') of intron 1 (SEQ ID NO: 1), intron 2 (SEQ ID NO: 2), intron 3 (SEQ ID NO: 3), intron 4 (SEQ ID NO: 4), intron 5 (SEQ ID NO: 5), and intron 6 (SEQ ID NO: 6) of the *Histoplasma capsulatum* chitin synthase 2 gene, as well as the location of each intron in the gene, in accordance with an embodiment of the present invention, wherein sequences are shown 5' to 3'.

FIG. 4 shows the sequence for *H. capsulatum* chitin synthase 2 polypeptide (SEQ ID NO: 23) in accordance with an embodiment of the present invention.

FIG. 6 shows the sequences of a pair of primers (SEQ ID NO: 7 and SEQ ID NO: 8) used in amplify chitin synthase 2 intron 1 in accordance with an embodiment of the present invention. The position of the primers is shown as underlined sequence in SEQ ID NO: 1.

DETAILED DESCRIPTION

Figure 5:
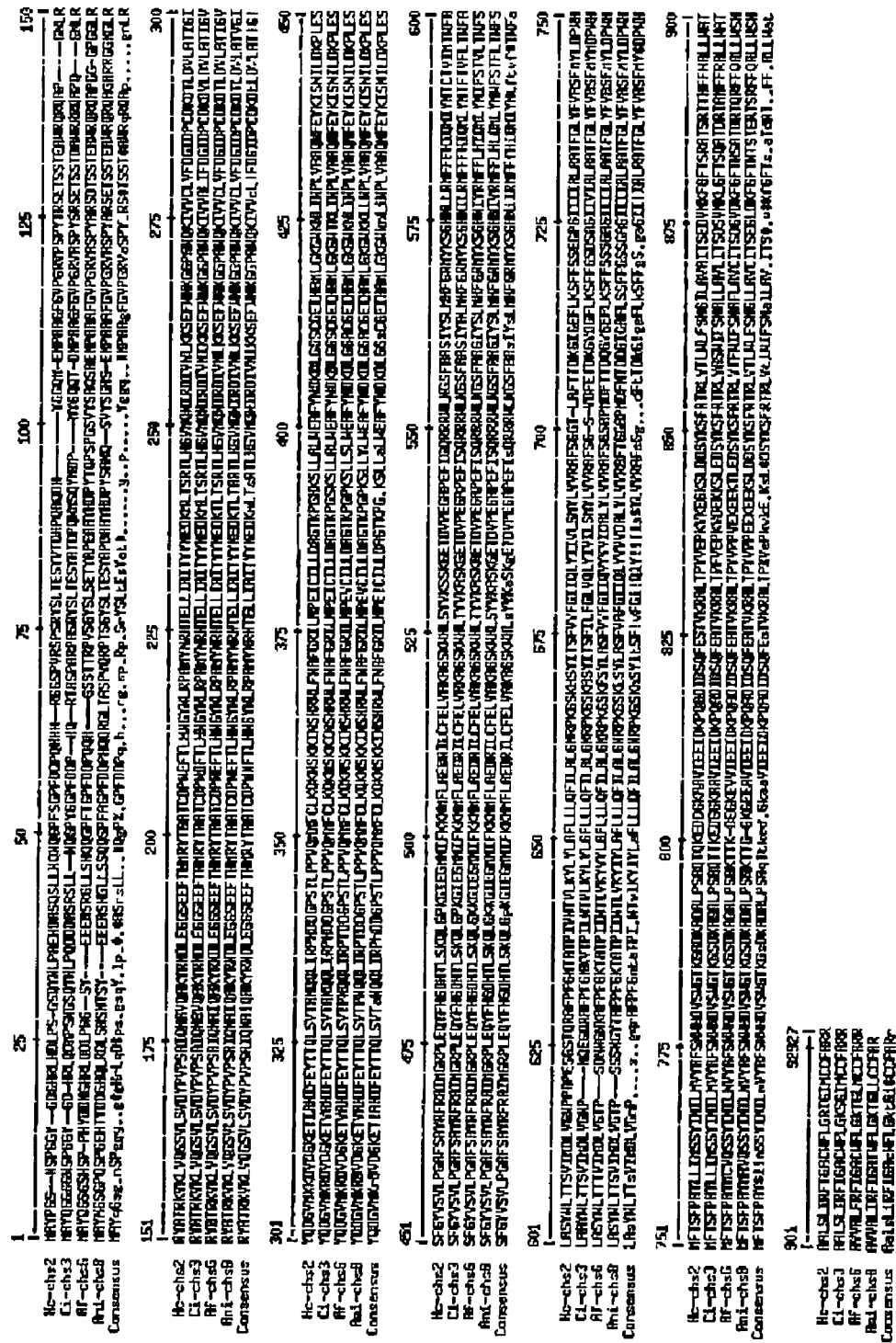
FIG. 5 illustrates an alignment of *H. capsulatum* chitin synthase 2 polypeptide (Hcchs2) (SEQ ID NO: 23) with chitin synthase proteins from *Coccidioides immitis* (Ci) (SEQ ID NO: 24), *Aspergillus fumigatus* (Af) (SEQ ID NO: 25), and *Aspergillus nidulans* (Ani) (SEQ ID NO: 26). Also shown is the consensus sequence (SEQ ID NO: 27). The Multalin program using the default settings provided on the website (Multiple sequence alignment with hierarchical clustering, F. Corpet, 1988, *Nucl. Acids Res.* 16(22), 10881–10890; (available over the internet. Settings for symbol comparisons are described in S. Henikoff and J. G. Henikoff (1992, *Proc. Natl. Acad. Sci. USA*, 89, 10915–10919) using the original Blosum62 settings with a value of 4 added to each entry to be non-negative. The gap penalties (also the default settings as provided on the web site) are subtracted to the alignment score of 2 clusters each time a new gap is inserted in a cluster. The penalty is length dependent: it is the sum of "penalty at gap opening" and of "penalty of gap extension" times the gap length; both values must be non-negative; the maximum for both values being 255. The similarity score is equal to the sum of the values of the matches (each match scored with the scoring table) less the gap penalties. The gap penalty is charged for every internal gap. By default, no penalty is charged for terminal gaps.

The present invention relies on the discovery that intron sequences for the *H. capsulatum* chitin synthase 2 gene comprise highly specific domains, which lack significant identity with counterpart genes in other infectious pathogens and therefore, can function as specific markers for *H. capsulatum*. Thus, the invention relies on the discovery that there is at least one very large intron in the *H. capsulatum* chitin synthase 2 gene that is lacking in all other known fungal chitin synthase 2 homologous genes. Also, the human host does not have a gene for chitin synthase. The fact that the host organism lacks this gene, and the significant size of at least intron 1 (~282 bp) makes the intron sequences highly specific reagents for detection of prior or current exposure to *H. capsulatum*. In addition, the present invention relies on the discovery that the gene for chitin synthase 2 is tightly regulated and one of several genes unregulated during pathogenesis. Thus, expression of the chitin synthase (at the mRNA or protein level) can be used as a marker of histoplasmosis.

Thus, the present invention recognizes that *H. capsulatum* chitin synthase intron sequences are useful as reagents for fungal specific hybridization or polymerase chain reaction (PCR) assays for *H. capsulatum*. For example, it is usually very difficult to distinguish *H. capsulatum* and *Blastomyces dermatititis*. However, using the primers of the present invention, *H. capsulatum* can be distinguished from *B. dermatititis* and other closely related pathogens. Also, the invention provides methods to distinguish patients who have been previously exposed to *H. capsulatum* from those patients who have an active case of histoplasmosis.

Definitions

In accordance with the present invention, conventional molecular biology, microbiology, and recombinant DNA techniques may be used that will be apparent to those skilled in the relevant art. Such techniques are explained fully in the literature (see, e.g., Maniatis, Fritsch & Sambrook, "Molecular Cloning: A Laboratory Manual (1982); "DNA Cloning: A Practical Approach," Volumes I and II (D. N. Glover ed. 1985).

Therefore, as used herein, the following terms shall have the definitions set out below.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

DNA molecules may be identified by their nucleic acid sequences, which are generally presented in the 5' to 3' direction (as the coding strand), wherein 5' and 3' indicate the linkages formed between the 5'-hydroxy group of one nucleotide and the 3'-hydroxyl group of the next. For a coding-strand sequence presented in the 5'-3' direction, its complement (or non-coding strand) is the DNA strand which hybridizes to that sequence.

As used herein, the term "gene" shall mean a region of DNA encoding for the mRNA sequence that codes for a given protein/polypeptide along with elements regulating mRNA expression.

"Messenger RNA" or "mRNA" shall mean an RNA molecule that encodes for a polypeptide.

"DNA polymerase" shall mean an enzyme which catalyzes the polymerization of deoxyribonucleotide triphosphates to make DNA chains using a DNA template.

"Reverse transcriptase" shall mean an enzyme that catalyzes the polymerization of deoxy- or ribonucleotide triphosphates to make DNA or RNA chains using an RNA or DNA template.

"Complementary DNA" or "cDNA" shall mean the DNA molecule synthesized by polymerization of deoxyribonucleotides from an RNA template by an enzyme with reverse transcriptase activity.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

"Oligonucleotide", as used herein in referring to the probes or primers of the present invention, is defined as a molecule comprised of two or more deoxy- or ribonucleotides, preferably more than eight. Its exact size will depend upon many factors which, in turn, depend upon the ultimate function and use of the oligonucleotide.

"DNA fragment" includes polynucleotides and/or oligonucleotides and refers to a plurality of joined nucleotide units formed from naturally-occurring bases and cyclofuranosyl groups joined by native phosphodiester bonds. This term effectively refers to naturally-occurring species or synthetic species formed from naturally-occurring subunits. "DNA fragment" also refers to purine and pyrimidine groups and moieties which function similarly but which have non naturally-occurring portions. Thus, DNA fragments may have altered sugar moieties or inter-sugar linkages. Exemplary among these are the phosphorothioate and other sulfur containing species. They may also contain altered base units or other modifications, provided that biological activity is retained. DNA fragments may also include species that include at least some modified base forms. Thus, purines and pyrimidines other than those normally found in nature may be so employed. Similarly, modifications on the cyclofuranose portions of the nucleotide subunits may also occur as long as biological function is not eliminated by such modifications.

"Primer" shall refer to an oligonucleotide, whether occurring naturally or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used. For example, for diagnostic applications, depending on the complexity of the target sequence, the oligonucleotide primer typically contains 10–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the term "hybridization" refers generally to a technique wherein denatured RNA or DNA is combined with complementary nucleic acid sequence that is either free in solution or bound to a solid phase. As recognized by one skilled in the art, complete complementarity between the two nucleic acid sequences is not a pre-requisite for hybridization to occur. The technique is ubiquitous in molecular genetics and its use centers around the identification of particular DNA or RNA sequences within complex mixtures of nucleic acids.

As used herein, "restriction endonucleases" and "restriction enzymes" shall refer to bacterial enzymes that cleave double-stranded DNA at or near a specific nucleotide sequence.

A polypeptide refers to any peptide generated from a protein or the full-length protein itself. A polypeptide may include the full-length protein or a fragment generated by proteolytic cleavage, chemical cleavage, or other means.

As used herein, the singular forms "a", "an" and "the" include plural references unless the context clearly dictates otherwise.

Unless specifically noted otherwise, nucleotide sequences are presented 5' to 3'.

Detection of Chitin Synthase Intron Sequences

The present invention is directed to nucleic acid sequences that hybridize to the introns of the *H. capsulatum* chitin synthase gene and the use of these sequences for the detection of *H. capsulatum*. The invention capitalizes on the lack of chitin synthase sequences in the human host, as well as the specificity of chitin synthase intron sequences to distinguish *H. capsulatum* from other closely-related fungi. In this way, the chitin synthase gene sequence provides a unique and specific probe for detection of *H. capsulatum* and/or histoplamosis.

Plants and fungi share the common and unique morphology of a cell wall, although the cell walls of plants are quite different than those of fungi. While cellulose is the major component of plant cell walls, the major component of fungal cell walls are β glucans. The second most common component is chitin.

The cell wall of fungi has several functions such as, protection from the extracellular environment, stability, support for surface located enzymatic activity, and to act as a selective barrier to cellular toxins. Synthesis of chitin involves a complex pathway composed of at least three chitin synthase enzymes. One component of this complex pathway, described here, is the chitin synthase 2 gene, a class III chitin synthase. Thus, chitin, a fibrous cellulose-like polysaccharide β-linked polymer of N-acetyl-glucosamine, acts as a major exoskeleton-scaffolding component of the fungal cell wall. Notably, animal cells (such as human tissue) do not contain chitin.

Thus, in one aspect, the present invention comprises an isolated nucleic acid for detection of *H. capsulatum* comprising:

(a) SEQ ID NO: 1, SEQ ID NO: 2, SEQ ID NO: 3, SEQ ID NO: 4, SEQ ID NO: 5, or SEQ ID NO: 6; or (b) the complement of SEQ ID NO: 1, SEQ ID NO: 2, SEQ ID NO: 3, SEQ ID NO: 4, SEQ ID NO: 5, or SEQ ID NO: 6; or (c) a fragment of SEQ ID NO: 1, SEQ ID NO: 2, SEQ ID NO: 3, SEQ ID NO: 4, SEQ ID NO: 5, SEQ ID NO: 6, or a fragment of the complement of SEQ ID NO: 1, SEQ ID NO: 2, SEQ ID NO: 3, SEQ ID NO: 4, SEQ ID NO: 5, SEQ ID NO: 6 that hybridizes under highly stringent conditions to at least one *H. capsulatum* chitin synthase 2 intron sequence.

Preferably, the fragment comprises at least 8 consecutive nucleotides of SEQ ID NO: 1, SEQ ID NO: 2, SEQ ID NO: 3, SEQ ID NO: 4, SEQ ID NO: 5, or SEQ ID NO: 6, or the complement of SEQ ID NO: 1, SEQ ID NO: 2, SEQ ID NO: 3, SEQ ID NO: 4, SEQ ID NO: 5, or SEQ ID NO: 6. In an embodiment, the fragment comprises an oligonucleotide having the nucleic acid sequence SEQ ID NO: 7 or SEQ ID NO: 8.

In another aspect, the present invention comprises an isolated nucleic acid for detection of *H. capsulatum* comprising: (a) the nucleotide sequences set forth in SEQ ID NO: 1, SEQ ID NO: 2, SEQ ID NO: 3, SEQ ID NO: 4, SEQ ID NO: 5, SEQ ID NO: 6, or any complements thereof; (b) a nucleotide sequence having at least 70% sequence identity to any one of the sequences in (a); and (c) a fragment of any one of (a) or (b). Percent sequence identity is calculated using computer algorithms known in the art, including BLAST, using default parameters provided for alignment of nucleotide sequences of 20 bp or larger (S. Altschul, 1990, *J. Mol. Biol.*, 215, 403–410).

The highly specific *H. capsulatum* chitin synthase probes of the present invention can be used for detection of the pathogen in a patient. Thus, in one aspect, the present invention comprises a method for detecting *H. capsulatum* in a sample, comprising the steps of: (a) providing a sample; and (b) assaying for the presence of DNA comprising an intron of a *H. capsulatum* chitin synthase gene in said sample, wherein the presence of said chitin synthase intron DNA indicates that the sample contains *H. capsulatum*. Preferably, the intron is intron 1 of the chitin synthase 2 gene. Alternatively, other chitin synthase introns may be detected. For example, in an embodiment, intron 1 of the chitin synthase 2 gene and a second chitin synthase intron from chitin synthase 2, or one of the other *H. capsulatum* chitin synthases are detected. Or, introns from other *H. capsulatum* chitin synthase genes other than chitin synthases 2 may be detected. Also preferably, the sample is obtained from a human.

In a embodiment, the method further comprises the steps of: (a) exposing the sample under high stringency hybridization conditions to at least one isolated nucleic acid that hybridizes to at least one intron of a *H. capsulatum* chitin synthase gene; and (b) determining whether there is hybridization of the isolated nucleic acid to the sample, wherein a sample comprising *H. capsulatum* exhibits detectable hybridization and a sample lacking *H. capsulatum* does not exhibit hybridization. In an embodiment, the chitin synthase gene comprises chitin synthase 2. Preferably, the method detects intron 1 (SEQ ID NO: 1) of the chitin synthase 2 gene. Also, preferably, the isolated nucleic acid comprises: (a) the nucleotide sequences set forth in SEQ ID NO: 1, SEQ ID NO: 2, SEQ ID NO: 3, SEQ ID NO: 4, SEQ ID NO: 5, or SEQ ID NO: 6, or any complement thereof; (b) a nucleotide sequence having at least 70% sequence identity to any one of the sequences in (a); and (c) a fragment of any one of (a) or (b).

In an embodiment, the method is a PCR based method. Thus, the method may comprise the steps of: (a) conducting polymerase chain reaction (PCR) amplification using at least one nucleic acid primer that hybridizes to at least one intron of a *H. capsulatum* chitin synthase gene; and (b) determining the presence or absence of the PCR product resulting from the amplification. In an embodiment, the chitin synthase gene is chitin synthase 2. Preferably, the intron is intron 1 of the chitin synthase 2 gene, and the primers comprise at least one oligonucleotide having the sequence SEQ ID NO: 7 or SEQ ID NO: 8. Also preferably, the conditions for PCR amplification are chosen so that the PCR product of interest is generated in samples comprising *H. capsulatum* but not in samples that do not contain *H. capsulatum*.

The present invention also comprises a kit for detection of *H. capsulatum* using hybridization probes and/or PCR primers. Thus, in another aspect, the present invention comprises a kit for detecting *H. capsulatum* comprising: (a) one or more containers comprising at least one oligonucleotide primer or DNA probe comprising sequences which hybridize to at least one intron of a *H. capsulatum* chitin synthase gene; and (b) at least one separate container comprising *H. capsulatum* DNA comprising chitin synthase intron DNA that hybridizes to these primers. Preferably, the intron is intron 1 of the chitin synthase 2 gene.

Chitin Synthase Sequences As Small Inhibitory RNAs

This invention also comprises methods and compositions for reducing de novo chitin synthase expression using small inhibitory RNAs or RNA quelling. For example, in an embodiment, a strain of *H. capsulatum* that expresses wild-type levels of the chitin synthase may be transformed with a vector containing a small direct repeat of coding sequence under the regulation of a constitutive promoter.

Thus, in an embodiment, the pWU55 telomeric vector may be used for fungal transformation and a pBlueScript vector is used to construct the inhibitory expression component. In the first step, an upstream component of the *H. capsulatum* catalase B gene, from base pairs −916 to +66 with respect to the start of transcription, is ligated with the vector via a directed cloning into the EcoR I and Sal I sites. The catalase B promoter component may be obtained by PCR using a genomic template, with the primers sequences as follows: iRCATBProm5': 5'-TTTGAATTCTGATCACT-GCTTCAATGCCGAGAG-3' (SEQ ID. NO. 11) and iRCATBProm3': 5'-TTTGTCGACGGCTGGGACCCT-TCTTGAG-3' (SEQ ID NO. 12). The catalase B promoter is used because it is ubiquitously active in the cell.

The 5' primer (iRCATBProm5') may be tagged with a 5' EcoRI site followed by an internal BclI site. The 3' primer (iRCATBProm3') may be tagged with a SalI site. Next the Ura5 terminator sequence may be obtained by PCR, using the pBY33 vector as template. The amplified sequence may then be tagged with a 3'-SalI sequence and an internal BclI sequence, a 5' SalI sequence, and ligated with the 3' end of the catalase B sequence using the pBS Xho I multiple cloning site.

Next, primers derived from the coding sequence of the gene of interest are constructed to produce a product of approximately 200 bp. For example, in an embodiment, sequences of 200 bp from any location of the chitin synthase coding region (e.g., exon 1 of chitin synthase 2) may be used. The 5' primer used for amplification may be tagged with a Xho I sequence and the 3' primer may be tagged with an Apa I site. Then, the final product may be digested with Apa I and allowed to ligate. This ligation will produce the inverted repeat sequence of approximately 400 bp and can then be used as template for PCR amplification. This last product is then digested with Xho I and then ligated with the Sal I digested catalase B-Ura5 pBluescript construct. The final product is amplified by PCR using the pBS construct as template with T7 and M13 reverse sequencing primers. This reaction should produce significant amounts of the construct and so can be digested with Bcl I and then ligated with BamH I digested pWU55 vector. This resulting construct may then be used to transform the *H capsulatum* strain ura 5-21. The catalase B promoter will produce a transcript of the small inverted repeat and this small RNA stem and loop transcript will initiate the de novo RNA quelling system in a gene specific manner. The *H. capsulatum* Ura5 terminator primer sequences are as follows: HCURA5TERM-5', 5'-AAAAGTCGACCCAACTGCAAGTATTGTTAC-3' (SEQ ID NO. 13); HCURATERM-3'; 5'-AAAAGTCGACT-GATCAGGATGTGCTGTATCGCATCG-3' (SEQ ID NO: 14).

Chitin Synthase as a Marker of *H. Capsulatum* and Histoplasmosis

In an embodiment, the present invention describes the use of introns from the *H. capsulatum* chitin synthase 2 gene for detection of *H. capsulatum*. The sequences of a partial cDNA and genomic DNA sequences for the *H. capsulatum* chitin synthase gene (Hccchs2) are shown in FIGS. 1 and 2, as SEQ ID NOs: 9 and 10, respectively. The presence and locations of introns within the coding region of the *H. capsualtum* chitin synthase 2 gene has been determined by automated DNA sequencing of *H. capsulatum* genomic DNA clones. The coding region of the chitin synthase 2 gene is interrupted by 6 introns: intron 1 (282 bp) (SEQ ID NO: 1); intron 2 (91 bp) (SEQ ID NO: 2); intron 3 (78 bp) (SEQ ID NO: 3); intron 4 (109 bp) (SEQ ID NO: 4); intron 5 (149 bp) (SEQ ID NO: 5); and intron 6 (119 bp) (SEQ ID NO: 6). The introns are shown (sequentially, from beginning to end of the gene) as underlined sequences. The sequence of the chitin synthase 2 introns 1–6 are also shown in FIG. 3 as SEQ ID NOs: 1–6, respectively.

There is a high level of homology for the coding region of proteins from *H. capsulatum* as compared to proteins from other fungi. For example, there is a high homology found between *H. capsulatum* catalase A and catalase P proteins and catalase homologeus found in other fungi. There is also a high level of sequence identity for *H. capsulatum* chitin synthase protein and chitin synthases from other fungi (FIGS. 4 and 5). However, in contrast to the conservation seen in coding regions, the nucleotide sequence for the *H. capsulatum* catalase introns are not highly conserved among related fungi (Johnson et al., *Microbiology*, 148, 1129–1142, 2002). Thus, intron sequences provide a unique tool by which to identify the presence of *H. capsulatum* DNA in a sample.

In an embodiment, the intron sequences (FIG. 3) are used as hybridization probes. Because of the high specificity of *H. capsulatum* chitin synthase intron sequences, the present invention comprises a method to distinguish *H. capsulatum* from other fungal pathogens, or combinations of other fungal pathogens such as, but not limited to, *Blastomyces dermatititis, Aspergillus nidulans, Aspergillus fumigatis, Emericella nidulans, Neurospora crassa, Cryptococcus neoformans Coccidioides immitis,*and *Candida albicans*. Preferably, there is little to no cross-reactivity with DNA from other organisms. For example, in an embodiment, intron probes from *H. capsulatum* chitin synthase 2 detect DNA from *H. capsulatum* but not from all *B. dermatitis* or *C. neoformans*.

Thus, the invention comprises a method for detecting *H. capsulatum* in a patient, comprising the step of detecting nucleic acid sequences comprising at least one intron of a *H. capsulatum* chitin synthase gene. In an embodiment, the gene is chitin synthase 2. In an embodiment, intron 1 of the chitin synthase 2 gene is detected. For example, the method may include the steps of (a) obtaining a sample from a patient; (b) exposing the sample under high stringency hybridization conditions to at least one isolated nucleic acid that hybridizes to an intron of a *H. capsulatum* chitin synthase gene; (c) determining whether there is hybridization of the isolated nucleic acid to the patient sample; and (d) assessing the presence of *H. capsulatum* DNA in the sample, wherein a sample comprising *H. capsulatum* DNA will exhibit detectable hybridization and a sample lacking *H. capsulatum* DNA will not exhibit hybridization. In an embodiment, the chitin synthase is chitin synthase 2. Also in an embodiment, the method detects intron 1 of the chitin synthase 2 gene.

Hybridizations may be performed according to standard methods. *H. capsulatum* genomic DNA may be isolated by methods known to those in the art such as the protocols described by Woods et al., (Woods, J. P., et al., 1992, *Molecular Microbiology*, 6: 3603–10). DNA may be denatured and spotted on membranes or digested with restriction enzymes and electrophoresed in agarose gels for transfer by capillary blotting to a solid support (e.g. Hybond-N membrane; Amersham Pharmacia Biotech, Inc.) and hybridized to probes. For dot blotting or slot blotting, DNA is denatured and spotted onto a solid support membrane.

Hybridization conditions can be described as ranging from low to high stringency. Generally, highly stringent conditions refer to washing hybrids in low salt buffer at high temperatures. Hybridization may be to filter bound DNA using hybridization solutions standard in the art such as 0.5 M NaHPO$_4$, 7% sodium dodecyl sulfate (SDS) at 65° C., and washing in 0.25 M NaHPO$_4$, 3.5% SDS followed by washing 0.1×SSC/0.1% SDS at a temperature ranging from room temperature to 68° C. depending on the length of the probe (see e.g. Ausubel, F. M. et al., *Short Protocols in Molecular Biology*, 4$^{th}$ Ed., Chapter 2, John Wiley & Sons, N.Y). For example, a high stringency wash comprises washing in 6×SSC/0.05% sodium pyrophosphate at 37° C. for a 14 base oligonucleotide, or at 48° C. for a 17 base oligonucleotide, or at 55° C. for a 20 base oligonucleotide, or at 60° C. for a 25 base oligonucleotide, or at 65° C. for a nucleotide probe about 250 nucleotides in length. Nucleic acid probes may be labeled with radionucleotides by end-labeling with, for example, [γ-$^{32}$P]ATP, or by incorporation of radiolabeled nucleotides such as [α-$^{32}$P]dCTP by random primer labeling. Alternatively, probes may be labeled by incorporation of biotinylated or fluorescein labeled nucleotides, and the probe detected using antibodies to the label.

Figure 7:
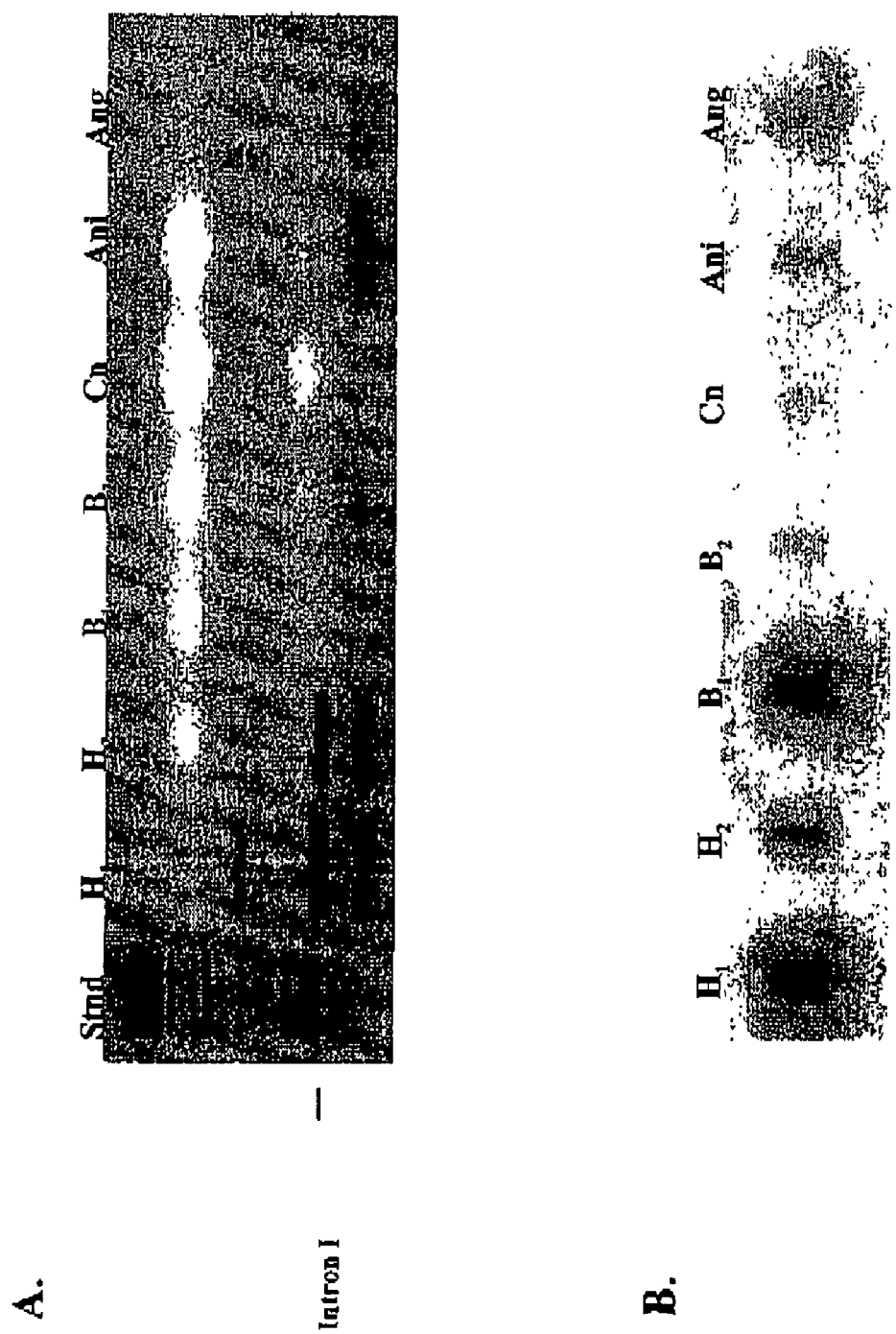
FIG. 7 shows an agarose gel of PCR products obtained using Hcchs2 specific primers with various genomic templates and the results of slot-blot hybridizations of this PCR product with this same genomic DNA from two strains of *H. capsulatum* (H1 and H2), two strains of *B. dermatitidis* (B1 and B2), and *C. neoformans* (Cn), *Aspergillus nidulans* (Ani), and *Aspergillus niger* (Ang) probed with a radiolabeled PCR product derived from *H. capsulatum* chitin synthase 2 intron 1 in accordance with an embodiment of the present invention. Hybridization of sequences from the first intron of the chitin synthase gene show specificity for *H. capsulatum*. Thus, panel (A) shows an agarose gel with products obtained from a PCR reaction using primers specific to the first intron of the *H. capsulatum* chitin synthase 2 gene (labeled as intron 1) and 300 ng of genomic DNA from various fungi as a template. Panel (B) shows the PCR product from (A), containing sequence from the first intron of the chitin synthase gene 2 of *H. capsulatum* G217B, hybridized to 3 ug of genomic DNA from various fungi. The DNA for (A) and (B) was obtained from : H1—*H. capsulatum* G217B, H2—*H. capsulatum* 2166, B1—*B. dermititi-* *dis* Woods, B2—*B. dermititidis* Green, Cn—*C. neoformans* H99, Ani—*A. nidulans* M139, and Ang—*A. niger* CBS 120–49.

Intron sequences may also be used as primers for PCR amplification of intervening *H. capsulatum* genomic DNA. Thus, oligonucleotides defined by 5'-CACTCTTTCCTAT-GTATATGC-3' (SEQ ID NO: 7) and 5'-CGATT-TAAGGGGCAAGTTAGC-3' (SEQ ID NO: 8) (FIG. 6) hybridize to chitin synthase 2 intron 1 under highly stringent conditions, as defined herein. Thus, in an embodiment, amplification with primers comprising chitin synthase 2 intron sequences results in detection of products from *H. capsulatum* DNA, but not from *B. dermatitidis* and *C. neoformans*, *A. nidulans*, or *A. niger* (FIG. 7).

Figure 8:
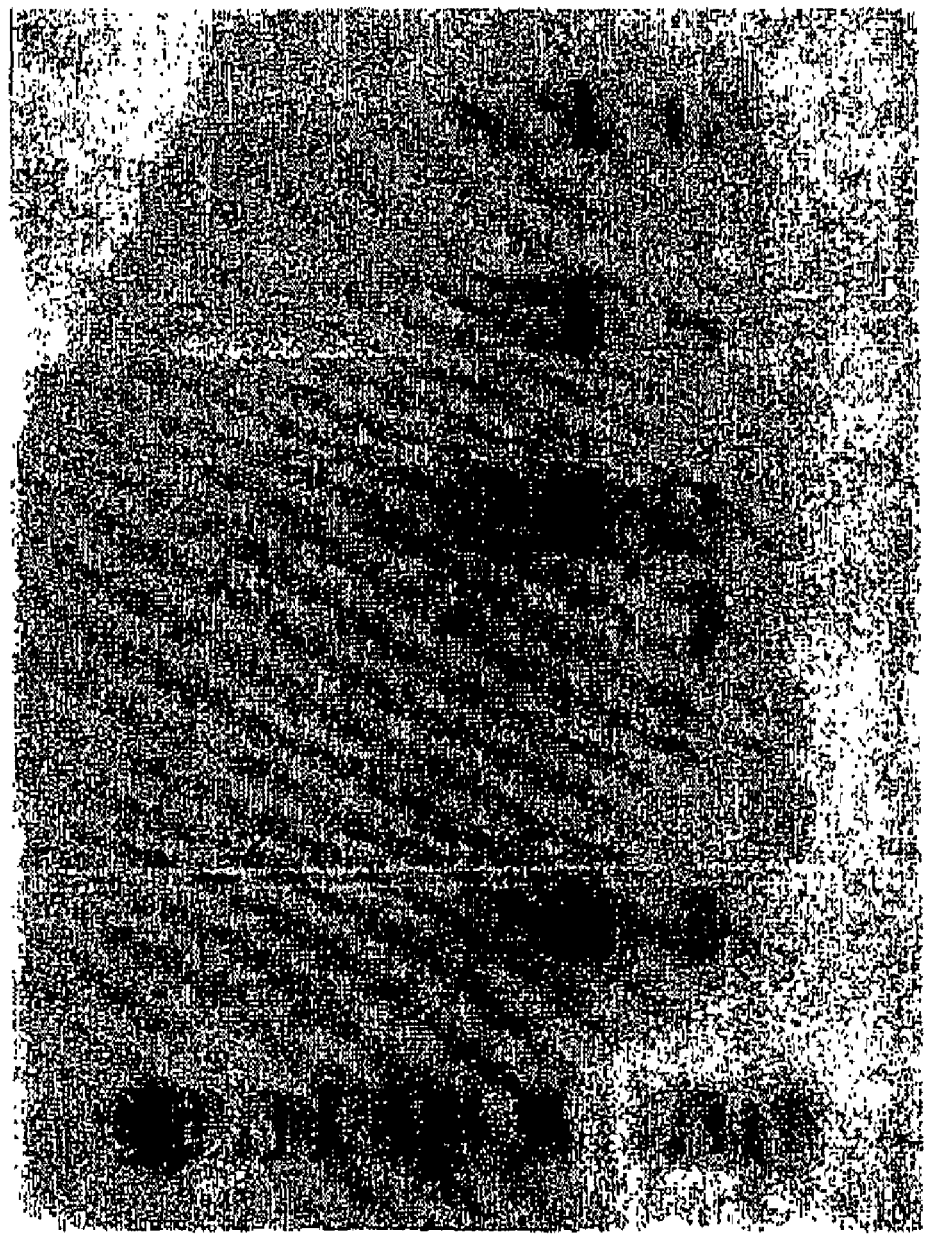
FIG. 8 illustrates a reverse transcriptase PCR (RT-PCR) experiment showing that chitin synthase 2 sequences are detected in total RNA from *H. capsulatum*-infected macrophages in accordance with an embodiment of the present invention. Primers specific for *H. capsulatum* chitin synthase 2 were used in all amplifications. Lane (1) is a 1 kb ladder; lanes 2 and 3 are PCR products using total *H. capsulatum* RNA template without and with reverse transcriptase (RT), respectively; lanes 4 and 5 uninfected macrophage total RNA (without and with RT, respectively); lanes 6–11 are RT-PCR performed with RNA isolated from macrophage cells infected with *H. capsulatum* for 30 min (lanes 6 and 7), 60 min (lanes 8 and 9), and 120 min (lanes 10 and 11) without and with RT, respectively. Samples were digested with DNAse I to remove any contaminating DNA. The larger band in lanes 3, 7, 9, and 11 are an 18S RNA normalizing control reaction, using primers specific to that gene within the same reaction tube as the Hcchs2 PCR reaction. The Hcchs2 product in lane 6, indicates incomplete Dnase I digestion of the sample. The 310 basepair Hcchs2 PCR product is indicated.

The applicability of the primer specific for *H. capsulatum* chitin synthase for detection of *H. capsulatum* in clinical samples is shown in FIG. 8, showing detection of chitin synthase sequences in macrophage cells infected with *H. capsulatum* by RT-PCR using primers specific to chitin synthase 2 exon sequences. For these experiments primers Hcchs2RT(2)5': 5'-CTACCTGTGATCCCAACGAG-3' (SEQ ID NO: 15) and Hcchs2RT(2)-3': 5'-ACGCCATC-CTGGTAGATTCC-3' (SEQ ID NO: 16) were used. Those primers hybridize to exon 3 of the chitin synthase 2 gene to produce a 310 bp (base pair) product. Thus, in an embodiment, primers specific for chitin synthase 2 (intron or exon sequences) are used to diagnose an active *H. capsulatum* infection. For example, in a human host, macrophage cells or tissue infected with *H. capsulatum* may be diagnostic of histoplasmosis.

Techniques for detection of amplified sequences include gel electrophoresis of the amplified DNA and visualization of the amplified product by ethidium bromide staining. Alternatively, the amplified DNA may be labeled by incorporation of oligonucleotide primers, which have been radiolabeled and products visualized by comparison to radiolabeled size markers by gel electrophoresis. Finally, unlabeled PCR products may be separated by gel electrophoresis, transferred to a solid matrix and products identified by hybridization of a radiolabeled probe which recognizes (i.e. is homologous to) the amplified DNA.

The amplified DNA may also be labeled by incorporation of oligonucleotide primers which have been end-labeled with a detectable chemical moiety such as, for example, biotin or fluorescein, or by incorporation of nucleotides labeled with a detectable chemical moiety such as, for example, fluorescein-dUTP, and the like. The chemically labeled products are then detected using reagents specific for that moiety. For example, PCR may be performed using primers comprising biotinylated primers specific to intron sequences from *H. capsulatum* chitin synthase 2. The amplified DNA may then be blotted to a solid support, and detected using streptavidin labeled IgG and a secondary anti-IgG antibody labeled with an enzyme, such as alkaline phosphatase, which comprises a colorimetric reaction product. The presence of the colored product provides a non-radioactive, quantitative assay for the presence of *H. capsulatum* chitin synthase 2 DNA.

In another embodiment, the nucleic acid that hybridizes to chitin synthase 2 intron DNA is arranged as a microchip or an array. In this manner, hybridization of chitin synthase 2 specific PCR products may be detected by hybridization of the PCR product to the array, as for example, by labeling the PCR product with a moiety which comprises an electrochemical, luminescent or fluorescent signal.

Figure 9A:
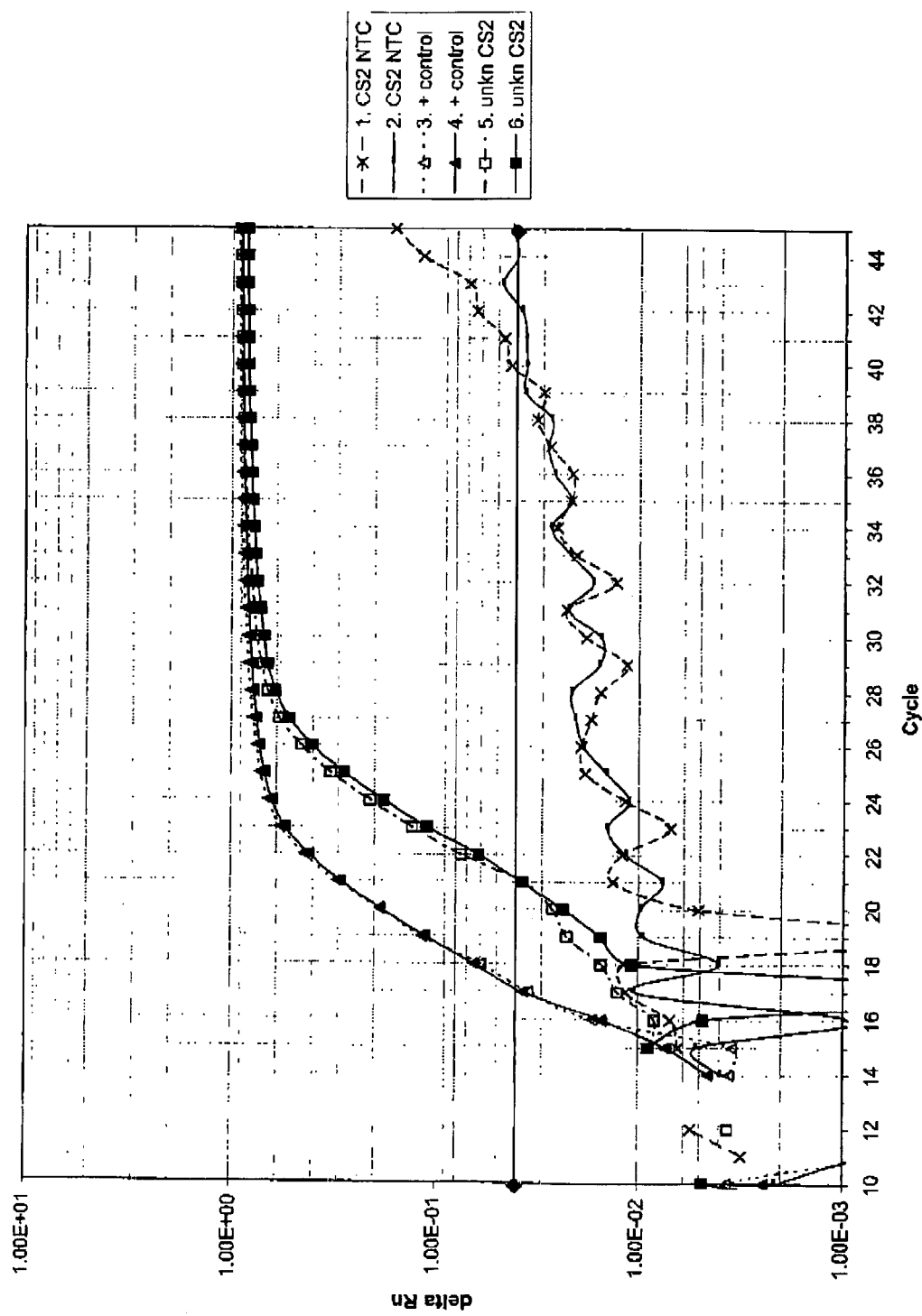
FIG. 9 illustrates real-time PCR amplification of chitin synthase 2 sequences in samples comprising *H. capsulatum* total RNA in accordance with an embodiment of the present invention. Panel (A) shows real-time products produced at each amplification cycle and panel (B) shows the actual PCR products detected on an ethidium bromide stained agarose gel. Lanes 1 and 2 are a no-template control (i.e., no RNA); lanes 3 and 4 include *H. capsulatum* purified genomic DNA template (100 ng); and lanes 5 and 6 include total RNA (including DNA contaminate) isolated from *H. capsulatum* infected macrophage cells (250 ng). RNA samples were used as template before being digested with DNAse I to remove any contaminating DNA.
Figure 9B:
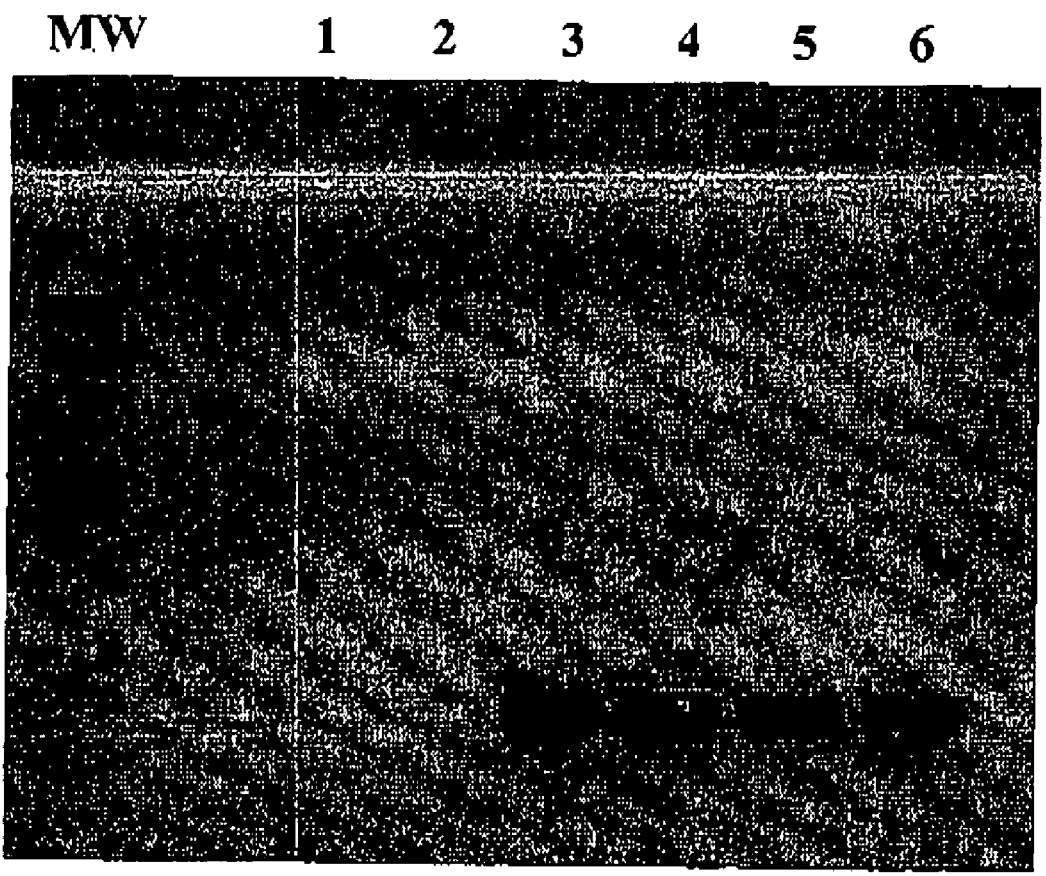

In yet another embodiment, the method comprises using real-time PCR wherein the PCR product is detected by the use of fluorescent dyes to detect the biosynthesis of products (FIG. 9). Real-time PCR uses incorporation of a fluorescent label as a means to monitor the amplification of PCR product via fluorescence resonance energy transfer (FRET) (Leutenegger, C. M., et al., 2001, *AIDS Res. Hum. Retroviruses*, 17: 243–251, Nadkarni, M. A., et al., 2002, *Microbiology*, 148: 257–266; S. J. Wall and D. R. Edwards, 2002, *Anal., Biochem.*, 300: 269–273). Commercially available thermocyclers and probes are the LightCycler and probes from Roche Applied Science, the SmartCycler from Cepheid (Sunnyvale, Calif.), the GeneAmp 5700 and Prism 7700 cyclers from Applied Biosystems (Foster City, Calif.), the iCycler iQ from BioRad (Hercules, Calif.) and probes from Molecular beacons (Cockerill, F. R., et al. 2002, *ASM News*, 68: 77–83). The methodology is adaptable to both PCR and RT-PCR techniques, and in many cases, results are obtained in less than 1 hour (see e.g., FIG. 9A, showing products at each amplification cycle). As shown in FIG. 9B, real-time PCR may be used to provide a rapid, and unequivocal detection of *H. capsulatum* infection. The PCR product for these experiments was again generated using primers Hcchs2RT(2)5': 5'-CTACCTGTGATCCCAACGAG-3' (SEQ ID NO: 15) and Hcchs2RT(2)-3': 5'-ACGCCATC- CTGGTAGATTCC-3' (SEQ ID NO: 16) that hybridize to exon 3 of the chitin synthase 2 gene to produce a 310 bp (base pair) product.

Use of Intron Sequences to Distinguish *H. capsulatum* from Closely-Related Pathogens The present invention also provides reagents which allow for distinguishing *H. capsulatum* from closely related pathogens such as *Blastomyces dermatititis, Aspergillus nidulans, Aspergillus fumigatus, Aspergillus niger, Neurospora crassa, Cryptococcus neoformans, Coccidioides immitis,* and *Candida albicans*. The assay may comprise using unique chitin synthase intron sequences as reagents in either a hybridization assay or a PCR assay. In an embodiment, sequences from the chitin synthase 2 gene are used. For example, in an embodiment, sequences from intron 1 of the chitin synthase 2 gene are used. Thus, in one aspect, the present invention comprises a method for distinguishing whether a subject has been exposed to *H. capsulatum* or at least one second pathogen comprising: (a) obtaining a sample from a subject; (b) exposing the sample under high stringency hybridization conditions to at least one isolated nucleic acid that hybridizes to at least one intron from the *H. capsulatum* chitin synthase 2 gene; (c) exposing the sample under high stringency hybridization conditions to at least one isolated nucleic acid that hybridizes to sequences from a second pathogen; (d) determining whether there is hybridization of the *H. capsulatum* chitin synthase 2 intron sequences to the sample; (e) determining whether there is hybridization of the sequences from the second pathogen to the sample; (f) assessing the presence of *H. capsulatum* in the sample, wherein a sample comprising *H. capsulatum* exhibits detectable hybridization to the *H. capsulatum* chitin synthase 2 intron sequences and a sample lacking *H. capsulatum* does not exhibit hybridization; and (g) assessing the presence of the second pathogen in the sample, wherein a sample comprising the second pathogen exhibits detectable hybridization to the sequences derived from the second pathogen and a sample lacking the second pathogen does not exhibit hybridization.

In an embodiment, the assay distinguishes *H. capsulatum* from *Blastomyces dermatititis*. In another embodiment, the assay distinguishes *H. capsulatum* from *Aspergillus nidulans, Aspergillus fumigatus, Aspergillus niger, Emericella nidulans, Neurospora crassa, Coccidioides immitis, Cryptococcus neoformans, Candida albicans,* or combinations thereof.

In an embodiment, the method further comprises a PCR-based assay comprising the steps of: (a) performing PCR using at least one isolated oligonucleotide which specifically hybridizes to intron 1 of the *H. capsulatum* chitin synthase 2 gene under conditions such that a predetermined PCR product is generated in samples comprising *H. capsulatum* but not in samples that do not contain *H. capsulatum* and determining the presence or absence of the PCR product; and (b) performing PCR using at least one isolated oligonucleotide which specifically hybridizes to DNA from the second pathogen under conditions such that a second predetermined PCR product is generated in samples comprising the second pathogen but not in samples that do not contain the second pathogen and determining the presence or absence of the PCR product. Thus, the formation of a PCR product indicates that hybridization occurred between the intron probe and the target DNA. In an embodiment, the oligonucleotide specifically hybridizes to intron 1 of the *H. capsulatum* chitin synthase gene. Also in an embodiment, the oligonucleotide comprises at least one of SEQ ID NO: 7 or SEQ ID NO: 8.

In an embodiment, the PCR assay distinguishes *H. capsulatum* from *Blastomyces dermatititis*. In another embodiment, the assay distinguishes *H. capsulatum* from *Aspergillus nidulans, Aspergillus fumigates, Aspergillus niger, Emericella nidulans, Neurospora crassa, Coccidioides immitis, Cryptococcus neoformans, Candida albicans,* or combinations thereof.

Chitin Synthase Polypeptides For Detection of *H. capsulatum*

The present invention also teaches the use of *H. capsulatum* chitin synthase polypeptide sequences for detection of *H. capsulatum*. The polypeptide sequence for *H. capsulatum* chitin synthase 2 gene is shown in FIG. 4, and an alignment of *H. capsulatum* chitin synthase 2 with chitin synthase proteins from other fungi is presented in FIG. 5. In an embodiment, assay for the chitin synthase polypeptide is effective for detection of *H. capsulatum* as there is no chitin synthase protein made by the human host. It can be seen that there is homology/identity between the chitin synthase enzymes for the various fungi. There are, however, regions of the enzyme (i.e., the N-terminal sequence) that appear to be pathogen-specific.

Thus, in another aspect, the present invention comprises a method for detecting *H. capsulatum* in a sample, comprising the steps of: (a) providing a sample; and (b) assaying for the presence *H. capsulatum* chitin synthase polypeptide in said sample, wherein a sample comprising *H. capsulatum* chitin synthase polypeptide contains *H. capsulatum*. In an embodiment, the method includes the steps of: (a) preparing the sample for immunoassay; (b) conducting an immunoassay with an antibody preparation which specifically recognizes *H. capsulatum* chitin synthase polypeptide to form an immune complex; (c) detecting the presence or absence of the immune complex; and (d) determining exposure to *H. capsulatum*, wherein the immune complex comprising the *H. capsulatum* chitin synthase polypeptide is detected in samples have been infected with *H. capsulatum* but is not detected in samples who have not been infected with *H. capsulatum*. In an embodiment, the chitin synthase polypeptide is from the chitin synthase 2 gene. In an embodiment, the sample is from a human subject.

Also, in another aspect, the present invention comprises a kit for detection of *H. capsulatum* via detection of chitin synthase 2 polypeptide. Thus, in yet another aspect, the present invention comprises a kit for *H. capsulatum* detection comprising: (a) one or more containers comprising an antibody preparation that recognizes *H. capsulatum* chitin synthase 2 polypeptide; and (b) at least one separate container comprising *H. capsulatum* chitin synthase 2 protein.

The present invention also provides an immunoassay for distinguishing *H. capsulatum* from closely related pathogens such as *C. neoformans, A. nidulans,* and *A. niger*. Thus, in another aspect, the present invention comprises a method for distinguishing whether a subject has been exposed to *H. capsulatum* or at least one second pathogen comprising the steps of: (a) obtaining a sample from the subject; (b) preparing the sample for immunoassay; (c) conducting an immunoassay with an antibody preparation which specifically recognizes *H. capsulatum* chitin synthase polypeptide; (d) conducting an immunoassay with an antibody preparation which specifically recognizes at least one polypeptide from the second pathogen; (e) detecting the presence or absence of an immune complex in steps (c) and (d); and (f)

determining exposure to *H. capsulatum* or the second pathogen, wherein an immune complex comprising *H. capsulatum* chitin synthase polypeptide is detected in subjects who have been infected with *H. capsulatum*, and wherein an immune complex comprising polypeptides from the second pathogen is detected in subjects who have been infected with the second pathogen. In an embodiment, the chitin synthase polypeptide is from the chitin synthase 2 gene.

In an embodiment, the assay distinguishes patients who have been exposed to *H. capsulatum* from patients who have been exposed to *Blastomyces dermatititis*. In an embodiment, the assay distinguishes patients who have been exposed to *H. capsulatum* from patients who have been exposed to *Cryptococcus neoformans* (Cn), *Asperfillus nidulans* (Ani), and *Aspergillus niger* (Ang), *Aspergillus fumigates, Emericella nidulans, Neurospora crassa, Coccidioides immitis*, or combinations thereof.

As described herein, the formation of an immune complex involves allowing chitin synthase polypeptide to interact with a binding partner and then measuring the formation, or lack of formation, of such a complex. For example, antibodies to chitin synthase polypeptides may be used to complex the polypeptide as an antigen-antibody complex. Complex formation may be measured in solution, or by allowing the complex to bind to a solid surface. In this aspect, chitin synthase protein may be identified and quantified by methods known in the art such as, but not limited to, staining of thin sections, immunoblot analysis, sandwich assays, solution enzyme-linked immunoassay (ELISA), radioimmunoassay (RIA), and the like.

As used herein, a carrier, solid surface, or solid phase support is a surface which is capable of immobilizing cells, cell particles or soluble proteins. The support can be washed with suitable buffers to remove non-bound components, and can be incubated with protein solutions to block non-specific binding sites. Well-known solid phase supports include glass, polypropylene, dextran, nylon, modified celluloses, polyacrylamides, and the like. Included as solid surfaces for binding reactions are microtiter wells, filter arrays, beads, dip-sticks and other suitable agents for binding assays.

Chitin synthase protein/polypeptide may be detected by immunoblotting. Immunoblotting generally comprises separation of proteins primarily by molecular weight by sodium dodecyl sulfate polyacrylamide gel electrophoresis (SDS-PAGE) and transfer of the separated proteins to a membrane. Proteins of interest can then be detected by exposing the membrane to an antibody to the protein(s), and detecting the formation of immune complexes by methods standard in the art. For example, an assay suitable for the methods of the present invention is the enzyme linked immunoassay (ELISA or EIA) where an enzyme bound to an antibody reacts with a chromogenic substrate to produce a product which can be detected, as for example by spectroscopic, fluorometric, or visual means. Enzymes which can be used to label the antibody for production of a detectable signal include alkaline phosphatase, horseradish peroxidase, glucose oxidase, catalase, glucose-6-phosphate dehydrogenases, and the like.

Alternatively, binding may be measured using microtiter wells or other types of reaction vessels. For example, microtiter wells may be pre-coated with antibody to *H. capsulatum* chitin synthase 2 polypeptide and a mixture comprising radiolabeled *H. capsulatum* chitin synthase 2 polypeptide and a homogenate from the sample of interest added. In this approach, binding of radiolabeled chitin synthase 2 polypeptide to the microtiter wells is displaced in a quantitative manner by increasing amounts of chitin synthase 2 polypeptide in the sample.

Antibodies may be commercially available or may be prepared by methods standard in the art. Thus, antibodies may include, but are not limited to, polyclonal antibodies, monoclonal antibodies (mAbs), single chain antibodies, Fab fragments, chimeric antibodies, epitope-binding fragments and the like. For example, polyclonal antibodies are a heterogeneous population of antibody molecules derived from the sera of animals immunized with the antigen of interest. Adjuvants such as Freund's (complete and incomplete), peptides, oil emulsions, lysolecithin, polyols, polyanions and the like may be used to increase the immune response.

Monoclonal antibodies are homogeneous populations of antibodies to a particular antigen, and are generally obtained by any technique which provides for production of antibody by continuous cell lines in culture. Monoclonal antibodies may be humanized, to thereby reduce interaction with unrelated epitopes by the technique of single chain antibodies (see e.g. U.S. Pat. No. 4,946,777 and Bird, *Science* 242: 423–426 (1988)).

Detection of Histoplasmosis

Only a small percentage of people with antibodies to *H. capsulatum* actually have an active case of histoplasmosis. In some cases, however, histoplasmosis can be fatal. Thus, it is important to develop a method to determine whether a patient who has been exposed to *H. capsulatum* actually has an active case of histoplasmosis. Patients having an active case of histoplasmosis mount a cellular defense against the pathogen, which includes the production of increased levels of peroxides and other oxidative agents.

In an embodiment, detecting increased *H. capsulatum* chitin synthase gene activity enables detection of organisms that are actively combating the body's defense mechanisms. For example, Northern analysis using different cDNA probes show that the *H. capsulatum* chitin synthase gene is differentially expressed during yeast phase growth or under stressful conditions induced by the host defense mechanisms.

Thus, the present invention also comprises methods to distinguish a latent *H. capsulatum* infection from active histoplasmosis. In this aspect, the present invention relies on the discovery that expression of the *H. capsulatum* chitin synthase 2 is regulated by growth conditions (FIG. 10) and markedly increased by oxidative stress (FIG. 11). Also, it has been found that *H. capsulatum* chitin synthase genes (Chs 1–5) may be unregulated under several other conditions known to exemplify the types of stress the organism may encounter (Table 1).

Thus, upon introduction into the host, fungi experience significant environmental and/or host-induced stress, including heat shock, exposure to higher osmolarity, change in pH, and oxidative stress (Deepe, 1994, *J. Lab. Clin. Med.* 123: 201–205; Eissenberg & Goldman, 1994, *The Interplay Between Histoplasma Capsulatum and Its Host Cells*, Vol, I, Ch. 6, W. B. Saunders Company, Ltd., London, UK; Newman, 1999, *Trends Microbiol.*, 7: 67–71). The ability to resist or overcome environmental or host-induced stress is likely to be important for continued growth and virulence of *H. capsulatum*. In addition, host-induced or environmental stress may trigger changes in gene expression necessary for virulence.

To evaluate the effect of such stress, cultures may be grown, in vitro, under various conditions that mimic these stressful conditions. For example, growth in the presence of paraquat and hydrogen peroxide can mimic the stress of reactive oxygen species experienced by the pathogen when entering the macrophage (the macrophage oxidative burst). Other conditions, such as altering the carbon sources of glycerol and ethanol from dextrose, can mimic the stress of growth under low carbon source availability during pathogenesis. Similarly, growth in sodium chloride can mimic conditions of osmotic shock that the pathogen may experience in the lungs during the early stages of pathogenesis. Growth at newly elevated temperatures (i.e., increasing from 37° C. to 43° C.) can mimic the temperature change experience upon inhalation of the organism into the lungs. Finally, growth in the presence of GSNO, an efficient donor of nitrous oxide (NO), creates conditions of de novo oxidative stress for the pathogen and again, mimics the conditions of the macrophage oxidative burst.

assaying for the presence of *H. capsulatum* chitin synthase polypeptide in said sample, wherein detection of *H. capsulatum* chitin synthase polypeptide is associated with an active case of histoplasmosis. Preferably, the method includes the steps of (a) preparing the sample for immunoassay; (b) conducting the immunoassay with an antibody preparation which specifically recognizes *H. capsulatum* chitin synthase polypeptide to form an immune complex; (c) detecting the presence or absence of the immune complex; and (d) determining whether the subject has an active case of histoplasmosis, wherein detection of the immune complex is associated with an active case of histoplasmosis. In an embodiment, the sample is obtained from a human. Also, as an internal control can be used. For example, an enzyme, such as *H. capsulatum* catalase P, that is constitutively expressed regardless of whether the organism is experienc-

TABLE 1

Chitin synthase gene Expression Under Conditions of Stress

| Gene | Paraquat Exposure (mM) | | | | | 4% Ethanol Exposure (min) | | | | $H_2O_2$ (mM) | | |
|------|---|---|---|---|---|---|---|---|---|---|---|---|
|      | 1 | 2 | 4 | 6 | 13 | 30 | 60 | 90 | 120 | 20 | 50 | 100 |
| Chs1 | +/− | + | + | + | + | + | + | + | + | +/− | + | + |
| Chs2 | + | + | + | 0.5+ | ++ | + | + | + | ++ | +/− | + | ++ |
| Chs3 | + | + | + | ++ | ++ | +/− | +/− | +/− | +/− | +/− | +/− | / |
| Chs4 | + | + | + | ++ | ++ | ++ | ++ | ++ | ++ | + | + | / |
| Chs5 | + | + | + | ++ | ++ | + | + | + | + | + | + | / |

| Gene | Growth/carbon | | | | 50 mM GSNO (min) | | | | Heat shock (43° C.) | | | | 1 M NaCl (min) | | | |
|------|---|---|---|---|---|---|---|---|---|---|---|---|---|---|---|---|
|      | Mycelia | | Yeast | | | | | | | | | | | | | |
|      | D | G | D | G | 30 | 60 | 90 | 120 | 20 | 40 | 60 | 80 | 30 | 60 | 90 | 120 |
| Chs1 | / | / | + | ++ | / | / | / | / | +/− | +/− | +/− | +/− | + | + | ++ | ++ |
| Chs2 | / | / | +/− | ++ | + | + | / | ++ | ++ | + | + | + | + | + | ++ | ++ |
| Chs3 | / | / | / | / | / | / | / | / | +/− | + | + | +/− | / | / | / | / |
| Chs4 | / | / | / | / | / | / | / | / | + | +/− | +/− | +/− | +/− | +/− | + | + |
| Chs5 | / | / | / | / | / | / | / | / | + | + | + | ++ | +/− | +/− | +/− | +/− |

Similar to the results found for *H. capsulatum*, the chitin synthase III gene of *Wangiella dermatitidis* is differentially expressed under different growth conditions. In addition, it has been shown that the chitin synthase I and III genes contribute to virulence in *Wangiella dermititidis*. It has also been determined that expression of these two genes is essential for proper development in *Wangiella dermititidis*. Thus, similar to the situation for *Wangiella dermatitidis*, the chitin synthase is likely to be essential to or significant to *H. capsulatum* pathogenesis. For example, chitin synthase expression may act to help the organism deter antimicrobial toxins of the macrophage oxidative burst, as expression of the gene is unregulated during the parasitic growth state (FIG. 10) and after an oxidative stress (FIG. 11). Thus, an assay for the chitin synthase protein (or mRNA) provides a means to monitor an active infection with *H. capsulatum* (i.e. histoplasmosis).

Thus, the present invention also includes a method for detecting an active case of histoplasmosis in a patient, comprising detecting the presence of *H. capsulatum* chitin synthase polypeptide. In an embodiment, the chitin synthase polypeptide is from the chitin synthase 2 gene. Thus, in one aspect, the present invention comprises a method for detecting an active case of histoplasmosis in a subject, comprising the steps of: (a) providing a sample from a subject; and (b)

ing oxidative stress (Johnson et al., 2002) may be used to quantitate the increase in chitin synthase due to oxidative stress.

The present invention also includes a method for detecting an active case of histoplasmosis in a patient comprising detecting the presence of *H. capsulatum* chitin synthase mRNA or any fragments thereof. Thus, in one aspect, the present invention comprises a method for detecting an active case of histoplasmosis in a sample, comprising the steps of: (a) providing a sample; and (b) assaying the sample for the presence of *H. capsulatum* chitin synthase mRNA or any fragment thereof wherein detection of *H. capsulatum* chitin synthase mRNA is associated with an active case of histoplasmosis. In an embodiment, the chitin synthase mRNA is chitin synthase 2 mRNA.

In an embodiment, the method may be a hybridization based assay. Thus, the method may include the steps of: (a) exposing the sample under high stringency conditions to at least one isolated nucleic acid that hybridizes to *H. capsulatum* chitin synthase mRNA or any fragment thereof; and (b) determining the levels of *H. capsulatum* chitin synthase A mRNA based on the amount of hybridization.

In an embodiment, the method may be a PCR based assay. Thus, in an embodiment, the method includes the steps of: (a) preparing *H. capsulatum* chitin synthase cDNA using mRNA from the sample as a template; (b) conducting PCR using primers that hybridize to the *H. capsulatum* chitin synthase cDNA; and (c) ascertaining the presence or absence of product, wherein detection of the amplification product is associated an active case of histoplasmosis.

For RNA based assays, total RNA may be used. For example, total RNA may be extracted from cultures of *H. capsulatum* yeast or mycelia as described above for FIG. 8 for detection of chitin synthase sequences. Thus, as described above, the applicability of the primer specific for *H. capsulatum* chitin synthase for detection of *H. capsulatum* in clinical samples is shown in FIG. 8, showing detection of chitin synthase sequences in macrophage cells infected with *H. capsulatum* by RT-PCR using primers specific to chitin synthase 2 exon 1 sequences. For these experiments primers Hcchs2RT(2)5': 5'-CTACCTGT-GATCCCAACGAG-3' (SEQ ID NO: 15) and Hcchs2RT(2)-3': 5'-ACGCCATCCTGGTAGATTCC-3' (SEQ ID NO: 16) were used. Thus, primers specific for chitin synthase 2 (intron or exon sequences) may be used to diagnose an active *H. capsulatum* infection. For example, in a human host, macrophage cells infected with *H. capsulatum* may be diagnostic of histoplamosis.

Thus, in an embodiment, mRNA is used as a template to generate chitin synthase 2 cDNA. For example, for quantitation of mRNA by RT-PCR, total or poly-A$^+$ RNA is reverse transcribed using oligo-dT primers, wherein dT is defined as deoxythymidylate. For increased specificity, the primer may is designed with 3' end which specifically hybridizes to chitin synthase mRNA.

In yet another embodiment, real-time PCR employing either total RNA or DNA template may be used. Thus, as shown in FIG. 9, real-time PCR may be used to detect *H. capsulatum* chitin synthase sequences from DNA or total RNA of *H. capsulatum*-infected macrophages. As described above, the methodology is adaptable to both PCR and RT-PCR techniques, and in many cases, results are obtained in less than 1 hour (see e.g., FIG. 9A, showing products at each amplification cycle). As shown in FIG. 9B, real-time RT-PCR may be used to provide a rapid, and unequivocal detection of *H. capsulatum* infection.

Use of Chitin Synthase Regulation to Reduce *H. Capsulatum* Pathogenicity

As described herein, similar to the situation for *Wangiella dermatitidis*, the chitin synthase is likely to be essential to *H. capsulatum* pathogenesis. For example, chitin synthase expression may aid the organism in deterring antimicrobial toxins of the macrophage oxidative burst, as expression of the gene is unregulated during the parasitic growth state (FIG. 10) and after an oxidative stress (FIG. 11). Development of molecular protocols to inhibit expression of the chitin synthase may therefore be used to reduce pathogenicity.

Thus, the present invention provides a method for using molecular genetic techniques to provide a strain of *H. capsulatum* comprising reduced pathogenicity by preparing *H. capsulatum* in which chitin synthase gene expression is either repressed or altered much that production of functional chitin synthase protein is significantly reduced. Thus, in another aspect, the present invention comprises knock-out strains of *H. capsulatum* in which chitin synthase 2 protein levels are significantly reduced. In an embodiment, the chitin synthase gene may be placed under control of a repressible promoter. Alternatively, the present invention comprises production of *H. capsulatum* strains in which chitin synthase expression is permanently repressed. In yet another embodiment, the present invention comprises production of *H. capsulatum* strains comprising a disrupted chitin synthase genomic sequence. In an embodiment, the strain comprising reduce chitin synthase protein is used to provide a vaccine.

EXAMPLES

Features and advantages of the inventive concept covered by the present invention are further illustrated by the examples which follow.

Example 1

Strains

The *H. capsulatum* virulent strain G-217B (ATCC # 26032; generously provided by W. E. Goldman, Washington University) and ATCC strain 2266 was used in all experiments. Two clinical isolate strains (the Woods strain and the Green strain) of *Blastomyces dermititidis* were also used in these experiments (generously provided by Dr. Robert Bradsher, University of Arkansas Medical Sciences). *H. capsulatum* and *B. dermititidis* cultures were grown with gentle shaking at 37° C. in 3% glycerol (v/v) or 2% dextrose (w/v) HMM medium (Worsham, P. L. et al., *J. Med. & Veterinary Mycology*, 26:137–43). YPD (1% yeast extract, 1% bacto-peptone, and 2% glucose) was used as rich medium for growth overnight at 37° C. of H99, a virulent clinical isolate of *C. neoformans* serotype A (generously provided by J. K. Lodge of St. Louis University). *Aspergillus nidulans* (strain: FGSC A4 Glasgow wild type VeA+) and *Aspergillus niger* (strain: FGSC A732 *A. niger* wild type) were obtained from the University of Kansas Fungal Genetics stock center and grown in Sabouraud's media (4% Dextrose, 1% Bacto-Peptone) for 3 days in a shaking incubator at 37° C. The *E. coli* DH5α strain or SOLAR strain (Stratagene, Inc.) were used for plasmid transformations.

Example 2

Isolation and Characterization of Chitin Synthase cDNA Clones and Introns

A cDNA library was generated with the Lambda Zap II cDNA library kit from Stratagene Inc., according to instructions of the manufacturer. To generate the cDNA library, polyA$^+$ mRNA was isolated from strain G-217B yeast phase cells which grown in HMM-gly medium. Hence, mRNAs for most yeast phase constitutively expressed genes, such as chitin synthase, were meant to be represented in the cDNA library. Approximately 10$^6$ clones were isolated from the library. This library was amplified once and stored at −70° C. in 7% (v/v) DMSO (dimethyl sulphoxide). Based on blue/white screening, more than 97% of the clones demonstrated insert sizes ranging from 0.5 to 6.4 kbp (kilobase pairs).

The Hcchs2 cDNA was originally isolated as part of a large scale screening for *H. capsulatum* catalase A cDNA using a probe that was originally designed from degenerate primers. When analyzed by DNA sequencing, however, it was found that a few of the clones contained sequences coding for chitin synthase. Initially, the degenerate radiolabeled probe was hybridized to duplicate filter lifts of bacteriophage plaques made by the cDNA library. Plaques that showed hybridization to the probe on both copies of the filter, after both the primary screening and a rescreening, were saved.

Lambda clones with large genomic fragments containing the chitin synthase gene were isolated from a *H. capsulatum* genomic library. The library was constructed by Lofstrand Labs Limited (Gaithersburg, Md.) from Sau 3A partial digestion of *H. capsulatum* genomic DNA using the Lambda FIX II/Xho I partial Fill-in Vector Kit (Stratagene of La Jolla, Calif.). The library was screened using the XL1-Blue WRA (P2) strain (Stratagene, La Jolla, Calif.). *H. capsulatum* chitin synthase cDNA clones were used for radiolabeled probe construction and library screening. Analysis of positive genomic clones was performed by DNA sequencing to confirm both the locations and the sequences of the introns for both genes.

A partial cDNA clone for chitin synthase 2 shown in FIG. 1 (SEQ ID NO: 9). The sequence for the chitin synthase gene, including introns, and upstream and downstream untranslated regions (SEQ ID NO: 10), was determined by automated sequencing of clones isolated from the genomic library and is shown in FIG. 2. The open reading frame for the chitin synthase 2 gene encodes a protein of 905 residues with a predicted molecular mass of 101,300 Daltons and a predicted pI of 8.85. A multiple sequence alignment of the *H. capsulatum* chitin synthase 2 with known fungal chitin synthases is shown in FIG. 5.

Example 3

DNA Purification and Southern/Slot Blot Analysis

*H. capsulatum* genomic DNA used for the construction of a genomic library was prepared by a modification of the protocol described by Woods et al. (Woods et al., 1992, *Mol. Microbiol.*, 6: 3603–3610) adapted to a 50 ml culture size.

Genomic DNA for all fungi used for Southern blot (or slot blot) analysis was isolated by a modification of the Pitkin et al. (Pitkin et al., 1996, *Microbiology*, 142: 1557–1565). Briefly, mycelial cultures were pelleted and the fungi lysed by vortexing and extraction with CTAB extraction buffer (100 mM Tris-HCl, pH 7.5, 700 mM NaCl, 10 mM EDTA, 1% CTAB (Hexadecyltrimethylammonium bromide), 1% β-mercaptoethanol) by incubation at 65° C. (30 min) followed by extraction with an equal volume of chloroform, and the DNA pelleted from the aqueous supernatant by adding an equal volume of isopropanol. Upon precipitation (5000 g, 10 min) the DNA is resuspended in a small volume of water, digested with Rnase A, extracted with phenol/chloroform and ethanol precipitated.

Southern blotting was performed as described by Sambrook et al., (Sambrook, et al., Molecular Cloning: A Laboratory Manual, Cold Spring Harbor Laboratory Press, 1989, Chapter 9). Digested DNA (10 μg/lane) was separated by electrophoresis through 1% agarose gels, transferred by capillary blotting to Hybond-N membrane (Amersham) and hybridized to radiolabeled probes (Sambrook et al., Chapter 9). For slot blots 3 μg DNA was denatured by boiling in 30 mM NaOH and blotted to nylon membranes with a standard vacuum slot blotter. The blot was probed with a radiolabeled probe containing the first intron of the chitin synthase 2 gene using the conditions described below.

Radiolabeled probes were constructed from PCR products containing the entire transcribed region or smaller intronic regions using the procedures described in the Random Priming Labeling Kit (Invitrogen, Carlsbad, Calif.). For example, a radiolabeled probe for intron 1 (FIG. 3) was constructed from PCR products containing the intron regions of the chitin synthase 2 gene using primers corresponding to SEQ ID NO: 7 and SEQ ID NO: 8 as primers. PCR reaction conditions were as follows: denaturation at 94° C. for 1 minute followed by 20 three-step amplification cycles of 94° C. for 20 seconds, 50° C. for 20 seconds, and 74° C. for 20 seconds with a final extension at 74° C. for 1.5 minutes.

Both Southern and slot blot hybridizations were performed in 0.5 M $NaPO_4$, pH 7 and 7% SDS Church's buffer (Church, G. M. & Gilbert, W., 1984, *Proc. Natl. Acad. Sci., USA* 81: 1991–1995) at 60° C. overnight and washed once at room temperature on a shaking platform for 30 min, in a 1:1 dilution of Church's hybridization buffer with water (Church, G. M. & Gilbert, W., 1984, *Proc. Natl. Acad. Sci., USA* 81: 1991–1995).

Example 4

RT-PCR of *H. Capsulatum* Infected Macrophage Cells

Methods have been devised in order to identify yeast infected macrophage cells. Initial experiments employed mouse RAW 264.7 macrophage cells infected with *H. capsulatum*.

Murine RAW 264.7 macrophage cells are grown overnight in DMEM medium (3% Fetal Bovine Serum and activated with 1000 U of gamma-Interferon) in a 30 ml tissue culture flask at a density of $1.0 \times 10^6$ cells. The cells were infected with *Histoplasma capsulatum* (strain G217B) at a multiplicity of infection of 10:1 yeast to macrophage cells. The infection was allowed to proceed for 1 hour and then the infected macrophage cells were washed with PBS, to remove uningested yeast, and the macrophage removed and recovered by sedimentation at 1000×g for 1 minute at 4° C. Total RNA was recovered by extraction according to Johnson et. al., 2002, *Microbiology*, 148:1129–1142.

Total RNA (1 μg) is digested with RNase free amplification grade DNase I from Invitrogen (Carlsbad, Calif.), according to the manufacturer's protocol. Then, 1 μg of total RNA is used as template in a reverse transcription reaction, to produce cDNA template, using Invitrogen Superscript II according to the manufacturer's protocol. An aliquot of 0.5 μl of the RT reaction is used in a PCR reaction as follows: 1 cycle of 1 step at 74° C. for 1 minute and 30 seconds followed by 40 cycles of 3 steps as follows: (i) 94° C. for 30 seconds; (ii): 54° C. for 20 seconds; and (iii): 74° C. for 25 seconds; followed by one cycle at 74° C. for 1 minute and 30 seconds. Reaction products were analyzed in a 1% agarose gel using standard laboratory methods.

Example 5

Real-Time PCR and RT-PCR

Real-Time RT-PCR was performed in an ABI Prism 7700 Sequence Detection System. The real-time RT-PCR protocol is identical to that described for the gel based RT-PCR (Example 4) with the following modifications: 2 μl of the RT reaction is used in the PCR reaction, as opposed to 0.5 μl, and the PCR reactions are performed using the Invitrogen Platinum Sybr Green qPCR Supermix (UDG).

For real-time PCR the amplification conditions were as follows: a single cycle of a single step at 50° C. for 2 minutes, followed by a single cycle of a single step at 95° C. for 2 minutes, which was then followed by 45 cycles of 3 steps: (i): 94° C. for 30 seconds; (ii): 54° C. for 20 seconds; and (iii): 74° C. for 25 seconds. The final step was 1 cycle at 74° C. for 1 minute and 30 seconds. Amplified products were analyzed using the Applied Biosystems Sequence Detection System Analysis Software version 1.7 supplied with the ABI 7700 Detection System.

Example 6

Regulation of *H. capsulatum* Chitin Synthase Genes in Response to Oxidative Stress and Other Types of Environmental Stress To determine if the *H. capsulatum* chitin synthase genes are differentially regulated during oxidative stress and development, the abundance of transcripts for *H. capsulatum* chitin synthase in two developmental stages (mycelia or yeast) (FIG. 10) in response to $H_2O_2$ challenge was examined (FIG. 11).

For Northern analysis, total RNA was extracted from cultures of strain G-217B yeast or mycelia according to a modification of the acid guanidinium thiocyanate extraction procedure of Chomczynski & Sacchi (1987). RNA samples (25 μg/lane) were electrophoresed in formaldehyde-1% (w/v) agarose gel (Sambrook, J., et al., *Molecular Cloning: A Laboratory Manual*, 1989, Cold Spring Harbor Laboratory Press, Plainview, N.Y.) transferred by capillary blotting to Hybond-N membrane (Amersham Pharmacia Biotech Inc.) and hybridized to radiolabeled probes in the hybridization solution of Church and Gilbert (Church, G. M. & Gilbert, W., 1984, *Proc. Natl. Acad. Sci., USA* 81: 1991–1995) according to the procedure described by Johnson and Schmidt (Johnson, C. H. & Schmidt, G. W., 1993, *Plant Mol. Biol.*, 22: 645–658). Results were obtained both by autoradiography and phosphorimaging (Molecular Dynamics Storm Phosphorimager, Amersham Pharmacia Biotech Inc., Piscataway, N.J.). Band intensities were determined from the Phosphorimager data and normalized to the band intensity of the small subunit rRNA in the same lane. Imagequant 5.1 software (Molecular Dynamics) was used for these measurements.

Figure 10:
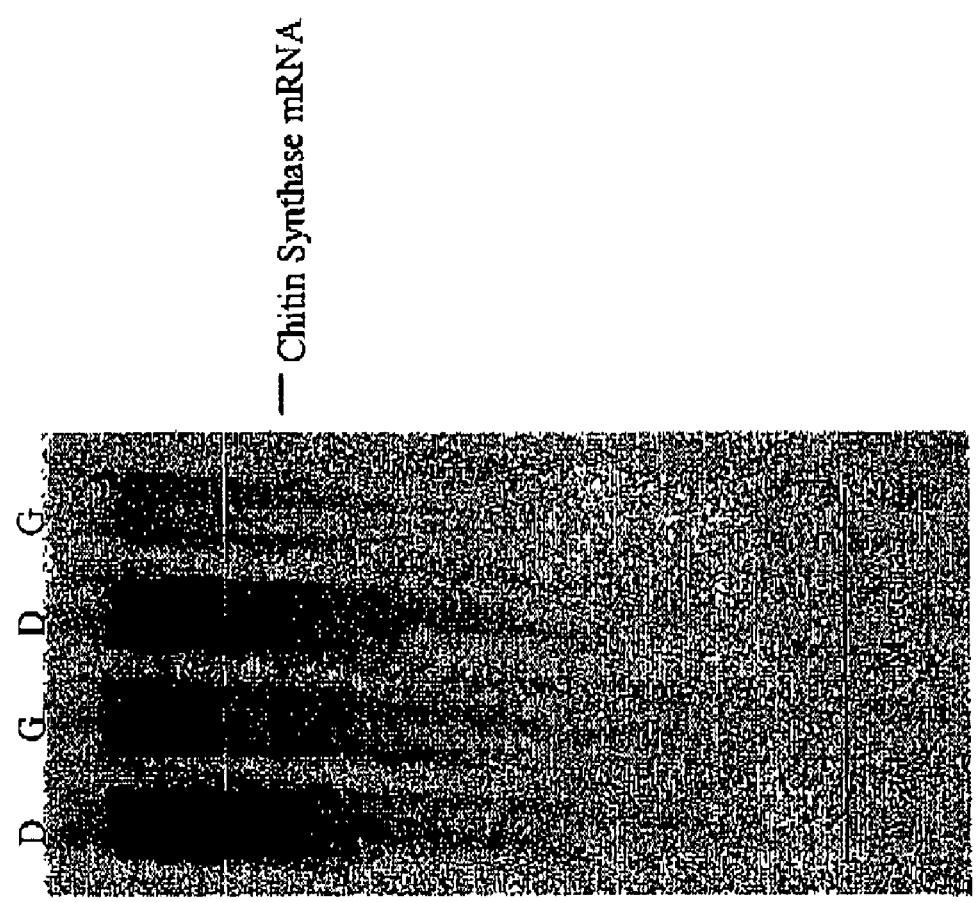
FIG. 10 illustrates expression of chitin synthase 2 in accordance with an embodiment of the present invention for *H. capsulatum* propagated under either yeast or in mycelia growth conditions using either dextrose (D) or glycerol (G) as a carbon source as shown by Northern analysis using [$^{32}$P]dCTP-labeled chitin synthase 2 probe.
Figure 11:
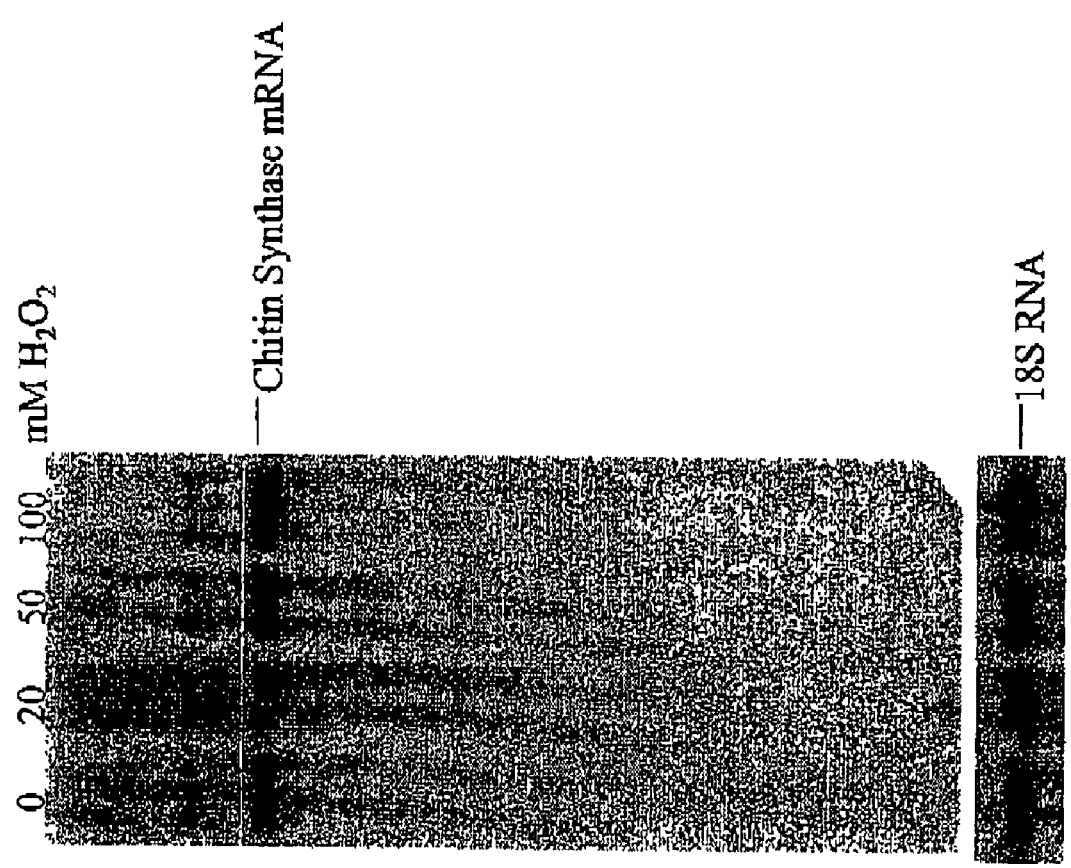
FIG. 11 illustrates expression of chitin synthase 2 in accordance with an embodiment of the present invention, after challenge with $H_2O_2$ at the concentrations indicated above each lane as shown by Northern analysis using a [$^{32}$P]dCTP-labeled chitin synthase 2 probe.

As shown in FIG. 10, chitin synthase expression is up-regulated in yeast cultures grown in glycerol (G) as compared to yeast cultures grown in dextrose (D) or mycelial cultures grown in glycerol or dextrose. Also, as shown in FIG. 11, chitin synthase mRNA is unregulated upon exposure to hydrogen peroxide ($H_2O_2$).

The effects of varying culture conditions were assessed for five chitin synthase genes in *H. capsulatum*. For the experiments shown in Table 1, the size of the cultures were 50 ml for each experiment and grown to an $OD_{600}$ of 3 or 4 in a New Brunswick shaking incubator at 150 RPMs at 37° C. The concentration of paraquat that each culture was exposed to for 1.5 hours is listed above each column. In the ethanol experiment, cultures were grown in the presence of 4% ethanol for increasing time as indicated. Cultures exposed to hydrogen peroxide were grown as described for paraquat using the concentrations indicted. Cultures were grown in the presence of 50 mM GSNO for increasing amounts of time, in minutes, as indicated. To mimic heat shock, cultures were grown at an elevated temperature for increasing amounts of time as indicated. To mimic stress due to change in osmolarity, cultures were grown in the presence of 1 M sodium chloride (NaCl) were grown for the times indicated.

The chitin synthase expression was also determined in cultures grown in both glycerol (3% v/v) and glucose (100 mM) until reaching a density of 4 or 5 $OD_{600}$. The state of growth, mycelial or yeast, and the carbon source (glucose-D, or glycerol-G) are indicated.

The cultures were recovered as described in the methods for RT-PCR and total RNA isolated as described above. Total RNA was banded by standard 1.5% agarose denaturing gel, blotted to nylon membrane and probed with chitin synthase gene specific $[P^{32}]$dCTP-radiolabeled probes. Signal quantification was performed visually.

Example 7

*H. capsulatum* Knock-Out Strain Construction

In *Histoplasma capsulatum*, construction of gene knockout stains is done by homologous gene recombination. Initially, a genomic clone of choice is isolated and the chitin synthase coding region disrupted by its replacement, in the genomic fragment, with a copy of a bacterial Hygromycin B Phosphotransferase gene under eukaryotic promoter control. This construct and the remaining upstream and downstream contiguous genomic sequence (~6 kb total for chitin synthase) is ligated with the transformation vector pWU55. Subsequently, the telomeric, uracil$^+$ pWU55 construct is linearized with Pac I endonuclease and used to transform the *H. capsulatum* strain G217B ura5-23 (a uracil auxotroph strain). Positive transformants are selected on HMM (Histoplasma macrophage media) agarose plates, due to their reversion to uracil prototrophy as a result of the presence of the pWU55 vector, and the positive transfomants used to isolate gene knock-out stains using a positive/negative selection process.

For production of *H. capsulatum* knock-out strains, sequences from the Hcchs2 gene are used to construct both 5' and 3' arms that are located upstream and downstream of the chitin synthase coding region, to be used in the construction of a knock-out vector. The following sequences are used to construct the 5' and 3' arms of the knock-out construct: For the 5' arm HcCS5'UTR(5'), 5'-AAGGAAT-TCTCTAGACCCTTGTAACCCAATGTC-3' (SEQ ID NO: 17); and HcCS5'UTR(3'), 5'-AAGGAAAAAAGCGGC-CGCCAAAACGAGAGGCTGGGTTG-3' (SEQ ID NO: 18) are used. The 5' primer is tagged with an EcoRI sequence and the 3' primer is tagged with a NotI sequence. For the 3' arm, HcCS3'UTR(5'), 5'-AAGGAAAAAAGCGGC-CGCGCTGCCGCTTGGCCAACTG-3' (SEQ ID NO: 19) and HcCS3'UTR(3'), 5'-AAGTCTAGAGACCCATCT-CAGCTCTTC-3' (SEQ ID NO: 20) are used. The 5' primer is tagged with a NotI sequence and the 3' primers is tagged with a Xba I sequence.

The products from PCR amplification, using *Histoplasma capsulatum* genomic DNA as template, are 2,500 bases for the 5' arm and 2,000 bases for the 3' arm in size. The disrupted Hcchs2 gene is constructed in the pMeca vector (Thomson, J. M., and W. A. Parrott. 1998.*Biotechniques*, 24, 922–927).

The ligations are required to be performed in a specific sequence, due to internal restriction sites, and that sequence requires that the 3' arm be ligated with pMECA first and that ligation be followed by the appropriate digestion and ligation of the 5' arm as a second step.

One of the selectable markers used in this system is the hygromycin resistance marker. *H. capsulatum* is not resistant to the antibiotic/antimycotic hygromycin B. Therefore, this gene is useful as a marker to indicate the presence of a given gene construct in a new stain after a transformation experiment. Thus, the hygromycin gene is used as both a disrupting piece of DNA within the gene of interest, in this case the Hcchs2 gene, and as a marker as an indicator of successful incorporation of the construct within the genome of a new *H. capsulatum* strain after transformation.

In this case the *E. coli* hygromycin resistance gene (hph) is fused with the constitutive promoter of the *H capsulatum* calcium binding protein and has been ligated in a vector called pMV75 (W. E. Goldman, Washington University). This vector is used as a template to produce the expressable hygromycin PCR product to ligate with the two Hcchs2 gene arms. This creates an altered form of the Hcchs2 gene whose coding region has been disrupted by the hygromycin gene marker.

Primers for amplification of the expressable hph (hygromycin resistance gene) are VM75FI: 5'-TCGACGCGGC-CGCGAGTTATACTGATGTCTG-3' (SEQ ID NO: 21), and VM75R : 5'-ATCTGCGGCCGCATTACCTCTAAA-CAAGTG-3' (SEQ ID NO: 22).

Finally, this reconstructed form of the Hcchs2 gene is removed from the vector by Xba I digestion. The disrupted form of the gene is ligated with a Spe I digested reconstructed pWU55 vector (this new form of pWU55 is termed pSpe50). Upon final construction, the knock-out construct vector is digested with Pac I, in order to linearize the vector to the telomeric form of DNA, and used to ransform the uracil minus *H. capsulatum* strain ura⁻ 5-21.

The reconstructed form of the pWU55 contains approximately 50 bp of the pMECA multiple cloning site ligated at the BamH I site of the former vector. This new form of vector was created by PCR amplification of the pMECA cloning site, using the T3 and T7 sequencing primers tagged with Bgl II restriction sequences, and after digestion with Bgl II the fragments were ligated with a BamH I digested pWU55 vector. This resulted in the construction of a *H. capsulatum* pWU55 telomeric transformation vector with a new multiple cloning region inserted at the BamH I site of the vector. In short, this inserts bases 396 to 477 of the pMECA multiple cloning site region into the pWU55 vector at the BamH I site, and results in a new vector, pSpe50.

As described above, this vector is to be used as the receiving vector for our disrupted version of the Hcchs2 gene. It can then be digested with PacI and used to transform the uracil minus form of *H capsulatum* and this strain used to select a chitin synthase minus strain.

To isolate positive transformants, the positive/negative selection process is performed as follows: A culture of the uracil prototroph strain is grown in HMM containing 50 µg/ml uracil for approximately 3 weeks. After this selection period, the culture is spread on HMM agarose containing uracil and 5-fluoroorotic acid, a compound that is toxic to uracil prototroph strains, to select for stains that have reverted to a uracil auxotrophy phenotype. During this selection for revertants, the pWU55 telomeric contract DNA may be eliminated in some cells in the initial liquid culture due to the presence of uracil in the medium. Likewise, some of the uracil auxotroph revertant strains will have replaced the functional gene with the hygromycin disrupted gene by homologous recombination, resulting in the exclusion of the rest of the pWU55 vector contents, including the uracil gene that confers the uracil prototroph phenotype. Thus, these revertant strains are hygromycin B positive (resistant strains) and URA5 gene minus (uracil auxotrophs). A number of colonies (e.g., about 6 to 10), are selected and tested for hygromycin B resistance, and their genomic DNA isolated and analyzed, by PCR, to determine the presence or absence of a disrupted gene. A knock-out strain will produce a single PCR product that is larger than the wild-type gene product, due to the replacement of the wild-type gene with the larger hygromycin containing construct.

As shown in FIG. 9, chitin synthase mRNA abundance showed a 1.5 to 2 fold increase after $H_2O_2$ challenge. Thus, it appears that chitin synthase is up-regulated in response to oxidative challenge. These results indicate the chitin synthase 2 gene is under stress and/or developmental regulation. Thus upregulation, during the transition from the infectious mycelia to parasitic yeast growth states, may indicate the need of increased levels of chitin for continued pathogenesis. Thus, the increase in cell wall stability assocaited with increased synthesis of chitin is expected to make the pathogen less permeable to the toxic products of the macrophage oxidative burst or, to allow the cell wall to act as a defensive shield for the cell membrane.

Example 8

Small Inhibitory RNAs

In these experiments, the pWU55 telomeric vector is used for fungal transformation. The pBlueScript vector was used in order to construct the inhibitory expression component. In the first step, an upstream component of the *H. capsulatum* catalase B gene, from base pairs −916 to +66 with respect to the start of transcription, was ligated with the vector via a directed cloning into the EcoR I and Sal I sites. The catalase B promoter component was obtained by PCR, using genomic template, with the primers sequences as follows: iRCATBProm5': 5'-TTTGAATTCTGATCACTGCT-TCAATGCCGAGAG-3' (SEQ ID. NO. 11) and iRCATB-Prom3': 5'-TTTGTCGACGGCTGGGACCCTTCTTGAG-3' (SEQ ID NO. 12). The 5' primer (iRCATBProm5') was tagged with both a 5' EcoR I site followed by an internal Bcl I site. The 3' primer (iRCATBProm3') was tagged with a Sal I site. Next the Ura5 terminator sequence was obtained by PCR, using the pBY33 vector as template (kindly provided by W. E. Goldman). The amplified sequence was tagged with Sal I sequences at each end, with an internal Bcl I site in the 3' primer sequence, and ligated with the 3' end of the catalase B sequence using the pBS multiple cloning Xho I site.

Next, primers derived from the coding sequence of the gene of interest (e.g., Hcchs2) are constructed to produce a product of approximately 200 bp. For example, sequences from other *H. capsulatum* genes have been used in this system. The 5' primer used for amplification is tagged with a Xho I sequence and the 3' primer is tagged with an Apa I site. The final product is first digested with Apa I and then allowed to ligate. This ligation produces the inverted repeat sequence of approximately 400 bp and can then be used as template for PCR amplification. This last product is then digested with Xho I and then ligated with the Sal I digested catalase B-Ura5 pBluescript construct. The final product is amplified by PCR using the pBS construct as template with T7 and M13 reverse sequencing primers. This reaction produces significant amounts of the construct and this is digested with Bcl I and then ligated with BamH I digested pWU55 vector. This construct is then used to transform the *H. capsulatum* ura⁻ 5-21 strain. The catalase B promoter will produce a transcript of the small inverted repeat and this small RNA stem-loop transcript will initiate the de novo RNA quelling system in a gene specific matter. The Ura5 terminator primer sequences are as follows—HCURA5TERM-5': 5'-AAAAGTCGACCCAACTGCAA-GTATTGTTAC-3' (SEQ ID NO. 13); HCURATERM-3'; 5'-AAAAGTCGACTGATCAGGATGTGCTGTATCGCAT-CG-3' (SEQ ID NO: 14).

Publications referred to throughout this patent application are referred to in order to more fully describe the state of the art as known to those skilled in the art in the relevant fields as of the date of the invention described and claimed herein. It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. An isolated nucleic acid molecule for detection of *H. capsulatum* selected from the group consisting of:
   (a) a nucleic acid molecule comprising the sequence of SEQ ID NO: 1;
   (b) a nucleic acid molecule comprising the sequence of the complement of SEQ ID NO: 1;
   (c) a fragment of SEQ ID NO: 1, consisting of 21 or more consecutive nucleotides of SEQ ID NO: 1; and
   (d) a fragment of the complement of SEQ ID NO: 1, consisting of 21 or more consecutive nucleotides of the complement of SEQ ID NO: 1, wherein the isolated nucleic acid molecule hybridizes to at least one *H. capsulatum* chitin synthase intron sequence.

2. The isolated nucleic acid molecule of claim 1, wherein said fragment comprises up to 25 consecutive nucleotides of SEQ ID NO: 1 or up to 25 consecutive nucleotides of the complement of SEQ ID NO: 1.

3. The isolated nucleic acid molecule of claim 1, wherein the fragment consists of SEQ ID NO: 7 or SEQ ID NO: 8.

4. A method for detecting *H. capsulatum* in a sample, comprising the steps of:

(a) providing a sample; and
(b) assaying for the presence of DNA comprising a *H. capsulatum* chitin synthase gene in said sample, wherein the presence of said chitin synthase DNA indicates that the sample contains *H. capsulatum*, and wherein the step of assaying comprises exposing the sample to at least one isolated nucleic acid that hybridizes to at least one intron of the *H. capsulatum* chitin synthase 2 gene, and determining whether there is hybridization of the isolated nucleic acid to the sample, wherein a sample comprising *H. capsulatum* exhibits detectable hybridization and a sample lacking *H. capsulatum* does not exhibit hybridization, and wherein the isolated nucleic acid molecule for detection of *H. capsulatum* is selected from the group consisting of
   (i) a nucleic acid molecule comprising the sequence of SEQ ID NO: 1;
   (ii) a nucleic acid molecule comprising the sequence of the complement of SEQ ID NO: 1;
   (iii) a fragment of SEQ ID NO: 1 consisting of 21 or more consecutive nucleotides of SEQ ID NO: 1; and (iv) a fragment of the complement of SEQ ID NO: 1 consisting of 21 or more consecutive nucleotides of the complement of SEQ ID NO: 1, wherein the isolated nucleic acid molecule hybridizes to at least one *H capsulatum* chitin synthase intron sequence.

5. The method of claim 4, wherein intron 1 of the *H. capsulatum* chitin synthase 2 gene is assayed.

6. The method of claim 4, wherein the sample is obtained from a human.

7. The method of claim 4, further comprising the steps of:
   (a) conducting polymerase chain reaction (PCR) amplification using at least one nucleic acid molecule that hybridizes to at least one intron of the *H. capsulatum* chitin synthase 2 gene as an amplification primer; and
   (b) determining the presence or absence of the PCR product resulting from the amplification.

8. The method of claim 7, wherein the primers hybridize to intron 1 of the *H. capsulatum* chitin synthase 2 gene.

9. The method of claim 7, wherein the primers comprise at least one oligonucleotide molecule selected from the group consisting of SEQ ID NO: 7 and SEQ ID NO: 8.

10. A kit for detection of *H. capsulatum* comprising:
   (a) one or more containers comprising an isolated nucleic acid molecule selected from the group consisting of:
      (i) a fragment of SEQ ID NO: 1 consisting of 21 or more consecutive nucleotides of SEQ ID NO: 1; or
      (ii) the complement of a fragment of SEQ ID NO: 1, consisting of 21 or more consecutive nucleotides of the complement of SEQ ID NO: 1; and
   (b) at least one separate container comprising an isolated nucleic acid molecule comprising a chitin synthase intron DNA selected from the group consisting of:
      (i) a nucleic acid molecule comprising the sequence of SEQ ID NO: 1 or
      (ii) a nucleic acid molecule comprising the sequence of the complement of SEQ ID NO: 1.

11. The kit of claim 10, wherein the intron DNA is intron 1 of the chitin synthase 2 gene.

\* \* \* \* \*

UNITED STATES PATENT AND TRADEMARK OFFICE
CERTIFICATE OF CORRECTION

| | | |
|---|---|---|
| PATENT NO. | : 7,217,519 B1 | Page 1 of 1 |
| APPLICATION NO. | : 10/718955 | |
| DATED | : May 15, 2007 | |
| INVENTOR(S) | : Clayton H. Johnson et al. | |

It is certified that error appears in the above-identified patent and that said Letters Patent is hereby corrected as shown below:

On Title Page
Item 56
Under REFERENCES CITED

Page 2, FOREIGN PATENT DOCUMENTS, the reference "WO 804619 11/1997" should read -- EP 804619 11/1997 --

Under DETAILED DESCRIPTION

Column 18, Line 49, the phrase "(Chs 1-5) may be unregulated under several other conditions" should read -- (Chs 1-5) may be upregulated under several other conditions --

Column 28, Line 9, the phrase "Thus, the increase in cell wall stability associated with" should read -- Thus, the increase in cell wall stability associated with --

Signed and Sealed this

Sixth Day of November, 2007

JON W. DUDAS
*Director of the United States Patent and Trademark Office*